(12) United States Patent
Nowill

(10) Patent No.: US 9,566,330 B2
(45) Date of Patent: Feb. 14, 2017

(54) IMMUNOGENIC COMPOSITION FOR IMMUNE SYSTEM MODULATION AND USE THEREOF, METHOD FOR TREATING AND PREVENTING DISEASES, METHOD FOR INDUCING CELL REGENERATION AND METHOD FOR RESTORING IMMUNE RESPONSE

(76) Inventor: Alexandre Eduardo Nowill, Sao Paulo (BR)

( * ) Notice: Subject to any disclaimer, the term of this patent is extended or adjusted under 35 U.S.C. 154(b) by 0 days.

(21) Appl. No.: 14/006,077

(22) PCT Filed: Mar. 19, 2012

(86) PCT No.: PCT/BR2012/000072
§ 371 (c)(1),
(2), (4) Date: Oct. 23, 2013

(87) PCT Pub. No.: WO2012/122618
PCT Pub. Date: Sep. 20, 2012

(65) Prior Publication Data
US 2014/0037716 A1    Feb. 6, 2014

(30) Foreign Application Priority Data
Mar. 18, 2011 (BR) .................... 1100857

(51) Int. Cl.
| | | |
|---|---|---|
| *A61K 39/00* | (2006.01) | |
| *A61K 39/245* | (2006.01) | |
| *A61K 39/112* | (2006.01) | |
| *A61K 39/04* | (2006.01) | |
| *A61K 39/085* | (2006.01) | |
| *A61K 39/09* | (2006.01) | |
| *A61K 39/095* | (2006.01) | |
| *A61K 39/104* | (2006.01) | |
| *A61K 39/145* | (2006.01) | |
| *A61K 39/165* | (2006.01) | |

(52) U.S. Cl.
CPC ......... *A61K 39/245* (2013.01); *A61K 39/0002* (2013.01); *A61K 39/0275* (2013.01); *A61K 39/04* (2013.01); *A61K 39/085* (2013.01); *A61K 39/09* (2013.01); *A61K 39/092* (2013.01); *A61K 39/095* (2013.01); *A61K 39/104* (2013.01); *A61K 39/145* (2013.01); *A61K 39/165* (2013.01); *A61K 2039/55533* (2013.01); *A61K 2039/585* (2013.01); *A61K 2039/70* (2013.01)

(58) Field of Classification Search
None
See application file for complete search history.

(56) References Cited

U.S. PATENT DOCUMENTS 5,595,756 A * 1/1997 Bally et al. ................... 424/450

OTHER PUBLICATIONS

Collado-Romero et al. (Vet. Res., 41:23, 2010).*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042.*
Jain RK (Scientific American, Jul. 1994,58-65).*
Martini et al. (Am. J. Clin. Nutr., 54:1041-1046, 1991).*
McCarthy (Iowa Orthopaedic J., 26:154-158, 2006).*
Hobohm et al. (Crit Rev Immunol, 28:95-107, 2008).*

* cited by examiner

*Primary Examiner* — Brian J Gangle
(74) *Attorney, Agent, or Firm* — Nixon Peabody LLP; Linda B. Huber

(57) ABSTRACT

The present invention relates to immunogenic compositions for modulating the immune system, comprising a therapeutically effective quantity of two or more immuno-active antigenic agents with pathogen-associated molecular patterns (PAMPs) and/or danger-associated molecular patterns (DAMPs) and one or more physiologically acceptable carriers, excipients, diluents or solvents. The immunogenic compositions according to the present invention are used for producing medicaments for preventing and/or treating, and for preventing and/or treating infectious diseases, autoimmune diseases, allergic diseases, inflammation, arthritis, inflammatory diseases, transplant rejection, affections caused by vascular disorders, diseases caused by haemorrhagic or ischaemic cardiovascular accidents, ischaemia, heart attack and haemorrhagia leading to tissue destruction, heart, kidney, respiratory or liver insufficiency, cancer, malign and benign tumours and neoplasia. The present invention further relates to methods for inducing the regeneration of cells, tissues, organs and organic systems such as the circulatory, nervous and endocrine systems. Finally, the present invention relates to methods for restoring immune response in an animal, in particular a human being.

13 Claims, 7 Drawing Sheets

IMMUNOGENIC COMPOSITION FOR IMMUNE SYSTEM MODULATION AND USE THEREOF, METHOD FOR TREATING AND PREVENTING DISEASES, METHOD FOR INDUCING CELL REGENERATION AND METHOD FOR RESTORING IMMUNE RESPONSE

CROSS-REFERENCE TO RELATED APPLICATIONS

This application is the National Phase of International Application PCT/BR2012/000072, filed Mar. 19, 2012, which designated the United States. This application also includes a claim of priority under 35 U.S.C. 119(a) and 365(b) to Brazilian patent application No. PI 1100857-1, filed Mar. 18, 2011.

FIELD OF THE INVENTION

The present invention relates to immunogenic compositions for modulating the immune system comprising a therapeutically effective amount of two or more immunoactive antigenic agents presenting pathogen-associated molecular patterns (PAMPS) and/or danger associated molecular patterns (DAMPS) and one or more physiologically acceptable carriers, excipients, diluents or solvents.

Preferably the compositions of the present invention comprise immunoactive antigenic agents presenting pathogen-associated molecular patterns (PAMPS) and/or danger associated molecular patterns (DAMPS) selected from the group consisting of: (A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

It is another aspect of the present invention the use of immunogenic compositions in the manufacture of medicaments for prevention and/or treatment of infectious diseases, autoimmune diseases, allergic diseases, inflammation, arthritis, inflammatory diseases, transplant rejection, diseases caused by vascular disorders, diseases caused by hemorrhagic or ischemic cardiovascular events, ischemia, infarction and hemorrhage leading to tissue destruction, cardiac, renal, respiratory or liver disease, cancer, tumors and malignant and benign lesions.

The immunogenic compositions of the invention are also directly used in the prevention and/or treatment of infectious diseases, autoimmune diseases, allergic diseases, inflammation, arthritis, inflammatory diseases, transplant rejection, diseases caused by vascular disorders, cardiovascular diseases caused by injury or bleeding ischemic, ischemia, infarction and hemorrhage leading to tissue destruction, cardiac, renal, respiratory or liver disease, cancer, tumors and malignant and benign lesions.

The present invention further relates to methods for inducing cell regeneration, tissue regeneration, organ regeneration and regeneration of organic systems such as the circulatory system, nervous system and endocrine system.

Finally, the present invention relates to methods for renewal of the immune response in an animal, particularly humans.

BACKGROUND OF THE INVENTION

Of the Discovery of Antibiotics and Other Drugs

From the pioneering discovery of antibiotics in the second half of the 20th century, new antibiotics, semi-synthetic antibiotics and new chemotherapeutics with antimicrobial activity, have been developed on a large scale against most intracellular and extracellular bacteria. These developments have changed the history of medicine, allowing it to reach a wide spectrum of healing, for the vast majority of bacterial infectious diseases, which racked humanity.

Thus, the discovery of antibiotics was a major milestone, a watershed, because infection could be addressed and healed, in a specific way, with a clear relationship of cause and effect, and measurable when established. This discovery greatly expanded the ability of healing in medicine, with enormous positive impact on human health and lifespans. The discovery of antibiotics in the evolution and treatment of disease profoundly influenced the research and thinking of researchers from the success achieved by this experimental model (Reeves G, Todd I. Lecture notes on immunology. 2nd ed: Blackwell Scientific Publications, 1991; Neto V A, Nicodemo A C, Lopes H V. Antibióticos na prática medica. 6th ed: Sarvier, 2007; Murray P R, Rosenthal K S, Pfaller M A. Microbiologia Médica. 5th ed: Mosby, 2006; Trabulsi L R, Alterthum F. Microbiologia. 5th ed: Atheneu Editora, 2008).

Antibiotics were succeeded by the development and use of antifungal, antiparasitic and antiviral drugs. There was also the development of antineoplastic, cytostatic and cytotoxic drugs against malignant tumors, anti-inflammatory, anti-allergic and immunosuppressive drugs (anti-lymphocytes, neutralizing anti-leukocytes of the immune system) of hormonal and non-hormonal nature, with a huge range of applications, as in for infectious diseases, for inflammatory diseases of any origin, for autoimmune diseases, for genetic diseases, for vascular diseases, for allergic diseases, for trauma, for neoplastic diseases, for hormonal diseases, for degenerative diseases, among others.

Thus, the new drugs brought an enormous capacity for medical intervention, with numerous benefits, with definitive and partial cures, with the prolongation of life in incurable diseases, but with a huge morbidity due to side effects related to their lack of specificity to the pathophysiology of diseases treated.

Of the Innate Immunity

The innate immunity, in addition to preventing the entry of microorganisms and preventing their establishment, has another recently discovered vital function: discrimination between "self" and "not self" and the pattern recognition capability linked to the alarm and the command to start or inhibit an integrated immune response against an invading microorganism or to arrest, repair or inhibit a condition of destruction or self aggression to the body, for example, in trauma, autoimmune diseases and allergic diseases, among others. This dual capability was previously erroneously attributed exclusively to adaptive immunity. The innate immunity, through its own receptors, recognizes invading pathogenic microorganisms, autologous or even allogeneic neoplastic cells, or allogeneic or heterologous transplants as "not self", identifying them as not belonging to the organism. From that moment, it triggers an alarm and a joint innate and adaptive immune response to eliminate them or suppress a response deleterious to the human or animal organism (Goldsby R A, Kindt T J, Osborne B. Imunologia de kuby. 6 ed: ARTMED; 2008, 704 p; Janeway C, Travers P, Walport M, Slhlomchik M J. Immunobiology five. 5 ed: Garland Pub.; 2001. 732 p.; Voltarelli J C. Imunologia clinica ha pratica medica: atheneu editora; 2009; Janeway C A, Jr., Medzhitov R. Innate immune recognition. Annual review of immunology. 2002; 20:197-216. Epub 2002 Feb. 28; Matzinger P. The danger model: a renewed sense of self. Science. 2002; 296 (5566):301-5. Epub 2002 Apr. 16; Steinman R M, Banchereau J. Taking dendritic cells into medicine. Nature. 2007; 449 (7161): 419-26. Epub 2007 Sep. 28.; Beutler B A. TLRs and innate immunity. Blood. 2009; 113 (7): 1399-407. Epub 2008 Sep. 2; Moresco E M, LaVine D, Beutler B. Toll-like receptors. Current biology: CB. 2011; 21 (13): R488-93. Epub 2011 Jul. 12).

The (default/standard/pattern?) recognition, of "not self", of an invasive germ, of a neoplastic cell or an altered or transplanted cell is performed by sentinel cells, represented by epithelial cells, mucosal cells, and the stromal cells, such as pericytes, dendritic cells, macrophages and fibroblasts, among others. These cells, strategically distributed throughout the body, have PRRs (Pattern Recognition Receptors) and DRRs (Danger Recognition Receptors) which are receptors respectively able to recognize a) standard identification molecules, characteristic of a wide range of microorganisms, and b) certain patterns for chemical and physical of said inert substances and changes to metabolic stress, such as release of free radicals and tissue chemical changes, caused by ionizing radiation or by chemical substances, among others.

The PRR does not discriminate one specific individual microorganism, but the presence of microorganisms other than the human body. Each PRR receiver may bind to several different pathogens, recognizing as PAMPs (Pathogen Associated Molecular Patterns) carbohydrates, lipids, peptides and nucleic acids from bacteria, viruses, fungi or parasites that are not found in the human or animal body.

The DRRs discriminate that there is tissue damage, a dangerous situation caused by not live or inert agents. The DRRs identify DAMPs (Danger Associated Molecular Patterns) associated with tissue damage by toxic substances, radiation, or trauma, which cause metabolic stress, release of free radicals and chemical changes in tissue, recognized by these receptors. (Janeway C, Travers P, alport M, Slhlomchik M J. Immunobiology five. 5th ed: Garland Pub.; 2001. 732 p.; Matzinger P. The danger model: a renewed sense of self. Science. 2002; 296 (5566): 301-5. Epub 2002 Apr. 16; Beutler B A. TLRs and innate immunity. Blood. 2009; 113 (7): 1399-407. Epub 2008 Sep. 2; Moresco E M, LaVine D, Beutler B. Toll-like receptors. Current biology: CB. 2011; 21 (13):R488-93. Epub 2011 Jul. 12).

Thus, sentinel cells via their PRRs and their DRRs, have a role in the breakdown of which belongs ("self") and which is does not belong (not "self") and triggering inflammation and immune response, via recognition of PAMPs of invading pathogens and DAMPs caused by neoplastic cells and toxic substances or modifications due to trauma, leading to a situation of real danger to the human and animal organism.

Immediately, these activated sentinel cells give alarm signals, triggering the innate immune response through the NF-kB (Nuclear Factor-kB) signal translation system, leading to the secretion of pro-inflammatory cytokines and the IRF signal translation system, that produces Type I alpha and beta interferons. These cytokines, together, acting on cells and vessels, cause a local inflammatory process, initially to contain the invading agent, autologous (tumor cell), heterologous (microorganisms, prions, grafts and transplants) or allogeneic (grafts and transplants), or to repair danger situations. This contention happens through antibodies, pre-existing, opsonizing acute phase proteins and through leukocytes and macrophages, which engulf and start to destroy the extracellular and intracellular microorganisms respectively, or eliminating other etiologic agents of any kind.

In gout, in silicosis, the chemical aggression, in foreign body granulomas, in trauma, the inflammatory process is formed to eliminate the offending agent if possible and then induce tissue healing and regeneration. When the offending agent is not eliminated the inflammation is perpetuated and causes an incurable or uncontrollable chronic inflammatory disease, stable or progressive, which compromises the life or health of patients.

Interaction and Integration of Innate Immunity with Adaptive Immunity

Simultaneously at the site of invasion, aggression and inflammation, the innate immunity sentinel cells with the APC role (Antigen Presenting Cells), such as dendritic cells and macrophages, phagocytosise and pinocytosise microorganisms or tumor cells, or transplanted cells, among other aggressors and process their antigens. These APC cells pulsed by the antigens migrate to regional lymph nodes and activate them. The APC cells in reactive lymph nodes, activated and mature present the antigens to lymphocytes, secrete cytokines and thereby induce, coordinate, polarize, amplify and maintain an adaptive immune response specific to the invading germs, or neoplastic cells, or to transplanted cells, or other offending agent, allowing them to be fought and eliminated, where feasible and the consequent cure of the infection or inflammation and repair and regeneration or wound healing.

Thus, these immune mechanisms fight disease through the innate and adaptive responses in an integrated and synergistic way, performed by sentinels cells, APC function sentinels, and innate immunity effectors, cellular and molecular in conjunction with the cellular and molecular effectors of adaptive immunity that are respectively lymphocytes, cytokines and antibodies.

Thus, the interaction of the two immunities, innate and adaptive, in the context of an infection or immune response against an aggressor of any kind helps to combat the disease in an integrated and synergistic way. The integration of the two initially occurs by the action of the innate immunity cells with APC function, such as dendritic cells and macrophages, but mainly by the activity of dendritic cells, as they are the ones that are able to initiate an adaptive immune response against a primary infectious or parasitic agent, effectively protecting the body.

As noted macrophages also function as APC cells, but are more specialized and involved as part of the effector loop in phagocytosis and in the elimination of microorganisms. B lymphocytes, when mature, are also APC cells and its most well-known action is the presentation of antigens to the T lymphocytes, within the framework of cooperation of both lymphocytes to produce antibodies against T-dependent antigen, and the secondary antibody response. Macrophages, like other myeloid cells, are also involved in suppressing immune response in cancer and in incurable chronic infections. In these cases its performance is unfavorable to the defense of the organism because it suppresses the immune response and create tumor facilitation. A malignant tumor disease is characterized by causing an initial silent inflammation, imperceptible, and in the end it becomes extremely pro inflammatory and symptomatic through the TH17 profile inflammatory tissue, which usually leads the patient to prolonged suffering.

When co-stimulatory molecules are not expressed on the APC cell surface, by the absence of the alarm signal characterized by the lack of activation of PRRs by PAMPs and DAMPs, only the first signal occurs, given by the TCR. After the TCR binds with the antigen, in the absence of the second signal, the T lymphocyte becomes tolerant to the specific antigen shown and aborts the immune response.

On the other hand, the CD 40L molecule of activated T lymphocytes, when it binds to the CD40 molecule on the APC cells, significantly increases the expression of CD80 and CD86 molecules, increasing the current response, which thus occurs only when the adaptive T response is already engaged in defending the body. The third signal given by cytokines such as IL-1, is given only by the APC cells after the binding of co-stimulatory molecules and the emission of the second signal. The IL-1 secreted by the APC cells acts on lymphocyte cells and leads to the complete expression of the receptor for IL2 and to the production of cytokines by virgin or memory lymphocytes engaged in response to the initiating clonal expansion.

Therefore the activation of innate immunity by pathogens is the key to unleashing the second and third signals and the occurrence of a potentially effective immunity, through the full activation of T lymphocytes engaged in the response. Without the occurrence of the second and third signal, the response is aborted and generates a tolerance specific to the antigen presented.

At the same time that the neutrophils, monocytes and macrophages initiate combat to bacteria and to other infectious agents by the linkage of PAMPs with PRRs on antigen presenting cells (APC), they activate dendritic cells and macrophages, local and newly arrived. These cells phagocytosise and pinocytosise bacteria and bacterial antigens, processing them and starting the maturation process. The activated and maturing dendritic cells now migrate to regional lymph nodes to present antigens and initiate immune response against the invading agent.

The mature antigen-pulsed APC cells, especially dendritic cells, in lymph nodes, collaborate with the T and B lymphocytes and initiate the adaptive response. Dendritic cells are the most potent cells for the presentation of antigens and the only APC cells able to activate a virgin CD4 T lymphocyte and to start a new immune response.

After a period of approximately seven days in the lymph node, the collaboration between blank CD4 lymphocytes, which become T CD4 Th2, with B lymphocytes and antigen presenting dendritic cells, initiates the differentiation of specific sensitized B lymphocytes. These B cells, now activated, recognize bacterial antigens by surface immunoglobulins, after contact with these antigens, proliferate, mature, and differentiate into plasma cells that now secrete specific antibodies against this bacterium. Infections of all types, bacterial, viral, fungal and parasitic may, in general, in the acute phase, evolve to a full cure with regeneration and healing, or for a cure with sequelae. They can also develop into an incurable chronicity, with or without control of the disease, to chronicity with healing, with or without sequelae, or to death.

Polarization of the Immune Response

The immune profiles known and induced by dendritic cells by direct and indirect contact with the different cytokines and generated by T CD4 cells are of four types:

a) cellular Th1 profile, which generates cellular immunity mediated by cells;

b) humoral Th2 profile, which generates humoral immunity mediated by antibodies;

c) tissue or inflammatory Th17 profile, which generates inflammatory tissue immunity, also mediated by cells and cytokines, which induce an important inflammation for the elimination of certain pathogens, and d) Treg/Tr1 profile, which suppresses the immune response and controls, by inhibiting the other three profiles described above, ensuring the return of the body equilibrium state.

e) profiles not yet fully established, as the Tfh (follicular Helper) of the humoral response, the Th9 profile for certain parasites, or other profiles that may be discovered.

Thus, the various profiles ensure the defense of the organism and the elimination of causative heterologous (infectious) agents invading and colonizing autologous (neoplasia). The last profile ensures the termination of the immune response, the balance, the regeneration, the safe return to normalcy and it prevents self-injury and allergy and is therefore vital to the health and preservation of the human species and animal, as much as the other profiles.

The phenomenon of polarization of the immune response is defined as the predominance of a certain immunological profile such as Th1 or Th2 at the expense of other profiles that become secondary or null. This phenomenon happens according to the type of attack suffered by the body. That is, according to the type of infection, pathology, and infection stage or pathology stage, the different type of immune response will be predominant, and it may be a cellular, humoral, tissue, or immune-regulatory response, while other types of immune responses are inhibited, resulting in the phenomenon of polarization.

By definition, in polarization a profile is dominant, but other non-dominant profiles are also needed, and expressed in a complementary manner that will help eliminating the disease. For example, tuberculosis is the appearance of Th17 cells in the lung which allows Th1 cells to settle and may lead to cure this infection in the lung parenchyma (Stockinger, B. and Veldhoen, M. Differentiation and function of Th17 T cells. Current Opinion in Immunology, 19 (3), pp. 281-286. 2007). In viral infections, the CTL cells of Th1 profile destroy cells infected by viruses, to eliminate the virus. However, antibodies are required to prevent the virus from infecting other healthy cells and thus preventing the spread of infection. The coordinated assembly of the two profiles is essential for the healing of certain viral infections. Certain intestinal infections by extracellular Gram-negative bacilli require, for its cure, in the final stage, besides the Th2 profile, the generation of a supplementary Th17 profile capable of generating a strong inflammation, necessary to eliminate this type of bacteria.

In conclusion, due to the fact that the dendritic cells are the only professional APC cells capable to initiate a primary adaptive immune response and are the most potent in triggering a secondary specific immune response, in any profile, they are then commanding the interaction and integration of innate immunity with adaptive immunity to produce an effective immune response capable of curing a disease. Dendritic cells in collaboration with other APC and sentinel cells in contact with different aggressors in different functional states, in the inflammation sites, in the lymph nodes, in the spleen, in the mucous membranes, are able to lead, coordinate, polarize, and amplify the adaptive immune response, primary and secondary, e.g., specific for the peptides of invading pathogens, which in this case is the most appropriate for the removal of the ongoing infection.

Therefore, dendritic cells and other APC cells are key cells of the innate immune response, since they evaluate the nature of the autologous and heterologous causative agent, i.e., the type of pathogen or colonizing cells and aided by the sentinel cells, they measure and evaluate the size of the heterologous or autologous aggression, its extension, its intensity and aggressiveness, besides commanding the adaptive response with the profile and the intensity required for the elimination of the pathogen.

After differentiation, a re-differentiation can occur, induced by the microenvironment and/or the type of antigen or its presentation, in which a Th1 or Th2 profile can be exchanged for an inflammatory profile or an immunosuppressant profile or vice versa. This extreme plasticity of the immune system to differentiate or re-differentiate in either direction indicates a strategic window for manipulation of the immune system, during infection, when the direction taken by the polarization is not the best one for curing the infection process or neoplasia.

As an illustrative example, we have what happens in a severe infection or septicemia, when the massive inflammation caused by the large number of microorganisms which touch the sentinel cells throughout the body, induces also a Th17 a profile, which in turn increases the inflammation more and therefore becomes detrimental, leading to tissue destruction, rather than inducing healing. In these cases the Th17 profile, by tissue destruction and the amplification of inflammation, is mainly responsible for the generation of clinical complications such as severe ARDS (acute respiratory distress syndrome in adults), lung shock, renal failure, or shock, that compromises healing.

The re-differentiation of polarization for the Th1 or Th2 profiles, with the inhibition of massive inflammation, is the logical and strategic path for a designed or prepared immunotherapy to try to resolve this dramatic and deadly type of situation, during a severe infection or sepsis, which has a significant mortality and morbidity and for which antibiotics and other antimicrobials, in current patterns such as single mode, have disappointing anti-infective results. The same example applies to serious intra cellular bacterial, fungal, viral and parasitic infections, with extensive tissue destruction and massive inflammation, usually of poor prognosis.

The Use of Adjuvants to Stimulate Immune Response

The human and animal organisms do not usually produce antibodies against soluble proteins, necessitating the use of so-called nonspecific or unrelated adjuvants to obtain the desired immune response. These adjuvants used since the dawn of immunology, in immunizations and in vaccine applications, were and are made up of parts of microorganisms, mineral oils and other substances that activate the innate immunity, which then gives the alarm and control necessary for the development of desired immune response to the protein or to the vaccine in question (GOLDSBY R A, KINDT T J, OSBORNE B A. IMUNOLOGIA D E KUBY. 6 ed: ARTMED; 2008. 704 p); (Janeway C, Travers P, alport M, Slhlomchik M J. Immunobiology five. 5 ed: Garland Pub.; 2001. 732 p.); (VOLTARELLI J C. IMUNOLOGIA CLINICA N A PRATICA MEDICA: ATHENEU EDITORA; 2009); (Janeway C A, Jr., Medzhitov R. Innate immune recognition. Annual review of immunology. 2002; 20:197-216. Epub 2002 Feb. 28.); (Matzinger P. The danger model: a renewed sense of self. Science. 2002; 296 (5566): 301-5. Epub 2002 Apr. 16.); (Steinman R M, Banchereau J. Taking dendritic cells into medicine. Nature. 2007; 449 (7161): 19-26. Epub 2007 Sep. 28.); (Beutler B A. TLRs and innate immunity. Blood. 2009; 113 (7): 1399-407. Epub 2008 Sep. 2.); (Moresco E M, LaVine D, Beutler B. Toll-like receptors. Current biology: CB. 2011; 21 (13): R488-93. Epub 2011 Jul. 12).

It should be noted that the use of adjuvants for immunization, despite being one of the oldest features, and still current, highly used and essential for vaccinations and for studies of immunology, was considered only as a useful nonspecific effect. It was not envisioned, for more than a century, its role in the innate immunity in the discrimination of what is "Self" and not "Self" and its unique and fundamental capacity to the survival of the human species and animals: to give the alarm signal and the command to start or not start, or inhibit, an integrated, protective or healing, innate and adaptive, immune response (GOLDSBY R A, KINDT T J, OSBORNE B A. IMUNOLOGIA D E KUBY. 6 ed: ARTMED; 2008. 704 p); (Janeway C, Travers P, Walport M, Slhlomchik M J. Immunobiology five. 5 ed: Garland Pub.; 2001. 732 p.); (VOLTARELLI J C. IMUNOLOGIA CLINICA N A PRATICA MEDICA: ATHENEU EDITORA; 2009); (Janeway C A, Jr., Medzhitov R. Innate immune recognition. Annual review of immunology. 2002; 20:197-216. Epub 2002 Feb. 28.); (Matzinger P. The danger model: a renewed sense of self. Science. 2002; 296 (5566): 301-5. Epub 2002 Apr. 16.): (Steinman R M, Banchereau J. Taking dendritic cells into medicine. Nature. 2007; 449 (7161): 419-26. Epub 2007 Sep. 28.); (Beutler B A. TLRs and innate immunity. Blood. 2009; 113 (7): 1399-407. Epub 2008 Sep. 2.); (Moresco E M, LaVine D, Beutler B. Toll-like receptors. Current biology: CB. 2011; 21 (13): R488-93. Epub 2011 Jul. 12).

Today's Anti-Infective and Anti-Cancer Treatments

A large number of medical materials, labor hours, medicines and hospital beds could be better used with a therapy that assessed, prioritized and optimized the variables that affect the displacement of the biological balance in favor of the patient and modulated his or hers immune system, decreasing its inefficiencies and allowing for a large number of medical discharges, in less time. The prior art has yet to provide alternatives to perform an intended repolarization of the immune system in real time, or time to change or reverse its response to a ongoing disease or illness, if possible to improve the quality of life, or extend the life span, or assist the process of combating the ongoing disease or illness on the patient.

Bacterial, fungal, viral, parasitic and neoplastic resistance to antibiotic, antifungal, antiparasitic and antineoplastic medicines used in clinical practice is seen as the main obstacle to the cure of bacterial, fungal, viral, parasitic and tumor diseases, and is considered a serious health problem on a global scale. This problem is circumvented by using appropriate and rational use of antibiotic, antimicrobial and anticancer medicines and with the advent of new more potent drugs. However, sooner or later, resistance is always inevitably established, and yet a solution to this problem has not been found. As antibiotics, antifungal, antiviral, antiparasitic and antineoplastic agents are considered as the only valid and effective anti-infective, antiparasitic and antineoplastic treatment modalities, the prospect of future treatments is disturbing and dark, due to the phenomenon of microbial and tumor resistance.

Antibiotics, antifungals, antivirals, antiparasitics and antineoplastic agents can be used at any stage of the infectious bacterial, fungal, viral, parasitic and tumor conditions. However, antibiotics, antimicrobial and anticancer fail to cure most advanced, pervasive and severe bacterial, fungal, viral, parasitic, and cancer conditions that have, in general, a very high rate of mortality and morbidity.

Furthermore, the discovery of new drugs is directed to drugs that are capable of eliminating the causative agent and cure infection, infestation and neoplasia based on the concept of a single drug capable of curing infectious, parasitic, and neoplastic disease.

Treatment of Neoplasms at the Present Time

Cytokines such as interleukin 2 and type I alpha and beta interferons, are used for the treatment of immunogenic tumors such as melanoma and hypernephroma. Cytokines a bone marrow colonies growth factors function are used to combat anemia, leucopenia, cytopenias of the elements in the peripheral blood, caused by disease or treatment, with good results. Type I Interferons are widely used to combat viral hepatitis B and C, with good results, and with less significant results for the treatment of multiple sclerosis. Transplantation of allogeneic and autologous bone marrow is used for the treatment of cancer. Passive immunotherapies with CTL CD8 dendritic cells, white blood cells, autologous or allogeneic, with or without cytokine, are used for the treatment of certain tumors, and the results are still not very significant or significant at all, but limited to certain exceptional pathologies, as virus-induced tumors that grow in immunosuppressed transplant patients. In these cases, passive immunotherapy with specific T CTL CD8 e CD4 cells for the EBV virus, are usually successful and cure these exceptional tumors that only grow in immunosuppressed patients. However, it is noteworthy that these techniques, as well as other similar but less effective ones, did not develop agents or sets of agents capable of effectively immunomodulate the immune system in order to start reacting against any invading pathogen (infection), or autologous colonizer (tumors) that is present in the body of the individual to be treated, or that can resolve dysautonomia states in the primary or secondary genetic immune systems, that lead to states of self-harm by the immune system, which should defend the body from aggression.

Examples include successful cancer treatment that uses an immunomodulatory agent containing molecular patterns recognizable by the PPRs, the use of the BCG vaccine as one of the rare established techniques, which are accepted and proven, that use immunomodulation as a means of treatment. Brake and colleagues described the use of BCG immunotherapy in patients with superficial bladder cancer, who were in Stage TI (Brake M, Loertzer H, Horsch R, Keller H (2000). "Long-term results of intravesical bacillus Calmette-Guérin therapy for stage TI superficial bladder cancer". UROLOGY 55 (5): 673-678). Immunotherapy was applied in patients after a complete transurethral resection of bladder tumor by applying a second cycle of BCG in the case of recurrent superficial tumors. The conclusion was that immunotherapy with BCG after transurethral resection of bladder tumors represents a highly effective primary treatment for TI stage bladder cancer, with a 89% rate of tumor-free survival in all patients.

Following this line, Burger and colleagues have demonstrated a randomized comparative essay, in which patients with noninvasive bladder cancer of the muscle layer made use of BCG or cell therapy with autologous macrophages (BEXIDEM®) (Burguer M, Thiounn N, Denzinger S, Kondas J, Benoit G, et. al (2010). "The application of adjuvant autologous antravesical macrophage cell therapy VS. BCG in non-muscle invasive bladder cancer: a multicenter, randomized trial. Journal of Translation Medicine, 8:54. doi: 10.1186/1479-5876-8-54). Compared with BCG, the incidence of adverse events was significantly lower in the treatment BEXIDEM (26% and 14%, respectively). However, the recurrence rate of tumor in patients treated with BEXIDEM was significantly higher than in patients who received BCG as adjuvant therapy.

Donald et al described the use of BCG as a form of immunotherapy in patients with melanoma (Donald L. Morton, M.D., Frederick R. Eilber, M.D., E. Carmack Holmes, M.D., John S. Hunt, M.D., et. al (1974). "BCG Immunotherapy of Malignant Melanoma: Summary of a Seven-year Experience". Ann. Surg., p: 635-641). Patients selected for the study had recurrent melanoma, known residual disease, or high risk of developing recurrence. First, direct injections were applied in malignant nodules of melanoma using 0.1-0.5 cc of BCG in each intracutaneous and subcutaneous lesion. Patients who were in Stage II were treated with BCG immunotherapy alone or with BCG and allogeneic melanoma cells. BCG was administered alone or as an adjuvant mixed with tumor cells in patients in stage III disease. Patients with intradermal metastases who were treated with intratumoral injections of BCG were those who responded better to treatment, and three factors appeared to be correlated with response to BCG immunotherapy: the location of metastasis, the amount of tumor present and the immunocompetence of the patient. There was low antitumor activity of BCG in patients with bulky disease or visceral metastases. The result showed that 31% of patients with intradermal metastases were found free of disease recurrence for a period of up to 6 years after the start of immunotherapy.

The immunotherapy described by Grant et al consists of the use of BEC2 (idiotypic antibody which mimics the GD3 ganglioside present on the surface of most tumors of small cell lung cancer) in combination with BCG (Grant S C, Kris M G, Houghton A N, Chapman P B (1999). "Long Survival of Patients with Small Cell Lung Cancer after Adjuvant Treatment with the Anti-Idiotypic Antibody BEC2 Plus Bacillus Calmette-Gue". Clinicai Cancer Research, Vol. 5, 1319-1323). The applied dose in patients with lung cancer was 2.5 mg for a period exceeding 10 weeks. Patients treated with immunotherapy had a significant increase in survival and survival free of recurrence of the disease when compared to a similar group of patients.

Popiela et al evaluated the use of BCG immunotherapy and chemotherapy with FAM (5-fluorouracil, adriamycin, mitomycin C) in patients with stage III or IV gastric cancer, that previously underwent curative gastrectomy for that cancer (Popiela T, Kulig J, Czupryna A, Sczepanik A M, Zembala M (2004). "Efficiency of adjuvant immunochemotherapy following curative resection in patients with locally advanced gastric cancer". Gastric cancer, 7: 240-245). Patients were randomly divided into 3 groups: BCG+FAM, FAM, and control (surgery only). The dose of BCG immunotherapy was administered at 2-4 viable units per dose. It was observed in general a 10 year survival rate of 47.1% in the immunotherapy group. Powles and colleagues reported a study in which patients with acute myeloid leukemia were treated with BCG and dead allogeneic tumor cells. The dose of BCG was estimated to be about $10^6$ organisms (R L Powles, P J Selby, D R Jones, J A Russel, H G Prentice, et. al (1977). "Maintenance of remission in acute myelogenous leukemia by a mixture of B.C.G. and irradiated leukemia cells". THE LANCET, 1107-1110). Improvement was observed in patients, who showed remission for a period, leading to the conclusion that the immunotherapy with a combination of leukemia tumor cells and BCG may be effective to prolong remission. Likewise Vuvan and et al described the use of BCG immunotherapy in patients with acute non-lymphocytic leukemia (H. Vuvan, D. Fiere, M. Doillon, C. Martin, B. Coiffier, et. al (1978). "BCG Therapy in Acute Non Lymphoid Leukaemias". Scand J Haematol 21, 40-46). A randomized study was conducted in which patients were divided into 2 groups: treated with chemotherapy alone and treated with chemotherapy and BCG, the BCG being administered during the interval of chemotherapy cycles at doses of 6×10$^8$ viable units. The result showed that patients receiving immunotherapy had a higher survival rate as compared to the group receiving only chemotherapy. Furthermore, it was observed that BCG appeared to be more effective in patients older than 40 years.

Finally, Hsueh et al used a therapeutic vaccine consisting of melanoma cells called Canvaxin (Hsueh E D, Essner R, Foshag L J, Ollila D W, Gammon G, et al (2002). "Prolonged Survival After Complete Resection of Disseminated Melanoma and Active Immunotherapy with a Therapeutic Cancer Vaccine". Journal of Clinicai Oncology, Vol 20, n 23, pp 4549-4554). All patients were tested with PPD (purified protein derivative) before receiving therapy with the vaccine. For the first two treatments, the vaccine was mixed with BCG. In the first injection, BCG was applied in a dose from 2.7 to 10.8×10$^6$ colony forming units in PPD negative patients and half this dose in PPD positive patients. There was a prolongation of survival in patients who received, after surgery, active immunotherapy with Canvaxin.

The aforementioned studies with the use of BCG, although they are using an immunostimulating agent separate from the causative agent of the disease or disorder to cause desirable effects in patients, whether or not in combination with other medical procedures and treatments as proposed in the present invention, are not however taking advantage of using multiple antigenic components that are associated with distinct pathogen molecular patterns, especially a combination that represents intracellular and extracellular bacteria, viruses, parasites, fungi and yeasts. The aforementioned research groups and studies only used BCG in a simple adjuvant function without taking into account the basis of the present invention that aim to activate memory or blank cells, which can be inactivated throughout various body tissues through a wide range of pathogen associated molecular patterns that can enable the largest possible number of memory and effector cells. By not presenting this combination of distinct antigenic nonspecific agents able to stimulate innate and specific immunity as described, many populations of immune memory cells will no longer be activated according to the arguments presented, which will not lead to a recontextualization, renewal and reprogramming of the immune response, that is as effective as presented herein.

Neither the state of the art describes the importance of immunization protocols and of the local and distal applications of immune-stimulatory agents, and how a lot of applications in different parts of the body are necessary, for in a programmed and intentional way, cause the PAMPS and DAMPS molecular patterns to reach the tissues that hold the APC cells in adequate quantity and quality to provoke optimal response and polarization.

Tanaka et al (Tanaka N., Gouchi A. Ohara T., Mannami T., Konaga E., Fuchimoto S., Okamura S., Sato K., Orita K (1994). "Intratumoral injection of a streptococcal preparation, OK-432, before sugery for gastric cancer. A randomized Trial. Cooperative Study Group of Preoperative Intratumoral Immunotherapy for Câncer". Câncer, 74(12): 3097-3103) and Yasue and et al (Yasue M., Murakami M., Nakazato H., Suchi T., Ota K (1981). "A Controlled Study of Maintenance Chemoimmunotherapy VS Immunotherapy Alone Immediately Following Palliative Gastrectomy and Induction Chemoimmunotherapy for Advanced Gastric Cancer". Cancer Chemother Prasmacol, 7: 5-10.) report the use in gastric cancer patients of an immunomodulatory agent prepared from attenuated *Streptococcus pyogenes* called OK-432. Such an agent is able to activate the immune system and cause regional degeneration of the affected tissue in stomach carcinomas. Tanaka describes the preoperative use of 10KE of OK-432 injected endoscopically, and doses of 1KE to 5KE in intradermal injections in case of metastases in the lymph nodes, post-operation. Tanaka concluded that intratumoral injections of OK-432 may have a beneficial clinical effect in patients who are in Stage III gastric cancer, because it seems to improve survival in this subgroup of patients. Yoshida et al (Yoshida K., Sugiura T., Takifuji N., Kawahara M., Matsui K., et al (2007). "Randomized phase II trial of three intrapleural therapy regimens for the management of malignant pleural effusion in previously untreated non-small cell lung câncer: JCOG 9515. Lunger Câncer, 58: 362-368) evaluated the efficacy and toxicity of OK-432 (0.2 KE/kg, and the maximum dose 10KE/Kg) as pleural therapy in control of malignant pleural effusion in patients with non-small cell lung cancer, previously untreated. Apart from OK-432, bleomycin and cisplatin with etoposide, were also assessed as intrapleural therapy. It was concluded that the best intrapleural therapy used was the use of OK-432, because it was the one that had the best survival rate, free of disease, and the lowest rate of pleural recurrence.

Aftergut et al (Kent Aftergut, MD, Mary Curry, MD, Jack Cohen, DO (2005). "*Cândida* Antigen in the Treatment of Basal Cell Carcinoma". Dermatol Surg, 31: 16-18) studied the intralesional use of *Candida* antigens in the treatment of basal cell carcinoma. The study shows that 56% of patients had complete regression of tumor cells. The antigens were administered in doses of 0.1 mg via intradermal injection. Again, the present invention is distinguished by the use of a very elaborate and more complex combination of antigenic components, having the potential to achieve more favorable results when used alone or in combination with other therapies. The study described by Miles et al (Miles D W, Towlson K E, Graham R, Reddish M, Longenecker B M, et al. (1996). "A randomised phase II study of sialyl-Tn and DETOX-B adjuvant with or without cyclophosphamide pre-treatment of the active specific immunotherapy of breast cancer". British Journal of Cancer, 74:1292-1296) investigated the occurrence of improvement in the immune response caused by the association of sialyl-Tn-KLH with DETOX-B (containing in its composition *Mycobacterium phlei* cell wall skeleton) in patients with breast cancer, when subjected to a pre-treatment with low doses of cyclophosphamide. An emulsion of 0.5 ml, composed of STN-KLH with DETOX-B was used. As a result, it was observed that all the patients developed IgM and IgG against the sialyl-Tn, and patients who received a cyclophosphamide pretreatment had a significantly greater increase of IgM. Korec et al present a study in which 11 patients with different tumor types and 3 patients with thrombotic thrombocytopenia purpura associated with mitomycin C, were treated with a extracorporeal plasma perfusion through filters containing *Staphylococcus aureus* immobilized protein A (Korec S, Smith F P, Schein P S, Phillips T M (1984). "Clinicai experiences with extracorporeal immunoperfusion of plasma from cancer patients". J Biol Response Mod. 3(3): 330-5). As a result, there was a modest antitumor effect generated by immune-perfusion. In 10 properly treated patients, there was a measurable reduction of tumor (40% mass reduction of the original tumor).

Engelhardt et al (Engelhardt R, Mackensen A, Galanos C (1991). "Phase I Trial of Intravenously Administered Endotoxin (*Salmonella abortus equi*) in Cancer Patients". CÂNCER. RESEARCH 51, 2524-2530) described an assay related to intravenous endotoxin administration, prepared from *Salmonella abortus equi* lipopolysaccharide (essentially free of protein and nucleic acid). 24 patients aged 33 to 67 years were selected, with 10 patients diagnosed with colorectal cancer, 5 with non-small cell lung cancer, 2 with carcinoma, 2 with pancreatic cancer, 2 with sarcoma, one with gallbladder cancer, 1 with cancer in the anus and 1 with cancer in the trachea. The pancreatic cancer patients received no prior treatment, while other patients had been treated with radiation, chemotherapy and/or surgery, these treatments being finalized four weeks before the start of the study treatment. The applied initial dose of endotoxin was 0.15 ng/kg, and the maximum tolerated dose is 4 ng/kg. The results showed two partial responses and four occurrences of disease stabilization in patients with colorectal cancer, and as these patients were in the group with the largest number of participants does not necessarily indicate that this type of tumor has more sensitivity to lipopolysaccharides that other tumors studied in the search. It was also verified disease stabilization for a period in patients with non-small cell lung cancer, renal cell cancer and tracheal cancer. Otto et al describe the phase II of the study reported by Engelhardt. On this stage, 15 patients with non-small cell lung cancer, and 27 with colorectal cancer, received 4 injections of endotoxin (4 ng/kg dose) and 1600 mg of ibuprofen orally every 2 weeks. The results showed improvement in 3 patients with colorectal cancer, of which 2 patients had partial remission of the tumor, which was stabilized during 7 to 8 months, respectively, and one of them had complete tumor remission. A minimal antitumor effect was also observed in patients with lung cancer.

As we can observe in the examples of the prior art described by Aftergut (Kent Aftergut, MD, Mary Curry, MD, Jack Cohen, DO (2005). "*Candida* Antigen in the Treatment of Basal Celi Carcinoma". Dermatol Surg, 31: 16-18), Miles (Miles D, Towlson K E, Graham R, Reddish M, Longenecker B M, et al. (1996). "A randomised phase II study of sialyl-Tn and DETOX-B adjuvant with or without cyclophosphamide pretreatment of the active specific immunotherapy of breast cancer". British Journal of Cancer, 74:1292-1296), Korec (Korec S, Smith F P, Schein P S, Phillips T M (1984). "Clinicai experiences with extracorporeal immunoperfusion of plasma from cancer patients". J Biol Response Mod. 3(3): 330-5), Engelhardt (Engelhardt R, Mackensen A, Galanos C (1991). "Phase I Trial of Intravenously Administered Endotoxin (*Salmonella abortus* equi) in Cancer Patients". CANCER RESEARCH 51, 2524-2530) e Otto (Otto F, Schmid P, Mackensen A, ehr U, Seiz A, et. al (1996). "Phase II trial of intravenous endotoxin in patients with colorectal and non-small cell lung câncer". Eur J Cancer, 32A(10): 1712-8), only one antigenic component was used in each respective study.

William B. Coley was a pioneer in the research linking the use of immunotherapy in cancer patients (Edward F. McCarthy, MD. "The Toxins of Willian B. Coley and the treatment of bone and soft-tissue sarcomas". The Iowa Orthopaedic Journal, v. 26, p: 154-157). In studies carried out by Coley, it is described the successful use of *Streptococcus* together with *Serratia marcescens* (Coley Toxin) in the treatment of soft tissue sarcoma, noting also that such immunotherapy was not as effective in treating other cancers, such as melanomas and carcinomas. As these studies were conducted more than a century ago and have been relatively neglected by modern medicine (very focused on getting a single drug for diseases) its main concepts and possibilities have not been explored and clarified. Coley only used two bacterial components in its composition, and not did not exploit the utilization process and all possible modulations of the immune system as described herein. Hayashi et al were able to further advance the understanding of the importance of the immune system and also combined two antigenic components, but these concepts have not yet been explored in its entirety. In this work, Hayashi et al evaluated the effect of the importance of the lymph nodes in the treatment of patients with ovarian cancer with cell wall skeleton of *Mycobacterium bovis* associated with *Bacillus* Calmette-Guérin (BCG-CWS) ((Hayashi A, Nishida Y, Yoshii S, Kim S Y, Uda H, Hamasaki T (2009). "Immunotherapy of ovarian cancer with cell wall skeleton of *Mycobacterium bovis Bacillus* Calmette-Guérin: Effect of lymphadenectomy". Cancer Sei, vol. 100, no 10, p: 1991-1995). After surgical removal of tumors, patients received 2-200 μg intracutaneous doses of BCG-CWS. The vaccine was used in the study due to its potential to induce (IFN)-y and stimulate Langerhans cells (subsequently differentiated to dendritic cells) as reported in previous tests. The prognosis of patients after surgery without having undergone lymphadenectomy was considerably better than those who had it, which confirms the importance of the lymph nodes in obtaining immune responses against ovarian cancer in response to immunotherapy with BCG-CWS. Although two distinct antigenic components were used, nonspecific to the disease being treated, they originated in only two bacteria, not showing in its composition other pathogen-associated molecular patterns such as those found in viruses, parasites, fungi and yeasts.

According to the existing knowledge in the art, there is the vital role of the immune system to fight disease, but few technologies have been able to effectively stimulate and immune-modulate this system to better fight the disease when it is already established.

Moreover, it is noteworthy that the healing of infections and neoplasms, contrary to what is preached and accepted nowadays, is always held by the immune system. Antibiotics, antimicrobial and anticancer drugs act primarily as an important facilitator and often essential for the healing of infections. In other words, antibiotics do not achieve cure the disease by themselves, but assist and facilitate the healing process carried out by the immune system. Antibiotics act in this sense, as a shifter of the biological balance in favor of the infected organism, to inhibit or kill, or destroy a portion of the bacteria "in vivo", through its specific action, allowing for faster and effective action of the immune system. However, there is no in vivo work demonstrating the elimination of microorganisms by the action of antimicrobials.

Under this new scientific assumption, it is necessary to develop immunomodulatory agents, immunogenic compositions and methods of treatment able to select agents that allow the induction of an innate immune response, in real-time, that will recontextualize, reprogram, and renew the immune system to a new specific adaptive response effective for the disease to be treated, through the proper presentation of pathogenic antigens to APC cells, which via memory and virgin cells of the immune system, will effectively combat infectious diseases and other diseases present in a given patient. That is, without the need for the generation and administration of a specific antigen for an established disease, using the respective mechanisms of the immune system, after its recontextualization, reprogramming, renewal, optimally induced by immunomodulatory agents, with immune responses reaching the speed and effectiveness equivalent to immune responses triggered by repeated invasions of the same pathogen previously memorized by the immune system.

That is, the new immunomodulatory agents, immunogenic compositions and methods of treatment would shift the balance of biological and antimicrobial chemotherapy in all malignancies, infections and infestations. This new therapeutic approach would combine the concurrent use of immunotherapy with traditional antibiotics, and in the infectious processes of any kind and in parasitic infections, increasing the chances of cure, and which can drastically reduce the morbidity and mortality from these diseases compared with therapies that take into account only the function of antimicrobial agents and chemotherapy alone.

OBJECTIVES OF THE INVENTION

It is an object of the present invention to provide immunogenic compositions for modulating the immune system comprising a therapeutically effective amount of two or more immunoactive antigenic agents that present pathogen-associated molecular patterns (PAMPS) and/or danger associated molecular patterns (DAMPS), one or more physiologically acceptable carriers, excipients, diluents or solvents.

In particular, it is an object of the present invention to provide immunogenic compositions for modulating the immune system which comprise antigenic agents that have immune-active pathogen-associated molecular patterns (PAMPS) and/or danger associated molecular patterns (DAMPS) selected from the group consisting of: A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

Another object of the invention is to provide the use of said immunological compositions for the manufacture of medicines for prevention and/or treatment of infectious diseases, autoimmune diseases, allergic diseases, inflammation, arthritis, inflammatory diseases, transplant rejection, diseases caused by vascular disturbances, diseases caused by hemorrhagic or ischemic cardiovascular events, ischemia, infarction and hemorrhage leading to tissue destruction, cardiac, renal, respiratory or liver disease, cancer, tumors and malignant and benign lesions.

The present invention also aims to provide methods for preventing or treating infectious diseases, autoimmune diseases, allergic diseases, inflammation, arthritis, inflammatory diseases, transplant rejection, diseases caused by vascular disturbances, diseases caused by hemorrhagic or ischemic cardiovascular events, ischemia, infarction and hemorrhage leading to tissue destruction, cardiac, renal, respiratory or liver disease, cancer, tumors and malignant and benign lesions., in animals, more particularly in humans.

The present invention also aims to provide methods to induce cellular repair, tissue regeneration, organ regeneration and regeneration of organic systems such as the circulatory system, nervous system and endocrine system.

Finally, the present invention aims to provide methods for the renewal of the immune response in an animal, particularly in humans.

DEFINITIONS

In the context of this patent application, abbreviations are used several times, and their definitions, according to their usage in this application, are summarized below:

BCG refers to attenuated *Mycobacterium bovis*, Bacille Calmette-Guerin;
DAMPS refers to danger associated molecular patterns;
DECA refers to the composition described in Example 1 of the present patent application;
GM-CSF refers to "Granulocyte macrophage colony-stimulating factor";
IL12 refers to Interleukin-12;
IL15 refers to Interleukin-15;
IL2 refers to Interleukin-2;
IL21 refers to Interleukin-21;
IL4 refers to Interleukin-4;
IL5 refers to Interleukin-5;
IL7 refers to Interleukin-7;
PAMPS refers to pathogen-associated molecular patterns.
PFU: plaque forming units.
PPD refers to purified protein derivative of *M. tuberculosis;*
PPD refers to the fraction of the purified protein extract culture of Koch's *bacillus* ("Purified Protein Derivative"). The PPD is the major antigen of *Mycobacterium tuberculosis;*
TDCI50 is a unit for quantification of viral particles and is the infectious dose in 50% of cells in a tissue culture;
Koch's Tuberculin refers to inactivated *Mycobacterium bovis* lysate;
Units Lf or "Limes flocculation units" is the international unit for quantifying antigens in toxoid vaccines accepted by the World Health Organization;

DESCRIPTION OF THE FIGURES

The following figures are part of this report and are included here to illustrate certain aspects of the invention. The object of the present invention may be better understood by reference to one or more of these figures in combination with the detailed description of the preferred embodiment presented here.

DETAILED DESCRIPTION OF THE INVENTION

Description of the Immunogenic Compositions

Figure 1:
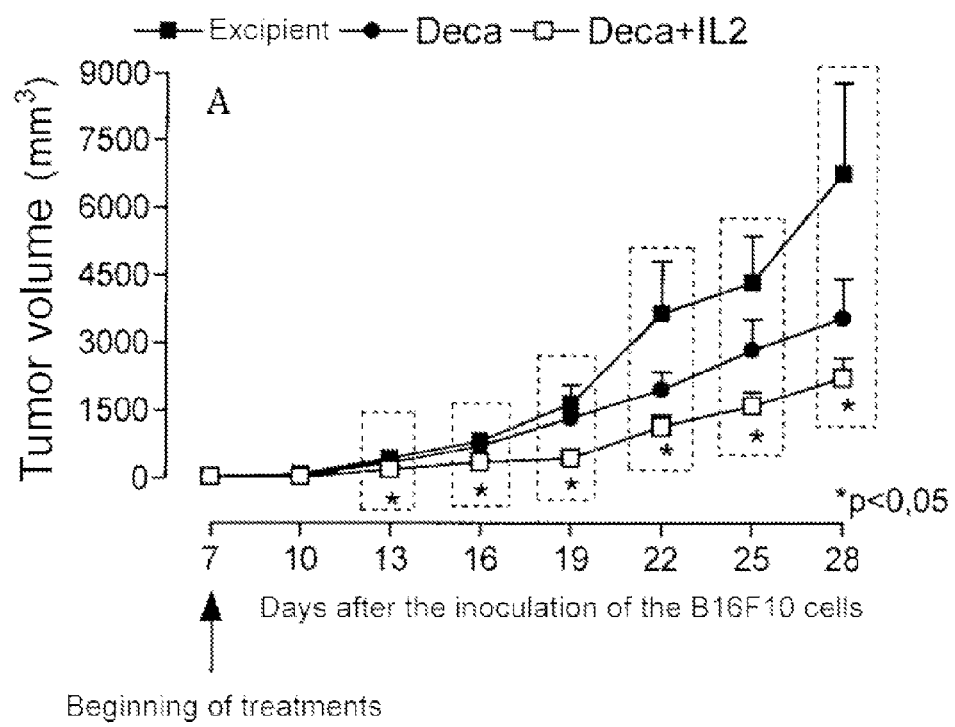
FIG. 1 shows the effect of treatment with DECA, DECA+ IL-2 on tumor growth in vivo. Murine melanoma cells (B16F10) were inoculated on day zero ($1\times10^6$, 100 μL/animal), subcutaneously (s.c.) on the back of C57B16 male mice. The (A) tumor volume (in $mm^3$) was measured every three days with the aid of a digital caliper. The (B) calculated percentage increase in the volume of each tumor obtained on the 7th day. The results were expressed as Mean±Standard Error of Mean (SEM). * $p<0.05$ represents a statistically significant difference as compared to the control group (one-way ANOVA, post-hoc: Dunnett test). n=9-10 animals.
Figure 1:
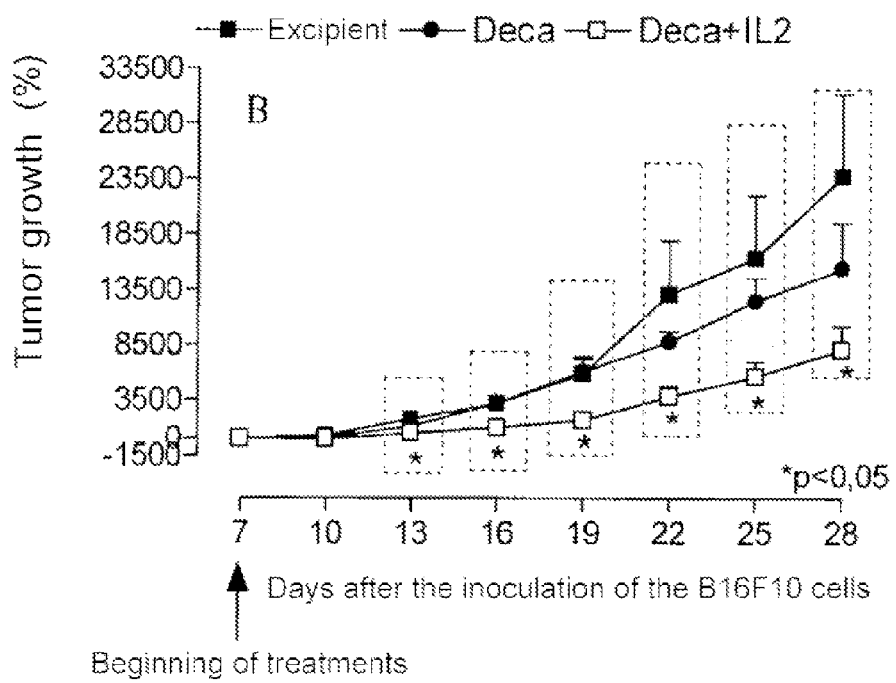

The present invention relates to immunogenic compositions for modulating the immune system comprising a therapeutically effective amount of two or more antigenic immunoactive agents presenting pathogen-associated molecular patterns (PAMPS) and/or danger associated molecular patterns (DAMPS) and one or more physiologically acceptable carriers, excipients, diluents or solvents.

Preferably the compositions of the present invention comprise immunoactive antigenic agents presenting pathogen-associated molecular patterns (PAMPS) and/or danger associated molecular patterns (DAMPS) selected from the group consisting of: (A) antigenic agents with molecular patterns associated with bacteria; (B) antigenic agents with molecular patterns associated with viruses; (C) antigenic agents with molecular patterns associated with fungi and yeasts; (D) antigenic agents with molecular patterns associated with protozoa; (E) antigenic agents with molecular patterns associated with multicellular parasites/or (F) antigenic agents with molecular patterns associated with prions.

Still more preferably the compositions of this invention include pathogen-associated molecular patterns (PAMPS) and/or danger associated molecular patterns (DAMPS) selected from among at least three categories (A), (B), (C), (D), (E) and (F) described above.

Still more preferably the compositions of this invention include pathogen-associated molecular patterns (PAMPS) and/or danger associated molecular patterns (DAMPS) selected from among at least four categories (A), (B), (C), (D), (E) and (F) described above.

Antigenic agents of the present invention can be selected from epitopes, genetic materials, lipids, polysaccharides and/or immunoactive proteins of the present invention can be obtained by purification from isolated fragments of material existing in nature or fractions derived from plant, animal or microbiological extracts, or produced by genetic recombination, preferably derived from viral, fungal, parasitic or bacterial prion strains.

Thus, the antigenic agents of the present invention with molecular patterns associated with bacteria of the present invention may be selected from, but not limited to antigenic agents with molecular patterns associated with bacteria of the genera *Staphylococcus, Streptococcus, Enterococcus, Corynebacterium, Bacillus, Listeria, Clostridium, Mycobacterium, Actinomyces, Nocardia, Escherichia, Proteus, Klebsiella, Serratia, Enterobacter, Salmonella, Shigella, Pseudomonas, Burkholderia, Stenotrophomonas, Acinetobacter, Vibrio, Campylobacter, Helicobacter, Bacteroides, Neisseria, Moraxella, Haemophilus, Bordetella, Brucella, Francisella, Pasteurella, Yersinia, Legionella, Gardnerella, Treponema, Leptospira, Borrelia, Mycoplasma, Rickettsial* and *Chlamydia*.

Antigenic agents with molecular patterns associated with virus of the present invention may be selected from, but not limited to antigenic agents with molecular patterns associated with virus families Adenoviridae, Arenaviridae, Bunyaviridae, Coronaviridae, Filoviridae, Flaviviridae, Hepadnaviridae, Deltavirus, Caliciviridae, Herpesviridae, Orthomyxoviridae, Papovaviridae, Paramyxoviridae, Parvoviridae, Picornaviridae, Poxyviridae, Reoviridae, Retroviridae, Rhabdoviridae and Togaviridae.

Antigenic agents with molecular patterns associated with fungi and yeasts of the present invention may be selected from, but not limited to antigenic agents with molecular patterns associated with fungi and yeasts of the genus *Sporothrix, Aspergillus, Blastomyces, Candida, Coccidioides, Cryptococcus, Histoplasma* and *Pneumocystis*.

Antigenic agents with molecular patterns associated with protozoa of the present invention may be selected from, but not limited to antigenic agents with molecular patterns associated with protozoa of the genera *Cryptosporidium, Ciclospora, Entamoeba, Naegleria, Giardia, Leishmania, Plasmodium, Toxoplasma, Trichomonas, Trypanosoma, microsporidia* and *Isospora*.

Antigenic agents with molecular patterns associated with multicellular parasites of the present invention may be selected from, but not limited to antigenic agents with molecular patterns associated with multicellular parasites trematodes, cestodes and nematodes.

The antigenic agents of the present invention comprise protein, polysaccharide, lipid molecules and/or composite synthetic molecules that mimic protein, polysaccharide and/or lipid molecules.

More specifically the agents of the invention comprise immunoactive antigenic protein molecules which have enzyme activity, for example kinases, phosphatases, streptoquinases, estreptodornases and Deoxyribonucleases (e.g. dornases).

The immunogenic compositions for modulating the immune system of the present invention comprise from 0.001 to 500 micrograms per ml of each immunogenic agent.

Such immunogenic agents can be encapsulated in capsules, microparticles, nanoparticles, coated tablets, liposomes.

Specifically, the immunogenic compositions for modulating the immune system of the present invention comprise from 4 to 20 antigenic agents selected from the group consisting of antigens derived from agents: dornase, yeast extract, oidiomycin, PPD, prions, streptoquinase, *Streptococcus* toxoid, diphtheria toxoid, Tetanus toxoid, Koch's tuberculin, inactivated lysate of *Ascaris lumbricoides, Aspergillus* spp., *Aspergillus flavus, Aspergillus fumigatus, Aspergillus terreus, Candida* spp., *Candida albicans, Candida glabrata, Candida parapsilosis, Chlamydia* spp., *Chlamydia pneumoniae, Chlamydia psittaci, Chlamydia trachomatis, Cryptosporidium* spp., *Dermatophytes, Entamoeba hystolitica, Enterobius vermicularis, Enterococcus faecalis, Epidermophyton floccosum, Escherichia coli, Giardia lamblia, Haemophilus influenzae, Microsporum cannis, Mycobacterium* spp., *Mycobacterium bovis, Mycobacterium leprae, Mycobacterium tuberculosis, Neisseria gonorrhoeae*, human papilloma virus, Polio virus, *Proteus* spp., *Proteus mirabilis, Proteus penerii, Proteus vulgaris, Salmonella* spp., *Salmonella bongori, Salmonella enterica, Serratia* spp., *Serratia liquefaciens, Serratia marcescens, Shigella* spp. *Shigella flexneri, Shigella sonnei, Staphylococcus* spp., *Staphylococcus aureus, Staphylococcus epidermidis, Strongyloides stercoralis, Streptococcus* spp., *Streptococcus bovis, Streptococcus viridans, Streptococcus equinus, Streptococcus pneumoniae, Streptococcus pyogenes, Toxoplasma gondii, Trichomonas vaginalis*, trichophytin, *Trichophyton* spp., *Trichophyton rubrum, Trichophyton tonsurans, Trichophyton mentagrophytes*, yellow fever virus, hepatitis B virus, rubella virus, varicella zoster virus, variola virus, mumps virus, measles virus, herpes virus and vaccinia virus or synthetic analogues that present pathogen-associated molecular patterns (PAMPS) and/or danger-associated molecular patterns (DAMPS) associated with these antigenic agents.

A preferred immunogenic composition of the invention comprises inactivated *Mycobacterium bovis* lysate, purified protein derivative of *M. tuberculosis*, inactivated *Staphylococcus aureus* lysate, inactivated *Staphylococcus epidermidis* lysate, inactivated *Streptococcus pyogenes* lysate, inactivated *Streptococcus pneumoniae* lysate, inactivated *Enterococcus faecalis* lysate, Streptokinase/dornase, inactivated *Candida albicans* lysate, inactivated *Candida glabrata* lysate, inactivated *Epidermophyton floccosum* lysate, inactivated *Microsporum cannis* lysate, inactivated *Trichophyton mentagrophytes* of the *interdigitale* variety lysate, inactivated enteropathogenic *Escherichia coli* lysate, inactivated *Salmonella bongori* lysate, inactivated *Salmonella enterica* lysate and inactivated *Salmonella subterranea* lysate.

A preferred immunogenic composition of the invention comprising from 0.001 to 1 ng/ml of inactivated *Mycobacterium bovis* lysate, 0.001 to 1 ng/ml of purified protein derivative of *M. tuberculosis*, 0.1 to 100 µg/ml of inactivated *Staphylococcus aureus* lysate, 0.1 to 100 µg/ml of inactivated *Staphylococcus epidermidis* lysate; 0.1 to 100 µg/ml of inactivated *Streptococcus pyogenes* lysate; 0.1 to 100 µg/ml of inactivated *Streptococcus pneumoniae* lysate; 0.1 to 100 µg/ml of inactivated *Enterococcus faecalis* lysate, 0.01 to 10 µg/ml of streptokinase, 0.01 to 10 µg/ml of dornase; 0.1 to 100 µg/ml of inactivated *Candida albicans* lysate; 0.1 to 100 µg/ml of inactivated *Candida glabrata* lysate, 0.1 to 100 µg/ml of inactivated *Epidermophyton floccosum* lysate; 0.1 to 100 µg/ml of inactivated *Microsporum cannis* lysate, 0.1 to 100 µg/ml of inactivated *Trichophyton mentagrophytes* of the *interdigitale* variety lysate; 0.1 to 100 µg/ml of inactivated enteropathogenic *Escherichia coli* lysate; 0.1 to 100 µg/ml inactivated *Salmonella bongori* lysate, 0.1 to 100 µg/ml inactivated *Salmonella enterica* lysate and 0.1 to 100 µg/ml of inactivated *Salmonella subterranea* lysate.

Additionally, in order to raise, lower or polarize the immune response depending of the goal of the immunotherapy, the antigenic composition of the present invention may comprise cytokines and/or chemokines such as GM-CSF, IL4, IL5, IL7, IL12, IL15, IL21, interferon gamma, and most preferably IL2.

The compositions of the present invention can further comprise excipients, such as bactericides, bacteriostats, antioxidants, preservatives, buffers, stabilizers, pH adjusters, osmolarity adjusters, antifoaming agents and surfactants, and residual antigen inactivating or fractionation agents, growth medium components and solvents commonly used in the production of vaccines and immunotherapies.

The compositions of the present invention may be a solid, liquid or gel. As used herein, the use of the term "pharmaceutically acceptable carrier" means a non-toxic solid, inert, semi-solid liquid excipient, diluent, auxiliary formulation of any type, or simply a sterile aqueous solution such as saline. Some examples of materials which can serve as pharmaceutically acceptable carriers are sugars such as lactose, glucose and sucrose, starches such as corn starch and potato starch, cellulose and its derivatives such as sodium carboxymethyl cellulose, a ethyl cellulose and cellulose acetate, cyclodextrin; oils such as peanut oil, cottonseed oil, sunflower oil, sesame oil, olive oil, corn oil and soya bean oil, glycols such as propylene glycol, polyols, such as glycerol, sorbitol, mannitol and polyethylene esters such as ethyl laurate, ethyl oleate, agar, buffering agents such as aluminum hydroxide and magnesium hydroxide, alginic acid, pyrogen-free water, isotonic saline, Ringer's solution, buffer solutions of ethyl alcohol and phosphate as well as other non-toxic compatible substances used in pharmaceutical formulations.

A variety of administration routes in animals or humans for the immunotherapeutic compositions and vaccines described herein are available. The particular selected mode will depend on the selected antigenic agents, the dosage required for therapeutic efficacy and patient to whom the composition is administered. The methods of the present invention can generally be practiced using any mode of administration biologically acceptable, i.e., any means that produces effective levels of immune response without causing clinically adverse reactions. Such modes of administration include intradermal, oral, rectal, sublingual, topical, nasal, transdermal or parenteral administration. The term "parenteral" includes subcutaneous, intravenous, epidural, irrigation, intramuscular, release pumps or infusion. In particular, in this invention, oral, intradermal, parenteral, subcutaneous, intravenous, intramuscular, and, by the nasal mucosa and/or oral administration are preferred for administration of the compositions claimed herein.

For parenteral administration, the active ingredients may also be dissolved in a pharmaceutical carrier and administered as a solution, emulsion, including micro- and nano-emulsions or suspension. Examples of suitable carriers are water, saline, dextrose solutions, fructose solutions or oils of animal, vegetable or synthetic origin. Other vehicles may also contain other ingredients, for example, preservatives, suspending agents, solubilizing agents, buffers and the like.

Properties of the Immunogenic Compositions of the Present Invention

The immunogenic compositions of the present invention have an unexpected effect on the immune response. As can be seen in the Examples below, the immunogenic compositions of the present invention show an unexpected technical effect of causing an immune response that involves recontextualizing, renewal and reprogramming of the immune response in real time.

More specifically, the immunotherapeutic compositions of the present invention are capable of provoking a recontextualization of the operational action capacity of the immune system by changing the relationship of forces against the aggressors in its favor, giving the immune system a competitive advantage, which does not occur spontaneously in the evolution of disease. This recontextualization determines a consequent renewal and reprogramming of the established immune response or incipiently established, or erroneously established mistakenly attacking in a dysautonomical way the human or animal body, polarizing it into a primary or secondary, active or inhibitory, more effective appropriate immune response.

This effect occurs via stimulation, activation and joint action of certain components of the immune system, such as sentinel cells, antigen presenting sentinel cells, and memory lymphocytes. Specifically, the compositions of this invention properly activate sentinel cells, dendritic cells and other APC cells, generating the degree and intensity of CD4 T cell activation and the degree and intensity of the immune profile to fight the infection, infestation or neoplastic disease.

Accordingly, the immunomodulatory antigenic compositions of the present invention, when in larger or significant amounts trigger a specific active adaptive immune response, desired to combat bacterial, viral or parasitic infections, in combating neoplasms, cancer and tumors.

In addition, the treatment with the immunogenic compositions of the present invention is capable of stimulating the regenerative power of the immune system, providing a subsequent effect to the elimination of infectious disease and other diseases: to recover cells and tissues, by restoring organ function debilitated from trauma and damage which cause the loss of part of the organism.

Thus, the immunogenic compositions of the present invention are able to mobilize the immune system and lead to an increased regenerative power of the body, through mobilization of stem cells or the activation of gene sets which allow the regeneration of cells and tissues and can even reconstruct organs and their functions, and can reconstitute organic systems such as the vascular system, the nervous system and the endocrine system, among others.

As can be seen in the Examples presented below, the immunogenic compositions of the present invention exhibit an unexpected technical effect of recontextualizing, renewing, and reprogramming the immune response in real time and consequently significant cure rates when compared to drugs and methodologies in the art.

In a first embodiment of the invention, a particular concentration of immuno-modulator agent(s) is used for preparing an immunotherapy pharmaceutical composition capable of inducing an innate immune response, which triggers a cascade of immune events, including the activation of memory lymphocytes from the agent(s) inoculated by human intervention and the concomitant activation by antigens present in the patient's own body, resulting in a recontextualization, renewal and reprogramming of the ongoing immune response to a particular established disease (or still in the establishment phase), generating an adaptive response specific to this disease effectively, allowing the pathogen to be combated. As such, the administration of the composition containing the agents of the present invention repolarizes or improves the polarization of the immune system in the presence of a disease when the hitherto established polarization is inadequate, by the action of the etiologic agent or colonizer. The activities of the agents of the present invention affect the shape, time, accuracy and polarization of the immune response, preferably leading to an specific innate and/or adaptive response that it is more effective to combat the disease, leading to a better reaction of organism itself.

The present invention provides a way to combat these types of heterologous (infections and infestations) and autologous (neoplasms) attacks through the use of the antigenic combinations described. The present invention also provides for the possibility of adding traditional therapies to the agents of this invention, aiding the process of elimination of the etiological heterologous invading agents and of the colonizing autologous cells, through the real therapeutic potential of antimicrobial, anticancer and other drugs, selective for the pathogens and other infectious agents. This is made possible by the principle of displacement of the biological equilibrium in favor of the patient in combination with a correct polarization of the immune response as described herein.

When the immune stimulation follows a situation of immune response, after the termination of the disease mechanism or aggression, the continued activation of the immune system by antigens or immunomodulatory agents of the present invention leads, through the activation of stem cells, to the regeneration of tissues, organs and systems, by mechanisms not yet fully understood, but related to healing or restitutio ad integrum mechanisms observed in various medical situations.

The compositions of the present invention allow the recruiting of the maximum number of virgin and memory cells of the individual, producing more significant effects than an antibody increase as described in the prior art. The use of multiple antigenic agents with distinct enough PAMPS and DAMPS to simulate different types of attacks that the organism suffers and to which the organism has already immunologic memory of, be it by environmental exposure or vaccination programs, allows a wider recruitment of memory and virgin cells, enabling real-time recontextualization of the immune response and thus potentially and radically altering the type of immune response and disease or illness progression that affects the individual in a positive, and in several cases, such amazing way as compared to the prior art. Furthermore, the present invention, unlike the prior art, applies a greater amount of bacterial components, having representatives of both intracellular and extracellular bacteria in the composition, besides components of viruses, parasites, fungi and yeasts. Hayashi et al have not explored more diverse compositions to obtain a potentially greater effect. The application process of the antigenic agents was also different, since the present invention encompasses more areas of the body and tissues that have APC cells, and preferably looks for exposure on locations close to the infection sites and other distal applications to the disease sites (as is the case in disorders or diseases that manifest themselves in specific locations of the body). The compositions of the present invention, when applied according to the process of using the present invention in one or, usually, at various strategic of body regions drained by lymphoid territories or primary and/or secondary lymphoid organs, or even intralesional, are perceived by the PRRs (pathogen-associated pattern recognition receptors) off all sentinel cells of the body.

In a first group of aggressive conditions or real danger, in which the immune system is being extemporaneously overwhelmed, paralyzed or overcome by bacteria, fungi, viruses, prions, parasites or other micro- or macro-organisms, uni- or multicellular, (heterologous aggression) or a benign or malignant neoplasm (autologous aggression), the modification of its preparation is given in the state of activation and mobilization of its cellular and molecular apparatus of the innate and adaptive immunity, which integrated are able to reverse the situation of competitive disadvantage in which the immune system and the body are found.

In a second group of aggressive conditions where the real danger comes from the immune system itself, i.e. when it's attacking the human or animal body, in an autoimmune or allergic disease, recontextualizing the immune system occurs as a preparation to be able to inhibit this detrimental action. The present invention induces the immune system to suppress its activation state and demobilize memory effector loops that maintain the self aggression. This effect is achieved by mobilizing the cellular and molecular apparatus of innate and adaptive immunity responsible for the suppression and regulation of immune response and a return to equilibrium known as homeostasis or normality.

In a third group of conditions where the immune system deals with the aftermath of tissue, organic or systemic attacks derived from multiple causes, heterologous or autologous, or even traumatic, the action of the immune system occurs in repairing the damage caused by these attacks. In this case, the preparation or mobilization of the immune system is through the mobilization of stem cells from the immune system itself or from other cellular systems, autologous, allogeneic or heterologous. Or even by activation of gene sets present in the patient's own cells.

Thus, the present invention employs immunomodulatory agents in amounts, concentrations and specific locations to recontextualize the immune system, activating and redirecting the mechanisms for tissue repair and regeneration, as occurs during cicatrization and regeneration of tissue, organ or system, leading to a "restitutio ad integrum" or reconstitution with scar. This repair is usually triggered at the end of an immune response process, after the healing a trauma, an infection, a tumor disease or an autoimmune or allergic reaction.

Use of the Immunogenic Compositions of the Present Invention.

Considering the properties of the immunogenic compositions of the present invention, it constitutes another aspect of the present invention using the immunogenic compositions in the manufacture of medicaments for the prevention and/or treatment of infectious diseases, autoimmune diseases, allergic diseases, inflammation, arthritis, inflammatory diseases, transplant rejections, diseases caused by vascular disorders, diseases caused by hemorrhagic or ischemic cardiovascular events, ischemia, infarction and hemorrhage leading to tissue destruction, cardiac, renal, respiratory or liver disease, cancer, tumors and malignant and benign lesions.

The immunogenic compositions of the present invention are also directly used in the prevention and/or treatment of infectious diseases, autoimmune diseases, allergic diseases, inflammation, arthritis, inflammatory diseases, transplant rejection, diseases caused by vascular disorders, diseases caused by hemorrhagic or ischemic cardiovascular events, ischemia, infarction and hemorrhage leading to tissue destruction, cardiac, renal, respiratory or liver disease, cancer, tumors and malignant and benign lesions.

These infectious diseases can be of viral, bacterial, fungal or parasitic origin.

Diseases of viral origin prevented and/or treated by the immunogenic compositions of the present invention can be caused by the following viruses but not limited to:

HIV, hepatitis virus, herpes virus, rhabdovirus, rubella virus, smallpox virus, poxvirus, and Morbillivirus paramyxovirus.

Diseases of bacterial origin prevented and/or treated by the immunogenic compositions of the present invention may be caused by the following bacteria, but not limited to, *Pneumococcus, Staphylococcus, Bacillus, Streptococcus, Meningococcus, Gonococcus, Escherichia, Klebsiella, Proteus, Pseudomonas, Salmonella, Shigella, Haemophilus, Yersinia, Listeria, Corynebacterium, Vibrio, Clostridia, Chlamydia, Mycobacterium, Treponema*, and *Helicobacter*.

Fungal diseases prevented and/or treated by the immunogenic compositions of the present invention may be caused by the following fungi but not limited to: *Candida, Aspergillus, Cryptococcus neoformans*, and/or fungi that cause superficial and deep mycosis. Diseases caused by parasites are caused by the following parasites: *Trypanosoma, Schistosoma, Leishmania*, amoebas and tapeworm.

The immunogenic compositions of the present invention are also used in the prevention and/or treatment of erythematosus and located lupus, rheumatoid arthritis, polyarteritis nodosa, polymyositis and progressive dematomiosite, progressive systemic sclerosis, diffuse scleroderma, glomerulonephritis, myasthenia gravis, Sjogren's syndrome, Hashimoto's disease, Graves disease, adrenalitis, hypoparathyroidism, pernicious anemia, diabetes, multiple sclerosis, demyelinating diseases, uveitis, pemphigus, pemphigoid cirrhosis, ulcerative colitis, myocarditis, regional enteritis, respiratory distress syndrome in adults, and local manifestations of the reaction to drugs, atopic dermatitis, infantile eczema, contact dermatitis, psoriasis, lichen planus, allergic enteropathies, bronchial asthma, transplant rejection, post streptococcal diseases such as cardiac, renal and articular rheumatic fever manifestations and other related manifestations, multiple and various forms of cancers, such as carcinomas, adenocarcinomas, melanomas, sarcomas, malignant astrocytomas, hepatomas, hypernephroma, lymphomas and melanomas, among others.

The immunotherapeutic compositions of the present invention are also useful in the treatment of cancer, autologous colonization by benign and malignant tumor cells, in all forms of cancer known as as carcinomas, adenomas, adenocarcinoma, hepatoma, astrocytomas and other neoplasms of the central and peripheral nervous system, melanomas, sarcomas, lymphomas and leukemias and all benign tumors.

The immunotherapeutic compositions of this invention may also be useful for diseases arising in a dysautonomia of the immune system (as already mentioned) such as lupus erythematosus; rheumatoid arthritis; polyarteritis nodosa, polymyositis and dermatomyositis and progressive systemic sclerosis (diffuse scleroderma); glomerulonephritis, myasthenia gravis, Sjogren's syndrome, Hashimoto's disease (hypothyroidism), Graves disease (hyperthyroidism); adrenalites; hypoparathyroidism, pernicious anemia, diabetes, multiple sclerosis, and demineralizing co-related or related diseases; uveitis; pemphigus, pemphigoid cirrhosis; ulcerative colitis; myocarditis; regional enteritis, hepatitis and cirrhosis; adult respiratory distress syndrome, local and systemic manifestations of drug reactions, such as pharmacodermia, dermatitis, among others.

Still in the field of dysautonomia diseases of the immune system, the present invention also provides immunotherapy treatments of arterial and venous vascular accidents, in diseases such as myocardial infarction, thromboembolic phenomena in the lung, brain and digestive system, or in any other area of the body where stroke or ischemia leads to hemorrhage, which results in necrosis or atrophy of these segments, such as, but not limited to, in the whole musculoskeletal system, in the whole central and peripheral nervous system, that lead to occlusion of the blood supply and results in heart attacks and brain injuries. Thus, the immunotherapy of the present invention provides an anti-inflammatory and immune enhancement that can lead to blockage of inflammatory processes important to the establishment of diseases such as metabolic syndrome, obesity, type 2 diabetes, atherosclerosis, alcoholic fatty liver, non-alcoholic fatty liver, hypertension, renal failure, post thrombotic syndrome, post-thrombophlebitis and any other disease derived from an inflammatory action of the immune system.

In case of allergic, autoimmune and inflammatory diseases the immunotherapy of the present invention can be useful, but not limited to, for inflammation associated with or caused by allergic reactions of the skin, atopic eczema in children; contact dermatitis in asthma, bronchial asthma, bronchiolitis and allergic bronchitis, allergic rhinitis, allergic enteritis; allergic enteropathy; inflammatory pseudo-tumor processes of currently unknown origin; psoriases (pseudo-inflammatory tumor); lichen planus, post-streptococcal diseases; heart, liver, lung, kidney, pancreatic islets transplant rejection and others; hypersensitivity or destructive immune responses against infectious agents, post-streptococcal disease, such as heart, kidney, myocarditis, pericarditis and rheumatic fever and equivalent by other etiologic agents, not limited by the forms of these manifestations. In the case of autoimmune and allergic diseases, concentrations and dosages are preferably much lower, acting on incomplete activation of immune cells, memory or not, which may include, but not limited to the aforementioned diseases.

The immunogenic compositions of the invention are also used to induce cell regeneration, tissue regeneration, organ regeneration and the regeneration of organic systems such as the circulatory system, nervous system and endocrine system.

Thus one embodiment of the invention is a method for inducing cellular repair, tissue regeneration, organ regeneration and regeneration of organic systems such as the circulatory system, nervous system and endocrine system in an animal comprising administering to the animal an effective amount of one or more immunogenic compositions of the present invention.

It is another embodiment of the present invention a method for the renewal of the immune response in an animal comprising the following steps:

a) administering systemically and/or locally to the animal a therapeutically effective amount of one or more immunogenic compositions as defined in any one of claims 1 to 21;

b) ensure contact of one or more immunogenic compositions, applied in step "a" with dendritic cells or other APC cells of the animal;

c) optionally administering prosthetic agents, such as vitamins in the site or region in which the disease is to be treated, in order to strengthen the metabolism and therefore the immune system of the animal, and optionally administering medications or other specific treatments.

In one embodiment of the invention, the compositions of the present invention are administered once, in one area of the body or in different sites in order to redirect the immune system with the highest possible efficiency. The use of the immunogenic compositions of the present invention for modulation of the immune system, involving the exposure of part or all of the system for recognition of antigens in the immune system, such as dendritic cells, macrophages and lymph nodes from different parts of the body will depend on the goal imposed by the illness being fought, and occurs preferentially through injections or use of guns, or delivery systems or controlled infusion or pulsed cells with in vitro antigens. The agent may be applied to only one location in the body or in several tens of locations in several forms: subcutaneous, muscular, intravenous, oral, breathable aerosol, cutaneous (dermal patches) in organs, the viscera, or specific tissues, or in different body cavities, which can vary in number from one to one hundred (100) applications in one to fifty (50) sessions.

The antigenic compositions of this invention may also be combined with other drugs that can weaken the reproduction, growth, or any other form of strengthening of the disease's causative agent, causing a shift of the equilibrium in favor of the biological immune defenses of the host, animal or human. Or still in concomitant treatment.

The antigenic compositions of this invention may also be combined with other procedures such as, but not limited to, antibiotics, chemotherapy, radiation therapy, therapy with antibodies and antisera, using hormones or other physiology modulating agents (cytokines, chemokines, neurohormones, peptides), treatment with antiviral agents, use of herbal medicines, vitamin supplementation, supplementation with other cofactors or prosthetic agents, transplantation of cells or tissues, methods of therapeutic or prophylactic vaccination (with or without cells and not limited to the type of vaccine vehicles), gene therapy, surgery or homeopathy, depending on the disease or illness being fought related to an improper or inefficient immune activity.

In particular, in order to raise, lower or polarize the immune response as the goal of immunotherapy, the antigenic compositions of this invention may be used in conjunction with therapy with cytokines and/or chemokines such as GM-CSF, IL4, IL5, IL7, IL12, IL15, IL21, interferon gamma, and most preferably IL-2.

Recontextualization, renewal and reprogramming of the immune response.

The recontextualizing of the immune system, as explained in the text of this patent application, is achieved by means of stimulation of the immune system by antigens of different pathogens not related to the pathology to be treated, for which the human or animal, preferably, already has an immunological memory of.

These varied and multiple antigens, in number greater than five, with multiple PAMPs and DAMPs, induce in the sentinel cells and in the APC cells, especially in dendritic cells, an intense activation allowing the mobilization of these memory CD4 lymphocytes specific for these antigens at the site of application.

These stimuli must be capable of causing an intense, strong and effective secondary specific immune response to these antigens at the site of application, in the regional lymph nodes, in the lymph nodes at a distance and a systemic mobilization of the immune system so that it can, in parallel, cause an effective response capable of eradicating the specific pathology in progress.

The innate and adaptive immune response caused intentionally by the composition of the present invention should encompass the full extent of the body area affected by the condition being treated and even exceed it if possible to be able to activate the sentinel and APC cells in the number and intensity that would be needed to properly address the aggression caused by the pathogenic disease to be treated, and activating and triggering the best specific adaptive response, effectively and properly sequentially polarized, in order to cure the condition being treated.

Thus the innate and adaptive response induced by the present invention will geographically overlap the condition being treated and by its intense and extensive activation will correct the inefficient activation, purposely limited by the action of the pathogen that overcomes the body's defenses, by preventing competition, its proper mobilization and development of an effective adaptive response according to its greatest genetic and biological potential. This ideal activation should also reverse the immunosuppression, the tolerance and escape mechanisms established by pathogens because it is known and proven that an unrelated strong and intense immune response, that fully covers the response to be corrected, through the activated cells and cytokines of the immune system, will correct these deficiency situations efficiently.

Effector cells and memories of specific antigens of the present invention, activated and generated at the site of application of the antigens, will, via the bloodstream, enter the already activated lymph nodes, which drain the region affected by the disease and will enable, in a strong and intense way, all the existing dendritic cells there. This way, they will lead to an activation of the entire lymph node, causing it to grow with increased irrigation, increasing its size and making it a reactional lymph node capable of provoking an immune response against weak antigens, which by themselves are not capable of causing an immune response. This adjuvant effect, well known and demonstrated experimentally and clinically, of the effector/memory T lymphocytes, will oppose the action of the target causative agent that is blocking the required activation of the lymph node for the development of an immune response that is necessary to combat the disease in question.

That, exclusively for the purpose and by the action of the present invention, through its potent antigenic composition, may occur that the sentinel cells and dendritic cells and macrophages of the immune response will be the same for unrelated antigens and to the pathological antigens, but from this action, will be intensely and properly activated. Dendritic cells strongly activated by multiple antigens, have a slow metabolism and ideally present all dominant and subdominant epitopes of the causative agent, by the known "helper" effect, mobilizing all possible and available T lymphocytes able to specifically recognize antigens of the autologous or heterologous pathogen, to be treated and to react against it.

That the areas of the inflammatory process and lymphatic territories are exactly the same. The inflamed area, through the anti-inflammatory action of specific memory cells, unrelated, mobilized by the present invention by their antigenic composition, will block the inflammasomes and exert an anti-inflammatory action that will correct the pathological inflammation responsible for the morbidity of the disease and which was caused by its etiological agent. For the memory effect it's important to note that this known action of the memory T cells is the major responsible for the fact that a second contact with any pathological agent, after an already established immunity, is asymptomatic, without causing a disease.

That the lymphatic territories are exactly the same, only now intensely activated and with the necessary alarm signal, caused by the present invention, to cause any immune response, even for a weak antigen, similar to what occurs with dendritic cells common to this invention and to the autologous or heterologous etiological agent to be fought. Lymphokines and innate cells that command an effective secondary response will be the same and the T lymphocytes specific against the etiologic agent to be fought, will "hitch a ride" on this ideal microenvironment for holding an effective immune response.

That the dendritic cells activated by the present invention, can capture the antigens of the etiological agent to be fought at the site of the pathology and in the related lymphatic territories and be in contact with the pathogen specific TCD4 lymphocytes, in a correctly and ideally enabled lymphatic system. The role of the dendritic cells activated and matured with the TCD4 specific to the etiologic agent, occurs in a microenvironment conducive to conducting an immune response, with all the genetic and biological potential of the host organism's immune system.

These dendritic cells at the site of the pathology and at the lymph nodes will properly gauge the severity, extent, intensity and type of aggression, activating, inducing, coordinating, polarizing, leading and maintaining a new effective adaptive immune response, whose effector loop, with the collaboration of the cells and effector molecules of the intense and properly activated innate immunity may be able to eliminate the causative agent to be fought. So the answer is reprogrammed and lead back as noted above, reversing the biological balance in favor of the host, which until then was under the yoke of the offending autologous or heterologous agent.

This action may occur with or without the help of biological balance shifters such as antibiotics and anticancer drugs, capable to block, weaken or neutralize the effects and potential of the etiological agent, allowing the immune system to have a chance to heal the pathology that is the target of the treatment. Once triggered by any etiological agent, the immune system will only stop responding when the etiological agent is eliminated or the organism passes away, this way the invention will help avoid the latter option, or it will improve the patient's condition if there is a chronic disease that cannot be cured.

Thus the action of the compositions of the present invention intentionally and strategically superimposed over the entire area under the action of the agent to be fought, will recontextualize the immune system by activating the PAMPs and DAMPs in the sentinel cells and common APCs and by the unrelated specific secondary adaptive immune response. This intentionally induced immune response will efficiently activate the whole lymphatic territory and the organic territory affected by the etiological agent. In the recontextualized area and in the bulge, and within the context of a greater immune response, stronger, more intense and more extensive secondary anti-inflammatory nature of the target immune response will be, as described, reprogrammed and efficiently renewed within the scope of a greater chance for the host, now with a chance of reversing the biological balance in its favor.

Adequacy of the protocol to the pathophysiological characteristics of the condition being treated:

a) The Basis of Immunotherapy Against Neoplasias.

The main characteristic feature of malignant neoplasms is the dominance of the microenvironment as defined in the study of the present invention, which differs from the traditionally defined in the current state of the art, which is that of the environment created by the action of tumor cells with the cells of the organism by which such action will make them function in their favor. The microenvironment defined herein is the space around a single or a set of neoplastic cells, which by means of surface molecules and/or other molecules secreted by it totally dominate this environment to its advantage.

In this dominated space the connective tissue starts to nurture and sustain these cells through its structural elements and through new vessels destined to supply the tumor cells and their supporting tissue. Through surface molecules and substances and enzymes secreted by the tumor cells in this environment, they destroy the tissue from which they originated, and healthy tissue invaded by them, which become colonized and replaced. Surface and secreted molecules completely block the immune system, inactivating and immobilizing sentinel, APC and lymphocytic cells, inducing nonspecific and specific immunosuppression and inactivating the locoregional and distant lymph nodes. Through the domination of the microenvironment the tumor cells, through surface molecules and enzymes, enter the blood and lymphatic vessels, and colonize distant locations away from the local primary tumor and cause distant lymphatic and hematogenous metastases.

Thus, the total domination of the microenvironment around a single cell makes a tumor cell, through its indiscriminate proliferation, to initially pathologically subjugate space around itself, its tissue of origin, the adjacent areas, the organ and finally through metastases the body as a whole.

Similarly, the immune ignorance, immunosuppression and the specific and nonspecific induced tolerances are primarily in situ, and then local, local-regional, organic and finally completely dominating the systemic immune system of the host body.

The dominance of the microenvironment is therefore the strategic, crucial and determinant effect produced by the genomic potential of a neoplastic cell, which leads one tumor cell to dominate the in situ, local, regional, organic and systemic space, colonizing the host and leading to death.

In short, an immunotherapy must necessarily break the dominance of the established tumor microenvironment and macroenvironment, and cover all the immunological territories dominated by the neoplasia. The immunotherapy treatment should also cover the lymph territories at a distance from the tumor, inducing a recontextualization, renewal and reprogramming of the immune system, from the outside to the inside the affected area with a strong inertia able to reverse completely, together with locoregional treatment (intratumoral and perilesional), the tumor dominance.

Immunoprophylaxis should be performed every 4 or 5 days, as it's the physiological period of the generation of suppressor cells that control the immune response. Successive waves of repeated antigenic stimulation in the meantime will indefinitely perennize the immune response, perpetuating the antigenic stimulus as it occurs with an infection before its chronicity phase and generation of an immune dysfunction. The failure to generate suppressor cells and the recontextualization prevents the domination of the suppressor cells by the tumor and its protection in opposition to the domination of the environment.

The action of a neoplastic cell in the field of the microenvironment and of a set of them in the macro environment is carried out 24 hours a day and during the entire period during which the condition exists. Therefore, immunotherapy with the abovementioned scope, frequency and magnitude should be applied continuously as long as there are still tumor cells. It is interesting to mention that the traditional immunotherapy that causes discontinuous stimuli, like the protocols for immunization with inert antigens (soluble or not) or with attenuated agents do not find application in the pathophysiological context induced by tumors.

Any specific immune response can be amplified and efficiently enhanced by the addition of cytokines and/or chemokines, preferably exogenous IL-2 at a receptor saturation level which will produce the proliferation of immune cells that recognize the antigen and, therefore, have on its surface the complete expression of the interleukin 2 receptor. Therefore, only the response of the antigens induced by the invention and induced by the causative agent (autologous or heterologous) will be amplified. In an antitumor immunotherapy in which there are only weak antigens, it should be supplemented with IL2 in order to obtain an effective and robust immune response.

The Foundations of Immunotherapy Against Septicemia, Sepsis and "Septic Shock"

Septicemia is defined as an extremely serious infection in which one or more bacteria or microorganisms, from their entry point, enter the bloodstream and start circulating in large numbers, getting established at distant points, colonizing tissues, organs, and in the most severe cases, can successively reach most of the body surface. Generally, when the microorganism load is too large, a large number of bacteria, with their toxic and metabolic products, with countless PAMPS and DAMPS, touching with all the also countless PRRs and RDPs of most of the body surface, while generating an extensive, intense and violent general inflammatory process, with the massive release of cytokines from the translation of all these signs.

The unfavorable evolution of septicemia leads to sepsis, through the massive release of proinflammatory cytokines such as TNFs, IL1, IL18, IL6 and others, causing an inflammatory collapse with hemodynamic characteristic alterations, such as hypotension, rapid pulse, which may culminate in septic shock, usually irreversible. Septicemia, sepsis are serious infections with high morbidity and mortality. In these severe infections the immune system, in turn, with its compromised operability by weaknesses and blockages induced by bacteria, starts to act so as to eliminate the bacteria at any cost, through the inflammatory Th17 tissue profile, increasing inflammation disproportionately and therefore harming the organism.

In this inflammatory tissue profile, the effector loops of innate immunity, controlled by the TCD4 lymphocytes, cause tissue damage and sometimes massive destruction, that compromise organs and tissues and that exacerbate infections, leading, for example, to respiratory failure, lung shock, and in ARDS (adult respiratory distress syndrome), also leading to renal failure and multiple organ failure.

Therefore, in septicemia, in sepsis and in septic shock there are two variables that should strategically be considered and should be the target of an immunotherapy, so it is successful. These two variables are the inflammation caused by the massive spread of countless bacteria in the whole body and its connection with the PRRs and DPPs and the polarization for the Th17 profile caused by the functional infeasibility of the Th1 and Th2 profiles. These variables are the cornerstone of severity, gravity, morbidity and mortality of these diseases.

Taking into account these two variables, for an immunotherapy to be effective in these infections, it should be applied to cover the entire body surface, including the greatest number of lymphatic territories to geographically overlap with the action of the pathogen or pathogens. It should also be applied to the injured areas and to the perilesional region so that together they can cause widespread recontextualization, that by its action can recover the integrity of the T loop and produce a wide, extensive and intensive, anti-inflammatory effect by effector/memory T cells generated within the application sites. It should, in parallel, through the recontextualization and reprogramming above described, polarize the TCD4 response of the Th17 inflammatory tissue profile for the humoral TH2 and cell TH1 profiles, further decreasing the generalized inflammation.

The loop amplification by IL2 should be very low, just enough to specifically amplify the repolarization of the immune response of the inflammatory profile to the immunity profile.

Thus, the recontextualizing and the reprogramming achieved by immunotherapy using the compositions of the present invention, by recovering immune cells through the anti-inflammatory action of non-related specific memory T lymphocytes, by the repolarization of the tissue inflammatory profile TH17 to elective and effective TH1 and TH2 immunity profiles, will redirect the immune response. This immune response, renewed in real time during the infectious process, in conjunction with a biological balance shifter, in the case of the use of various antimicrobial agents, have a chance to reverse the biological equilibrium at the end of the curve in which is very favorable for the microorganism, to be favorable to the host and now have a chance of solution.

Adequacy of the protocol to the "status" of the immune system in the pathology and in the patient being treated.

In the case of cancer and septicemia, by the own pathophysiological mechanisms, there is a breach of the integrity and functionality of the T loop with an inadequate polarization for a suppressing TREG profile in cancer and for an inflammatory tissue Th17 profile in septicemia with a nearly complete inoperability of the immune system overcome by disease. In these cases, as in the examples cited herein, the recontextualizing must reach the whole body to reverse all immunosuppression, tolerance and immune ignorance induced by the pathology, as well as to restore all operational and functional capacity of the immune system to have a reprogrammed and renewed effective immune response.

Rationale of the Therapeutic Protocol

The therapeutic protocol of the present invention designed to be applied in cases of cancer and septicemia must:

be applied in most strategic lymphatic regions of the body or infection. In the cases described herein, more than 10 lymphatic territories have been hit. It must be applied within the tumor, and infected and perilesional areas.

the immunotherapy formulation must contain at least 5 antigens so it contains PAMPs and DAMPs so as to be able to recontextualize the immune system.

the application area must overlap, cover, and overcome the whole extension of regions dominated by the tumor and infection.

the antigenic stimuli must be repeated every 4 or 5 days in order to avoid the generation of suppressor cells capable of aborting the new desired immune response or to suppress an achieved repolarization.

the treatment must be maintained in this manner until the elimination of the last neoplastic cell, or to the end of the infection, or to the healing of the wound, organ or system.

in practice, 1 to 3 ml of this immunotherapy must be applied to 10 or more lymphatic territories. This invention should be jointly applied in intra and extra lesion or tumor areas damaged by cancer or by infection.

In summary, the immunotherapy is "systemically" distributed in several (at least ten) lymphatic territories, peri- and intra-tumoral or lesion with a volume able to disrupt and destabilize the tumor from the domination of its micro and macro environment, or cover the area significantly affected by infection and inflammation, as well as to restore the microenvironment that is favorable to the immune response of the organism. It will be applied every 4 to 5 days with the use of low doses of exogenous interleukin-2, uninterruptedly during the period of duration of the disease. In the case of septicemia, sepsis, and septic shock as noted above this dose should be the lowest possible.

EXAMPLES

To allow a better understanding of the invention and clearly demonstrate the technical progress achieved, the results of the various tests conducted with respect to this invention are shown below as examples.

In Example 1 several preferred immunogenic compositions of the present invention are described. In Examples 2 to 8 the properties, usage, and therapeutic methods employing the immunogenic compositions of the present invention are shown. In Examples 2 to 8 the immunogenic composition described in Example 1, Composition 1 was used and herein referred to as DECA.

These Examples are presented for illustrative purposes only and should not be regarded in any way as limiting the scope and range of the invention.

Example 1

Immunogenic Compositions

In order to achieve the recontextualizing, renewal and reprogramming of the immune response in real time according to the innovative concepts described in the present invention, an expert skilled in the art can design different and distinct compositions, combinations or formulations of products, which fall within the scope of the invention.

As described, for such compositions to meet the technical requirements for the advantageous or unpublished results in combating a number of diseases and illnesses, they must have a high diversity of antigens from pathogens, so as to get the maximum synergistic effect in binding the PAMPs and DAMPs to their receptors and allowing the achievement of a high degree of activation of the innate immunity in the sentinel cells (with or without ATC function) thereby allowing the recontextualizing, renewal and reprogramming of the immune response in real time.

Such compositions should preferably use antigenic agents for which most people, because of previous contact, would have memory clones of in their immune system capable of inducing a broad anti-inflammatory action in parallel to recontextualization. For this, antigenic agents should preferably be selected that:
- correspond to the most common infections contracted by the individual from childhood to maturity (when the animal or the human being acquires its "repertoire of immunity").
- are used in immunization programs such as childhood vaccination programs against endemic and/or epidemic diseases.
- those from organisms of potentially pathogenic microflora, especially of the gastrointestinal tract, where the memory lymphocytes play an active dynamic barrier ensuring the survival of the individual.

Ideally each of the antigenic agents should be present in a concentration of 0.001 to 500 micrograms per mL.

In accordance with these concepts, several formulations have been developed, using antigenic agents in their already available, safe, and approved forms for use in human vaccination programs or allergic response tests and immunity assessment tests.

Therefore, we present the following several examples of compositions which fall within the scope of the present invention, without however the intention to limit it, since the present invention and its concepts allow for the design of immunogenic compositions comprising a very large number of combinations of antigenic agents.

Composition 1:

| Component | Concentration |
| --- | --- |
| Koch's Turberculin (inactivated *Mycobacterium bovis* lysate). | 0.004 ng/mL |
| PPD | 0.004 g/mL |
| Inactivated *Staphylococcus* lysate (*Staphylococcus aureus* and *Staphylococcus epidermidis* in equal parts). | 6.94 µg/mL |
| Inactivated *Steptococcus* lysate (*Streptococcus pyogenes*, *Streptococcus pneumoniae* and *Enterococcus faecalis* in equal parts). | 6.94 µg/ml |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Candida* lysate (*Candida albicans* and *Candida glabrata* in equal parts). | 6.94 µg/mL |
| Inactivated dermatophytes lysate (*Epidermophytonfloccosum, Microsporum cannis, Trichophyton mentagrophytes* of the interdigitale variety in equal parts). | 6.94 µg/mL |
| Inactivated enteropathogenic *Escherichia coli* lysate (EPEC) | 6.94 µg/mL |
| Inactivated *Salmonella* lysate (*Salmonella bongori, Salmonella enterica* and *Salmonella subterranea* in equal parts). | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 2:

| Component | Concentration |
| --- | --- |
| Koch's Turberculin (inactivated *Mycobacterium bovis* lysate). | 0.004 ng/mL |
| PPD | 0.004 g/mL |
| Inactivated *Staphylococcus aureus* lysate, inactivated *Staphylococcus epidermidis* lysate in equal parts. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Candida albincans* lysate, inactivated *Candida parapsilosis* lysate, inactivated *Candida glabrata* in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 3:

| Component | Concentration |
| --- | --- |
| PPD | 0.004 g/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 4:

| Component | Concentration |
| --- | --- |
| Inactivated BCG lysate | 50 mg/mL |
| Inactivated *Staphylococcus aureus* lysate, inactivated *Staphylococcus epidermidis* lysate in equal parts. | 6.94 µg/mL |

-continued

| Component | Concentration |
|---|---|
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated *Candida albincans* lysate, inactivated *Candida parapsilosis* lysate, inactivated *Candida glabrata* in equal parts. | 6.94 μg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 5:

| Component | Concentration |
|---|---|
| PPD | 0.004 g/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Apergillus fumigatus*, *Apergillus flavus*, and *Apergillus terreus* lysate in equal parts. | 6.94 μg/mL |
| Inactivated dermatophytes lysate (*Epidermophytonfloccosum*, *Microsporum cannis*, *Trichophyton mentagrophytes* of the interdigitale variety in equal parts). | 6.94 μg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 6:

| Component | Concentration |
|---|---|
| Koch's Turberculin (inactivated *Mycobacterium bovis* lysate). | 0.004 ng/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Neisseria meningitides* lysate. | 6.94 μg/mL |
| Inactivated *Apergillus fumigatus*, *Apergillus flavus*, and *Apergillus terreus* lysate in equal parts. | 6.94 μg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 7:

| Component | Concentration |
|---|---|
| Koch's Turberculin (inactivated *Mycobacterium bovis* lysate). | 0.004 ng/mL |
| Inactivated BCG lysate | 50 mg/mL |
| Inactivated *Staphylococcus aureus* lysate, inactivated *Staphylococcus epidermidis* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Candida albincans* lysate, inactivated *Candida parapsilosis* lysate, inactivated *Candida glabrata* in equal parts. | 6.94 μg/mL |
| Inactivated *Streptococcus equinus*, *Streptococcus bovis* and *Streptococcus viridans* lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Salmonella typhi*, *Salmonella paratyphi* and *Salmonella enterica* lysate in equal parts. | 6.94 μg/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 8:

| Component | Concentration |
|---|---|
| Koch's Turberculin (inactivated *Mycobacterium bovis* lysate). | 0.004 ng/mL |
| PPD | 0.004 g/mL |
| Inactivated *Staphylococcus aureus* lysate, inactivated *Staphylococcus epidermidis* lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Streptokinase derived from inactivated beta-hemolytic *Streptococcus* lysate purification. | 0.444 μg/mL |
| Dornase derived from inactivated beta-hemolytic *Streptococcus* lysate purification. | 0.111 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Helicobacter pylori* lysate. | 6.94 μg/mL |
| Tetanus toxoid | 50 units of Lf/m L |
| Inactivated *Candida albincans* lysate, inactivated *Candida parapsilosis* lysate, inactivated *Candida glabrata* in equal parts. | 6.94 μg/mL |
| Sodium Chloride | 7.5 mg/mL |
| Sodium phosphate dibasic heptahydrate | 0.48 mg/mL |
| Potassium phosphate monobasic | 0.06 mg/mL |
| Phenol | 2.5 mg/mL |
| Water | q.s. |

Composition 9:

| Component | Concentration |
|---|---|
| Inactivated BCG lysate | 50 mg/mL |
| Inactivated *Mycobacterium tuberculosis* lysate | 0.004 ng/mL |
| Inactivated *Staphylococcus aureus* lysate, inactivated *Staphylococcus epidermidis* lysate in equal parts. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Haemophilus influenza* lysate. | 6.94 μg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 μg/mL |
| Inactivated *Salmonella typhi*, *Salmonella paratyphi* and *Salmonella enterica* lysate in equal parts. | 6.94 μg/mL |
| Inactivated *Proteus mirabilis*, *Proteus vulgaris*, and *Proteus penerii* lysate in equal parts. | 6.94 μg/mL |

-continued

| Component | Concentration |
|---|---|
| Inactivated lysate of antigens of the measles virus ("Schwarz strain"). | 10,000 TDCI50/mL |
| Inactivated *Candida albincans* lysate, inactivated *Candida parapsilosis* lysate, inactivated *Candida glabrata* in equal parts. | 6.94 µg/mL |
| Glycerol | 500 mg/mL |
| Phenol | 2.5 mg/mL |
| Water | q.s. |

Composition 10:

| Component | Concentration |
|---|---|
| Inactivated *Mycobacterium africanum* lysate. | 0.004 ng/mL |
| Koch's Turberculin (inactivated *Mycobacterium bovis* lysate). | 0.004 ng/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated Epidermophyton floccosum, Microsporum cannis, Trichophyton mentagrophytes of the interdigitale variety lysate in equal parts). | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Acinetobacter baumannii* lysate. | 6.94 µg/mL |
| Inactivated *Helicobacter pylori* lysate. | 6.94 µg/mL |
| Inactivated lysate of antigens of the mumps virus (Urabe AM9 strain) | 10,000 TDCI50/mL |
| Inactivated Polio virus lysate | 40 UD of type I antigens; 1.8 UD of type 2 antigens; 32 UD of type 3 antigens |
| Glycerol | 500 mg/mL |
| Phenol | 2.5 mg/mL |
| Water | q.s. |

Composition 11:

| Component | Concentration |
|---|---|
| Inactivated *Mycobacterium leprae* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 µg/mL |
| Inactivated *Candida albincans* lysate, inactivated *Candida parapsilosis* lysate, inactivated *Candida glabrata* in equal parts. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Streptococcus equinus*, *Streptococcus bovis*, and *Streptococcus* of the viridans group lysate in equal parts. | 6.94 µg/mL |
| Inactivated *Haemophilus influenza* lysate. | 6.94 µg/mL |
| Inactivated *Proteus mirabilis*, *Proteus vulgaris*, and *Proteus penerii* lysate in equal parts. | 6.94 µg/mL |
| Antigens of the rubella virus (Wistar RA 27/3M strain) | 10,000 TDCI50/mL |

-continued

| Component | Concentration |
|---|---|
| Inactivate antigen of the Varicella zoster virus lysate | 149 231 PFU/mL |
| Glycerol | 500 mg/mL |
| Phenol | 2.5 mg/mL |
| Water | q.s. |

Composition 12:

| Component | Concentration |
|---|---|
| Inactivated *Mycobacterium avium* lysate | 0.004 ng/mL |
| Inactivated *Mycobacterium kansasii* lysate | 0.004 ng/mL |
| Inactivated *Apergillus fumigatus*, *Apergillus flavus*, and *Apergillus terreus* lysate in equal parts. | 6.94 µg/mL |
| Inactivated *Neisseria gonorrhoeae* lysate. | 6.94 µg/mL |
| Inactivated *Streptococcus equinus*, *Streptococcus bovis*, and *Streptococcus* of the viridans group lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Chlamydia trachomatis*, *Chlamydia psittaci*, and *Chamydia pneumoniae* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Antigens of the rubella virus (Wistar RA 27/3M strain) | 10,000 TDCI50/mL |
| Inactivated antigen of the Vaccinia (smallpox) virus lysate | 1 to $10 \times 10^9$ PFU/mL |
| Glycerol | 500 mg/mL |
| Phenol | 2.5 mg/mL |
| Water | q.s. |

Composition 13:

| Component | Concentration |
|---|---|
| Inactivated *Mycobacterium tuberculosis* lysate | 0.004 ng/mL |
| Inactivated *Mycobacterium avium* lysate | 0.004 ng/mL |
| Inactivated *Neisseria meningitides* lysate | 6.94 µg/mL |
| Diphtheria toxoid | 67 units of Lf/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated *Candida albincans* lysate, inactivated *Candida parapsilosis* lysate, inactivated *Candida glabrata* in equal parts. | 6.94 µg/mL |
| Inactivated *Helicobacter pylori* lysate. | 6.94 µg/mL |
| Inactivated *Serratia marcencens* e *Serratia liquefaciens* lysate | 6.94 µg/mL |
| Inactivated antigen of HSV-I and HSV-II lysate | 149 231 PFU/mL |
| Inactivated antigen of the measles virus ("Schwarz strain") lysate | 10,000 TDCI50/mL |
| Glycerol | 500 mg/mL |
| Phenol | 2.5 mg/mL |
| Water | q.s. |

Composition 14:

| Component | Concentration |
|---|---|
| Inactivated *Mycobacterium africanum* lysate | 0.004 ng/mL |
| Inactivated *Mycobacterium tuberculosis* lysate | 0.004 ng/mL |
| Inactivated *Neisseria gonorrhoeae* lysate | 6.94 mg/mL |
| Inactivated *Apergillus fumigatus*, *Apergillus flavus*, and *Apergillus terreus* lysate in equal parts. | 6.94 μg/mL |
| Inactivated *Neisseria meningitides* lysate | 6.94 μg/mL |
| Diphtheria toxoid | 67 units of Lf/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Shigella flexneri* and *Shigella sonnei* lysate in equal parts | 6.94 μg/mL |
| Inactivated surface antigen of the hepatitis B (HBs AG) virus lysate | 200 μg/mL |
| Inactivated antigen of the measles virus ("Schwarz strain") lysate | 10,000 TDCI50/mL |
| Glycerol | 500 mg/mL |
| Phenol | 2.5 mg/mL |
| Water | q.s. |

Composition 15:

| Component | Concentration |
|---|---|
| PPD | 0.004 ng/mL |
| Inactivated BCG lysate | 50 mg/mL |
| Inactivated *Streptococcus equinus*, *Streptococcus bovis*, and *Streptococcus* of the viridans group lysate in equal parts. | 6.94 μg/mL |
| Inactivated *Staphylococcus aureus* lysate, inactivated *Staphylococcus epidermidis* lysate in equal parts. | 6.94 μg/mL |
| Tetanus toxoid | 50 units of Lf/mL |
| Diphtheria toxoid | 67 units of Lf/mL |
| Inactivated *Acinetobacter baumannii* lysate. | 6.94 μg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Apergillus fumigatus*, *Apergillus flavus*, and *Apergillus terreus* lysate in equal parts. | 6.94 μg/mL |
| Inactivated lysate of antigens of the mumps virus (Urabe AM9 strain) | 10,000 TDCI50/mL |
| Glycerol | 500 mg/mL |
| Phenol | 2.5 mg/mL |
| Water | q.s. |

Composition 16:

| Component | Concentration |
|---|---|
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Salmonella typhi*, *Salmonella paratyphi* and *Salmonella enterica* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| *Bordetella pertussis* toxoid | 75 μg/mL |
| Inactivated *Haemophilus influenza* lysate. | 6.94 μg/mL |
| Tetanus toxoid | 50 units of Lf/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to 10 × 10⁹ PFU/mL |
| Glycerol | 500 mg/mL |
| Phenol | 2.5 mg/mL |
| Water | q.s. |

Composition 17:

| Component | Concentration |
|---|---|
| Koch's Turberculin (inactivated *Mycobacterium bovis* lysate). | 0.004 ng/mL |
| Inactivated BCG lysate | 50 mg/mL |
| PPD | 0.004 ng/mL |
| Inactivated *Staphylococcus aureus* lysate, inactivated *Staphylococcus epidermidis* lysate in equal parts. | 6.94 μg/mL |
| Inactivated *Streptococcus pyogenes* lysate, inactivated *Streptococcus pneumonie* lysate, *Enterococcus faecalis* lysate in equal parts. | 6.94 μg/mL |
| Inactivated *Klebsiella oxytoca* and *Klebsiella pneumonia* lysate in equal parts | 6.94 μg/mL |
| Inactivated *Epidermophyton floccosum*, *Microsporum cannis*, *Trichophyton mentagrophytes* of the interdigitale variety lysate in equal parts). | 6.94 μg/mL |
| Inactivated *Streptococcus equinus*, *Streptococcus bovis*, and *Streptococcus* of the viridans group lysate in equal parts. | 6.94 μg/mL |
| Diphtheria toxoid | 67 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 μg/mL |
| Inactivated *Salmonella typhi*, *Salmonella paratyphi* and *Salmonella enterica* lysate in equal parts. | 6.94 μg/mL |
| *Bordetella pertussis* toxoid | 75 μg/mL |
| Inactivated *Apergillus fumigatus*, *Apergillus flavus*, and *Apergillus terreus* lysate in equal parts. | 6.94 μg/mL |
| Inactivated lysate of antigens of the measles virus ("Schwarz strain"). | 10,000 TDCI50/mL |
| Inactivated *Candida albincans* lysate, inactivated *Candida parapsilosis* lysate, inactivated *Candida glabrata* in equal parts. | 6.94 μg/mL |
| Glycerol | 500 mg/mL |
| Phenol | 2.5 mg/mL |
| Water | q.s. |

Composition 18:

| Component | Concentration |
|---|---|
| PPD | 0.004 ng/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 μg/mL |

-continued

| Component | Concentration |
|---|---|
| Inactivated *Salmonella typhi, Salmonella paratyphi* and *Salmonella enterica* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Klebsiella oxytoca* and *Klebsiella pneumonia* lysate in equal parts | 6.94 µg/mL |
| Inactivated *Streptococcus agalactiae* lysate, inactivated *Streptococcus* mix (*Streptococcus pyogenes, Streptococcus pneumoniae* and *Enterococcus faecalis*) lysate in equal parts. | 6.94 µg/mL |
| Inactivated *Helicobacter pylori* lysate. | 6.94 µg/mL |
| Tetanus toxoid | 50 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Apergillus fumigatus, Apergillus flavus,* and *Apergillus terreus* lysate in equal parts. | 6.94 µg/mL |
| Inactivated YF-17D lysate | 3,000,000 PFU/mL |
| Glycerol | 500 mg/mL |
| Phenol | 2.5 mg/mL |
| Water | q.s. |

Composition 19:

| Component | Concentration |
|---|---|
| Inactivated BCG lysate | 50 mg/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Serratia marcencens* e *Serratia liquefaciens* lysate | 6.94 µg/mL |
| Inactivated *Haemophilus influenza* lysate. | 6.94 µg/mL |
| Inactivated *Streptococcus agalactiae* lysate, inactivated *Streptococcus* mix (*Streptococcus pyogenes, Streptococcus pneumoniae* and *Enterococcus faecalis*) lysate in equal parts. | 6.94 µg/mL |
| Inactivated *Klebsiella oxytoca* and *Klebsiella pneumonia* lysate in equal parts | 6.94 µg/mL |
| Inactivated *Epidermophyton floccosum, Microsporum cannis, Trichophyton mentagrophytes* of the interdigitale variety lysate in equal parts). | 6.94 µg/mL |
| Inactivated *Proteus mirabilis, Proteus vulgaris,* and *Proteus penerii* lysate in equal parts. | 6.94 µg/mL |
| Inactivated *Salmonella typhi, Salmonella paratyphi* and *Salmonella enterica* lysate in equal parts. | 6.94 µg/mL |
| Inactivated lysate of antigens of the measles virus ("Schwarz strain"). | 10,000 TDCI50/mL |
| Inactivated *Candida albicans* lysate, inactivated *Candida parapsilosis* lysate, inactivated *Candida glabrata* lysate in equal parts. | 6.94 µg/mL |
| Inactivated antigen of the Vaccinia (smallpox) virus lysate | 1 to 10 × 10$^9$ PFU/mL |
| Glycerol | 500 mg/mL |
| Phenol | 2.5 mg/mL |
| Water | q.s. |

Composition 20:

| Component | Concentration |
|---|---|
| Inactivated *Mycobacterium africanum* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Apergillus fumigatus, Apergillus flavus,* and *Apergillus terreus* lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Neisseria meningitides* lysate | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Salmonella typhi, Salmonella paratyphi* and *Salmonella enterica* lysate in equal parts. | 6.94 µg/mL |
| Inactivated *Acinetobacter baumannii* lysate. | 6.94 µg/mL |
| Inactivated *Helicobacter pylori* lysate. | 6.94 µg/mL |
| Inactivated *Haemophilus influenza* lysate. | 6.94 µg/mL |
| Inactivated lysate of antigens of the mumps virus (Urabe AM9 strain) | 50,000 TDCI50/mL |
| Inactivated Polio virus lysate | 40 UD of type I antigens; 1.8 UD of type 2 antigens; 32 UD of type 3 antigens |
| Inactivated *Candida albicans* lysate, inactivated *Candida parapsilosis* lysate, inactivated *Candida glabrata* lysate in equal parts. | 6.94 µg/mL |
| Glycerol | 500 mg/mL |
| Phenol | 2.5 mg/mL |
| Water | q.s. |

Composition 21:

| Component | Concentration |
|---|---|
| Inactivated *Mycobacterium leprae* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Staphylococcus aureus* lysate, inactivated *Staphylococcus epidermidis* lysate in equal parts. | 6.94 µg/mL |
| Inactivated *Epidermophyton floccosum, Microsporum cannis, Trichophyton mentagrophytes* of the interdigitale variety lysate in equal parts). | 6.94 µg/mL |
| Diphtheria toxoid | 67 units of Lf/mL |
| Inactivated *Streptococcus agalactiae* lysate, inactivated *Streptococcus* mix (*Streptococcus pyogenes, Streptococcus pneumoniae* and *Enterococcus faecalis*) lysate in equal parts. | 6.94 µg/mL |
| Tetanus toxoid | 50 units of Lf/mL |
| Inactivated *Neisseria meningitides* lysate | 6.94 µg/mL |
| Inactivated *Haemophilus influenza* lysate. | 6.94 µg/mL |

-continued

| Component | Concentration |
|---|---|
| Inactivated *Proteus mirabilis*, *Proteus vulgaris*, and *Proteus penerii* lysate in equal parts. | 6.94 µg/mL |
| Inactivated *Serratia marcencens* e *Serratia liquefaciens* lysate | 6.94 µg/mL |
| Antigens of the rubella virus (Wistar RA 27/3M strain) | 10,000 TDCI50/mL |
| Inactivate antigen of the Varicella zoster virus lysate | 149 231 PFU/mL |
| Inactivated *Apergillus fumigatus*, *Apergillus flavus*, and *Apergillus terreus* lysate in equal parts. | 6.94 µg/mL |
| Glycerol | 500 mg/mL |
| Phenol | 2.5 mg/mL |
| Water | q.s. |

Composition 22:

| Component | Concentration |
|---|---|
| Inactivated *Mycobacterium avium* lysate | 0.004 ng/mL |
| Inactivated *Mycobacterium kansasii* lysate | 0.004 ng/mL |
| Koch's Turberculin (inactivated *Mycobacterium bovis* lysate). | 0.004 ng/mL |
| Inactivated *Apergillus fumigatus*, *Apergillus flavus*, and *Apergillus terreus* lysate in equal parts. | 6.94 µg/mL |
| Inactivated *Neisseria gonorrhoeae* lysate | 6.94 mg/mL |
| Tetanus toxoid | 50 units of Lf/mL |
| Inactivated *Streptococcus equinus*, *Streptococcus bovis*, and *Streptococcus* of the viridans group lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Chlamydia trachomatis*, *Chlamydia psittaci*, and *Chamydia pneumoniae* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Klebsiella oxytoca* and *Klebsiella pneumonia* lysate in equal parts | 6.94 µg/mL |
| Antigens of the rubella virus (Wistar RA 27/3M strain) | 10,000 TDCI50/mL |
| Inactivated antigen of the Vaccinia (smallpox) virus lysate | 1 to 10 × 10$^9$ PFU/mL |
| Inactivated YF-17D lysate | 3,000,000 PFU/mL |
| Glycerol | 500 mg/mL |
| Phenol | 2.5 mg/mL |
| Water | q.s. |

Composition 23:

| Component | Concentration |
|---|---|
| Inactivated *Mycobacterium tuberculosis* lysate | 0.004 ng/mL |
| Inactivated *Mycobacterium avium* lysate | 0.004 ng/mL |
| Koch's Turberculin (inactivated *Mycobacterium bovis* lysate). | 0.004 ng/mL |
| Inactivated *Neisseria meningitides* lysate | 6.94 µg/mL |
| Diphtheria toxoid | 67 units of Lf/mL |
| Tetanus toxoid | 50 units of Lf/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |

-continued

| Component | Concentration |
|---|---|
| Inactivated *Candida albicans* lysate, inactivated *Candida parapsilosis* lysate, inactivated *Candida glabrata* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Helicobacter pylori* lysate. | 6.94 µg/mL |
| Inactivated *Serratia marcencens* e *Serratia liquefaciens* lysate | 6.94 µg/mL |
| Inactivated *Salmonella typhi*, *Salmonella paratyphi* and *Salmonella enterica* lysate in equal parts. | 6.94 µg/mL |
| Inactivated antigen of HSV-I and HSV-II lysate | 149 231 PFU/mL |
| Inactivated lysate of antigens of the measles virus ("Schwarz strain"). | 10,000 TDCI50/mL |
| Inactivated *Apergillus fumigatus*, *Apergillus flavus*, and *Apergillus terreus* lysate in equal parts. | 6.94 µg/mL |
| Glycerol | 500 mg/mL |
| Phenol | 2.5 mg/mL |
| Water | q.s. |

Composition 24:

| Component | Concentration |
|---|---|
| Inactivated *Mycobacterium africanum* lysate | 0.004 ng/mL |
| Inactivated *Mycobacterium tuberculosis* lysate | 0.004 ng/mL |
| PPD | 0.004 ng/mL |
| Inactivated *Neisseria gonorrhoeae* lysate | 6.94 mg/mL |
| Inactivated *Candida albicans* lysate, inactivated *Candida parapsilosis* lysate, inactivated *Candida glabrata* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Neisseria meningitides* lysate | 6.94 µg/mL |
| Diphtheria toxoid | 67 units of Lf/mL |
| Inactivated *Streptococcus equinus*, *Streptococcus bovis*, and *Streptococcus* of the viridans group lysate in equal parts. | 6.94 µg/mL |
| Tetanus toxoid | 50 units of Lf/mL |
| Inactivated *Shigella flexneri* and *Shigella sonnei* lysate in equal parts | 6.94 µg/mL |
| Inactivated *Proteus mirabilis*, *Proteus vulgaris*, and *Proteus penerii* lysate in equal parts. | 6.94 µg/mL |
| Inactivated surface antigen of the hepatitis B (HBs AG) virus lysate | 200 µg/mL |
| Inactivated lysate of antigens of the measles virus ("Schwarz strain"). | 10,000 TDCI50/mL |
| Inactivated YF-17D lysate | 3,000,000 PFU/mL |
| Glycerol | 500 mg/mL |
| Phenol | 2.5 mg/mL |
| Water | q.s. |

Composition 25:

| Component | Concentration |
|---|---|
| PPD | 0.004 ng/mL |
| Inactivated BCG lysate | 50 mg/mL |
| Koch's Turberculin (inactivated *Mycobacterium bovis* lysate). | 0.004 ng/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Staphylococcus aureus* lysate, inactivated *Staphylococcus epidermidis* lysate in equal parts. | 6.94 µg/mL |
| Diphtheria toxoid | 67 units of Lf/mL |

-continued

| Component | Concentration |
|---|---|
| Tetanus toxoid | 50 units of Lf/mL |
| Inactivated *Salmonella typhi*, *Salmonella paratyphi* and *Salmonella enterica* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Acinetobacter baumannii* lysate. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated lysate of antigens of the mumps virus (Urabe AM9 strain) | 50,000 TDCI50/mL |
| Inactivated antigen of the Vaccinia (smallpox) virus lysate | 1 to 10 × $10^9$ PFU/mL |
| Glycerol | 500 mg/mL |
| Phenol | 2.5 mg/mL |
| Water | q.s. |

Composition 26:

| Component | Concentration |
|---|---|
| Koch's Turberculin (inactivated *Mycobacterium bovis* lysate). | 0.004 ng/mL |
| Inactivated *Mycobacterium tuberculosis* lysate | 0.004 ng/mL |
| Inactivated BCG lysate | 50 mg/mL |
| Inactivated *Apergillus fumigatus*, *Apergillus flavus*, and *Apergillus terreus* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Chlamydia trachomatis*, *Chlamydia psittaci*, and *Chamydia pneumoniae* lysate in equal parts. | 6.94 µg/mL |
| *Bordetella pertussis* toxoid | 75 µg/mL |
| Inactivated *Haemophilus influenza* lysate. | 6.94 µg/mL |
| Inactivated *Neisseria gonorrhoeae* lysate | 6.94 mg/mL |
| Tetanus toxoid | 50 units of Lf/mL |
| Inactivated *Candida albicans* lysate, inactivated *Candida parapsilosis* lysate, inactivated *Candida glabrata* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to 10 × $10^9$ PFU/mL |
| Inactivated YF-17D lysate | 3,000,000 PFU/mL |

Composition 27:

| Component | Concentration |
|---|---|
| Inactivated YF-17D lysate | 3,000,000 PFU/mL |
| Koch's Turberculin (inactivated *Mycobacterium bovis* lysate). | 0.004 ng/mL |
| Inactivated BCG lysate | 50 mg/mL |
| PPD | 0.004 ng/mL |
| Inactivated *Mycobacterium tuberculosis* lysate | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Klebsiella oxytoca* and *Klebsiella pneumonia* lysate in equal parts | 6.94 µg/mL |
| Inactivated *Neisseria meningitides* lysate | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Streptococcus equinus*, *Streptococcus bovis*, and *Streptococcus* of the viridans group lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Shigella flexneri* and *Shigella sonnei* lysate in equal parts | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Salmonella typhi*, *Salmonella paratyphi* and *Salmonella enterica* lysate in equal parts. | 6.94 µg/mL |
| *Bordetella pertussis* toxoid | 75 µg/mL |
| Inactivated antigen of the Vaccinia (smallpox) virus lysate | 1 to 10 × $10^9$ PFU/mL |
| Inactivated *Apergillus fumigatus*, *Apergillus flavus*, and *Apergillus terreus* lysate in equal parts. | 6.94 µg/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 28:

| Component | Concentration |
|---|---|
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Mycobacterium avium* lysate | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Neisseria meningitides* lysate | 6.94 µg/mL |
| Streptokinase derived from inactivated beta-hemolytic *Streptococcus* lysate purification. | 0.444 µg/mL |
| Dornase derived from inactivated beta-hemolytic *Streptococcus* lysate purification. | 0.111 µg/mL |
| Inactivated *Salmonella typhi*, *Salmonella paratyphi* and *Salmonella enterica* lysate in equal parts. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |

-continued

| Component | Concentration |
|---|---|
| Inactivated *Enterobacter aerogenes*, *Enterobacter cloacae*, and *Enterobacter agglomerans* group lysate. | 6.94 µg/mL |
| Inactivated *Helicobacter pylori* lysate. | 6.94 µg/mL |
| Tetanus toxoid | 50 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated antigen of the Vaccinia (smallpox) virus lysate | 1 to 10 × $10^9$ PFU/mL |
| Inactivated *Candida albicans* lysate, inactivated *Candida parapsilosis* lysate, inactivated *Candida glabrata* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated YF-17D lysate | 3,000,000 PFU/mL |
| Glycerol | 500 mg/mL |
| Phenol | 2.5 mg/mL |
| Water | q.s. |

Composition 29:

| Component | Concentration |
|---|---|
| Inactivated lysate of antigens of the mumps virus (Urabe AM9 strain) | 50,000 TDCI50/mL |
| Inactivated BCG lysate | 50 mg/mL |
| Inactivated *Mycobacterium tuberculosis* lysate | 0.004 ng/mL |
| Koch's Turberculin (inactivated *Mycobacterium bovis* lysate). | 0.004 ng/mL |
| Inactivated *Mycobacterium leprae* lysate | 0.004 ng/mL |
| Inactivated *Staphylococcus aureus* lysate, inactivated *Staphylococcus epidermidis* lysate in equal parts. | 6.94 µg/mL |
| Inactivated *Streptococcus equinus*, *Streptococcus bovis*, and *Streptococcus* of the viridans group lysate in equal parts. | 6.94 µg/mL |
| Inactivated *Serratia marcencens* and *Serratia liquefaciens* lysate | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Haemophilus influenza* lysate. | 6.94 µg/mL |
| Inactivated *Streptococcus agalactiae* lysate, inactivated *Streptococcus* mix (*Streptococcus pyogenes*, *Streptococcus pneumoniae* and *Enterococcus faecalis*) lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Tetanus toxoid | 50 units of Lf/mL |
| Inactivated *Proteus mirabilis*, *Proteus vulgaris*, and *Proteus penerii* lysate in equal parts. | 6.94 µg/mL |
| Inactivated *Salmonella typhi*, *Salmonella paratyphi* and *Salmonella enterica* lysate in equal parts. | 6.94 µg/mL |
| Inactivated *Apergillus fumigatus*, *Apergillus flavus*, and *Apergillus terreus* lysate in equal parts. | 6.94 µg/mL |
| Inactivated lysate of antigens of the measles virus ("Schwarz strain"). | 10,000 TDCI50/mL |
| Inactivated *Candida albicans* lysate, inactivated *Candida parapsilosis* lysate, inactivated *Candida glabrata* lysate in equal parts. | 6.94 µg/mL |
| Inactivated antigen of the Vaccinia (smallpox) virus lysate | 1 to 10 × $10^9$ PFU/mL |
| Glycerol | 500 mg/mL |

-continued

| Component | Concentration |
|---|---|
| Phenol | 2.5 mg/mL |
| Water | q.s. |

Composition 30:

| Component | Concentration |
|---|---|
| Inactivated *Apergillus fumigatus*, *Apergillus flavus*, and *Apergillus terreus* lysate in equal parts. | 6.94 µg/mL |
| Inactivated *Mycobacterium africanum* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Mycobacterium tuberculosis* lysate | 0.004 ng/mL |
| Inactivated *Streptococcus equinus*, *Streptococcus bovis*, and *Streptococcus* of the viridans group lysate in equal parts. | 6.94 µg/mL |
| Inactivated *Staphylococcus aureus* lysate, inactivated *Staphylococcus epidermidis* lysate in equal parts. | 6.94 µg/mL |
| Inactivated *Neisseria meningitides* lysate | 6.94 µg/mL |
| Diphtheria toxoid | 67 units of Lf/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Epidermophyton floccosum*, *Microsporum cannis*, *Trichophyton mentagrophytes* of the interdigitale variety lysate in equal parts). | 6.94 µg/mL |
| Inactivated *Salmonella typhi*, *Salmonella paratyphi* and *Salmonella enterica* lysate in equal parts. | 6.94 µg/mL |
| Inactivated *Acinetobacter baumannii* lysate. | 6.94 µg/mL |
| Inactivated *Helicobacter pylori* lysate. | 6.94 µg/mL |
| Inactivated *Haemophilus influenza* lysate. | 6.94 µg/mL |
| Inactivated YF-17D lysate | 3,000,000 PFU/mL |
| Inactivated lysate of antigens of the mumps virus (Urabe AM9 strain) | 50,000 TDCI50/mL |
| Inactivated Polio virus lysate | 40 UD of type I antigens; 1.8 UD of type 2 antigens; 32 UD of type 3 antigens |
| Inactivated *Candida albicans* lysate, inactivated *Candida parapsilosis* lysate, inactivated *Candida glabrata* lysate in equal parts. | 6.94 µg/mL |
| Glycerol | 500 mg/mL |
| Phenol | 2.5 mg/mL |
| Water | q.s. |

Composition 31:

| Component | Concentration |
|---|---|
| Inactivated *Salmonella typhi*, *Salmonella paratyphi* and *Salmonella enterica* lysate in equal parts. | 6.94 µg/mL |
| Inactivated *Mycobacterium leprae* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| PPD | 0.004 ng/mL |
| Inactivated *Staphylococcus aureus* lysate, inactivated *Staphylococcus epidermidis* lysate in equal parts. | 6.94 µg/mL |
| Inactivated *Streptococcus pyogenes* lysate, inactivated *Streptococcus pneumonie* lysate, *Enterococcus faecalis* lysate in equal parts. | 6.94 µg/mL |
| Diphtheria toxoid | 67 units of Lf/mL |

| Component | Concentration |
|---|---|
| Inactivated *Neisseria gonorrhoeae* lysate | 6.94 mg/mL |
| Inactivated *Streptococcus agalactiae* lysate, inactivated *Streptococcus* mix (*Streptococcus pyogenes, Streptococcus pneumoniae* and *Enterococcus faecalis*) lysate in equal parts. | 6.94 µg/mL |
| Inactivated *Epidermophyton floccosum, Microsporum cannis, Trichophyton mentagrophytes* of the interdigitale variety lysate in equal parts). | 6.94 µg/mL |
| Inactivated *Neisseria meningitides* lysate | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Haemophilus influenza* lysate. | 6.94 µg/mL |
| Inactivated *Proteus mirabilis, Proteus vulgaris,* and *Proteus penerii* lysate in equal parts. | 6.94 µg/mL |
| Inactivated *Serratia marcencens* e *Serratia liquefaciens* lysate | 6.94 µg/mL |
| Inactivated *Candida albicans* lysate, inactivated *Candida parapsilosis* lysate, inactivated *Candida glabrata* lysate in equal parts. | 6.94 µg/mL |
| Antigens of the rubella virus (Wistar RA 27/3M strain) | 10,000 TDCI50/mL |
| Inactivate antigen of the Varicella zoster virus lysate | 149 231 PFU/mL |
| Inactivated *Apergillus fumigatus, Apergillus flavus,* and *Apergillus terreus* lysate in equal parts. | 6.94 µg/mL |
| Glycerol | 500 mg/mL |
| Phenol | 2.5 mg/mL |
| Water | q.s. |

Composition 32:

| Component | Concentration |
|---|---|
| Inactivated *Candida albicans* lysate, inactivated *Candida parapsilosis* lysate, inactivated *Candida glabrata* lysate in equal parts. | 6.94 µg/mL |
| Inactivated *Mycobacterium avium* lysate | 0.004 ng/mL |
| Inactivated *Mycobacterium kansasii* lysate | 0.004 ng/mL |
| Koch's Turberculin (inactivated *Mycobacterium bovis* lysate). | 0.004 ng/mL |
| Inactivated BCG lysate | 50 mg/mL |
| Inactivated *Apergillus fumigatus, Apergillus flavus,* and *Apergillus terreus* lysate in equal parts. | 6.94 µg/mL |
| Inactivated *Neisseria gonorrhoeae* lysate | 6.94 mg/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Streptococcus equinus, Streptococcus bovis,* and *Streptococcus* of the viridans group lysate in equal parts. | 6.94 µg/mL |
| Inactivated *Epidermophyton floccosum, Microsporum cannis, Trichophyton mentagrophytes* of the interdigitale variety lysate in equal parts). | 6.94 µg/mL |
| Inactivated *Salmonella typhi, Salmonella paratyphi* and *Salmonella enterica* lysate in equal parts. | 6.94 µg/mL |
| Inactivated *Helicobacter pylori* lysate. | 6.94 µg/mL |
| Inactivated *Chlamydia trachomatis, Chlamydia psittaci,* and *Chamydia pneumoniae* lysate in equal parts. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Klebsiella oxytoca* and *Klebsiella pneumonia* lysate in equal parts | 6.94 µg/mL |
| Antigens of the rubella virus (Wistar RA 27/3M strain) | 10,000 TDCI50/mL |
| Inactivated antigen of the Vaccinia (smallpox) virus lysate | 1 to 10 × $10^9$ PFU/mL |
| Inactivated YF-17D lysate | 3,000,000 PFU/mL |
| Glycerol | 500 mg/mL |
| Phenol | 2.5 mg/mL |
| Water | q.s. |

Composition 33:

| Component | Concentration |
|---|---|
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) *Escherichia coli* lysate in equal parts. | 6.94 µg/mL |
| Inactivated *Mycobacterium leprae* lysate | 0.004 ng/mL |
| Inactivated *Mycobacterium avium* lysate | 0.004 ng/mL |
| Koch's Turberculin (inactivated *Mycobacterium bovis* lysate). | 0.004 ng/mL |
| Inactivated *Mycobacterium tuberculosis* lysate | 0.004 ng/mL |
| Inactivated *Neisseria meningitides* lysate | 6.94 µg/mL |
| Diphtheria toxoid | 67 units of Lf/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Apergillus fumigatus, Apergillus flavus,* and *Apergillus terreus* lysate in equal parts. | 6.94 µg/mL |
| Inactivated *Candida albicans* lysate, inactivated *Candida parapsilosis* lysate, inactivated *Candida glabrata* lysate in equal parts. | 6.94 µg/mL |
| Inactivated *Shigella flexneri* and *Shigella sonnei* lysate in equal parts | 6.94 µg/mL |
| Inactivated *Helicobacter pylori* lysate. | 6.94 µg/mL |
| Inactivated *Serratia marcencens* e *Serratia liquefaciens* lysate | 6.94 µg/mL |
| Inactivated *Salmonella typhi, Salmonella paratyphi* and *Salmonella enterica* lysate in equal parts. | 6.94 µg/mL |
| Inactivated antigen of the Vaccinia (smallpox) virus lysate | 1 to 10 × $10^9$ PFU/mL |
| Inactivated antigen of HSV-I and HSV-II lysate | 149 231 PFU/mL |
| Inactivated lysate of antigens of the measles virus ("Schwarz strain"). | 10,000 TDCI50/mL |
| Glycerol | 500 mg/mL |
| Phenol | 2.5 mg/mL |
| Water | q.s. |

Composition 34:

| Component | Concentration |
|---|---|
| Inactivated *Candida albicans* lysate, inactivated *Candida parapsilosis* lysate, inactivated *Candida glabrata* lysate in equal parts. | 6.94 µg/mL |
| Inactivated *Mycobacterium africanum* lysate | 0.004 ng/mL |
| Inactivated *Mycobacterium tuberculosis* lysate | 0.004 ng/mL |
| PPD | 0.004 ng/mL |
| Inactivated BCG lysate | 50 mg/mL |
| Tetanus toxoid | 50 units of Lf/mL |
| Inactivated *Streptococcus pyogenes* lysate, inactivated *Streptococcus pneumonie* lysate, *Enterococcus faecalis* lysate in equal parts. | 6.94 µg/mL |
| Inactivated *Salmonella typhi, Salmonella paratyphi* and *Salmonella enterica* lysate in equal parts. | 6.94 µg/mL |

-continued

| Component | Concentration |
|---|---|
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) Escherichia coli lysate in equal parts. | 6.94 µg/mL |
| Inactivated Neisseria meningitides lysate | 6.94 µg/mL |
| Diphtheria toxoid | 67 units of Lf/mL |
| Inactivated Streptococcus equinus, Streptococcus bovis, and Streptococcus of the viridans group lysate in equal parts. | 6.94 µg/mL |
| Inactivated Apergillus fumigatus, Apergillus flavus, and Apergillus terreus lysate in equal parts. | 6.94 µg/mL |
| Inactivated Shigella flexneri and Shigella sonnei lysate in equal parts | 6.94 µg/mL |
| Inactivated Proteus mirabilis, Proteus vulgaris, and Proteus penerii lysate in equal parts. | 6.94 µg/mL |
| Inactivated surface antigen of the hepatitis B (HBs AG) virus lysate | 200 µg/mL |
| Inactivated lysate of antigens of the measles virus ("Schwarz strain"). | 110,000 TDCI50/mL |
| Inactivated YF-17D lysate | 3,000,000 PFU/mL |
| Glycerol | 500 mg/mL |
| Phenol | 2.5 mg/mL |
| Water | q.s. |

Composition 35:

| Component | Concentration |
|---|---|
| Inactivated Candida albicans lysate, inactivated Candida parapsilosis lysate, inactivated Candida glabrata lysate in equal parts. | 6.94 µg/mL |
| PPD | 0.004 ng/mL |
| Inactivated BCG lysate | 50 mg/mL |
| Koch's Turberculin (inactivated Mycobacterium bovis lysate). | 0.004 ng/mL |
| Inactivated Mycobacterium tuberculosis lysate | 0.004 ng/mL |
| Inactivated Streptococcus pyogenes lysate, inactivated Streptococcus pneumonie lysate, Enterococcus faecalis lysate in equal parts. | 6.94 µg/mL |
| Inactivated Staphylococcus aureus lysate, inactivated Staphylococcus epidermidis lysate in equal parts. | 6.94 µg/mL |
| Inactivated Epidermophyton floccosum, Microsporum cannis, Trichophyton mentagrophytes of the interdigitale variety lysate in equal parts). | 6.94 µg/mL |
| Inactivated Neisseria meningitides lysate | 6.94 µg/mL |
| Tetanus toxoid | 50 units of Lf/mL |
| Diphtheria toxoid | 67 units of Lf/mL |
| Inactivated Streptococcus equinus, Streptococcus bovis, and Streptococcus of the viridans group lysate in equal parts. | 6.94 µg/mL |
| Inactivated Serratia marcencens e Serratia liquefaciens lysate | 6.94 µg/mL |
| Inactivated Acinetobacter baumannii lysate. | 6.94 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) Escherichia coli lysate in equal parts. | 6.94 µg/mL |
| Inactivated Salmonella typhi, Salmonella paratyphi and Salmonella enterica lysate in equal parts. | 6.94 µg/mL |
| Inactivated YF-17D lysate | 3,000,000 PFU/mL |
| Inactivated Apergillus fumigatus, Apergillus flavus, and Apergillus terreus lysate in equal parts. | 6.94 µg/mL |
| Inactivated lysate of antigens of the mumps virus (Urabe AM9 strain) | 50,000 TDCI50/mL |
| Inactivated antigen of the Vaccinia (smallpox) virus lysate | 1 to 10 × $10^9$ PFU/mL |
| Glycerol | 500 mg/mL |
| Phenol | 2.5 mg/mL |
| Water | q.s. |

Composition 36:

| Component | Concentration |
|---|---|
| Inactivated Apergillus fumigatus, Apergillus flavus, and Apergillus terreus lysate in equal parts. | 6.94 µg/mL |
| Koch's Turberculin (inactivated Mycobacterium bovis lysate). | 0.004 ng/mL |
| Inactivated Mycobacterium tuberculosis lysate | 0.004 ng/mL |
| Inactivated BCG lysate | 50 mg/mL |
| PPD (purified protein derivative) | 0.004 ng/mL |
| Inactivated Streptococcus pyogenes lysate, inactivated Streptococcus pneumonie lysate, Enterococcus faecalis lysate in equal parts. | 6.94 µg/mL |
| Inactivated Chlamydia trachomatis, Chlamydia psittaci, and Chamydia pneumoniae lysate in equal parts. | 6.94 µg/mL |
| Inactivated Epidermophyton floccosum, Microsporum cannis, Trichophyton mentagrophytes of the interdigitale variety lysate in equal parts). | 6.94 µg/mL |
| Bordetella pertussis toxoid | 75 µg/mL |
| Inactivated Haemophilus influenza lysate. | 6.94 µg/mL |
| Streptokinase derived from inactivated beta-hemolytic Streptococcus lysate purification. | 0.444 µg/mL |
| Dornase derived from inactivated beta-hemolytic Streptococcus lysate purification. | 0.111 µg/mL |
| Inactivated Salmonella typhi, Salmonella paratyphi and Salmonella enterica lysate in equal parts. | 6.94 µg/mL |
| Tetanus toxoid | 50 units of Lf/mL |
| Inactivated surface antigen of the hepatitis B (HBs AG) virus lysate | 200 µg/mL |
| Inactivated enteropathogenic (EPEC), "shiga-like" toxin producer (STEC), enteroaggregative (EAEC), enterotoxigenic (ETEC), enteroinvasive (EIEC) and extraintestinal (ExPEC) Escherichia coli lysate in equal parts. | 6.94 µg/mL |
| Inactivated Candida albicans lysate, inactivated Candida parapsilosis lysate, inactivated Candida glabrata lysate in equal parts. | 6.94 µg/mL |
| Inactivated Polio virus lysate | 40 UD of type I antigens; 1.8 UD of type 2 antigens; 32 UD of type 3 antigens |
| Inactivated antigen of the Vaccinia (smallpox) virus lysate | 1 to 10 × $10^9$ PFU/mL |
| Inactivated YF-17D lysate | 3,000,000 PFU/mL |
| Glycerol | 500 mg/mL |
| Phenol | 2.5 mg/mL |
| Water | q.s. |

When there are parasitic diseases, associated or to be fought, the formulations will preferentially contain antigenic agents of parasitic origin. In this case, according to the concept described in the present invention, the formulations should comprise antigenic agents originating from the most prevalent parasites for which the individuals have more memory cells, according to the geographic distribution and the local and regional human development (developed or non-developed countries). Such parameters are determinant for the occurrence of these parasites and the existence of corresponding memory cells in the immune system of the population of a given region.

Composition 37: Association of Composition 2 with:

| Component | Concentration |
|---|---|
| Inactivated *Toxoplasma gondii* lysate | 400 µg/mL |

Composition 38: Association of Composition 3 with:

| Component | Concentration |
|---|---|
| Inactivated *Giardi lamblia* lysate | 400 µg/mL |

Composition 39: Association of Composition 4 with:

| Component | Concentration |
|---|---|
| Inactivated *Entamoeba histolytica* lysate | 400 µg/mL |

Composition 40: Association of Composition 5 with:

| Component | Concentration |
|---|---|
| Inactivated *Ascaris lumbricoides* lysate | 400 µg/mL |

Composition 41: Association of Composition 6 with:

| Component | Concentration |
|---|---|
| Inactivated *Enterobius vermicularis* lysate | 400 µg/mL |

Composition 42: Association of Composition 7 with:

| Component | Concentration |
|---|---|
| Inactivated *Entamoeba histolytica* lysate | 400 µg/mL |
| Inactivated *Ascaris lumbricoides* lysate | 400 µg/mL |

Composition 43: Association of Composition 8 with:

| Component | Concentration |
|---|---|
| Inactivated *Giardi lamblia* lysate | 400 µg/mL |
| Inactivated *Enterobius vermicularis* lysate | 400 µg/mL |

Composition 44: Association of Composition 9 with:

| Component | Concentration |
|---|---|
| Inactivated *Strongyloides stercoralis* lysate | 400 µg/mL |
| Inactivated *Entamoeba histolytica* lysate | 400 µg/mL |

Composition 45: Association of Composition 10 with:

| Component | Concentration |
|---|---|
| Inactivated *Giardia lamblia* lysate | 400 µg/mL |
| Inactivated *Ascaris lumbricoides* lysate | 400 µg/mL |

Composition 46: Association of Composition 11 with:

| Component | Concentration |
|---|---|
| Inactivated *Toxoplasma gondii* lysate | 400 µg/mL |
| Inactivated *Entamoeba histolytica* lysate | 400 µg/mL |

Composition 47: Association of Composition 12 with

| Component | Concentration |
|---|---|
| Inactivated *Strongyloides stercoralis* lysate | 400 µg/mL |
| Inactivated *Cryptosporidium* spp. lysate | 400 µg/mL |

Composition 48: Association of Composition 13 with:

| Component | Concentration |
|---|---|
| Inactivated *Ascaris lumbricoides* lysate | 400 µg/mL |
| Inactivated *Toxoplasma gondii* lysate | 400 µg/mL |

Composition 49: Association of Composition 14 with:

| Component | Concentration |
|---|---|
| Inactivated *Entamoeba histolytica* lysate | 400 µg/mL |
| Inactivated *Giardia lamblia* lysate | 400 µg/mL |

Composition 50: Association of Composition 15 with:

| Component | Concentration |
|---|---|
| Inactivated *Strongyloides stercoralis* lysate | 400 µg/mL |
| Inactivated *Enterobius vermicularis* lysate | 400 µg/mL |

Composition 51: Association of Composition 16 with:

| Component | Concentration |
|---|---|
| Inactivated *Trichomonas vaginalis* lysate | 400 µg/mL |
| Inactivated *Ascaris lumbricoides* lysate | 400 µg/mL |

Composition 52: Association of Composition 17 with:

| Component | Concentration |
|---|---|
| Inactivated *Entamoeba histolytica* lysate | 400 µg/mL |
| Inactivated *Ascaris lumbricoides* lysate | 400 µg/mL |
| Inactivated *Enterobius vermicularis* lysate | 400 µg/mL |

Composition 53: Association of Composition 18 with:

| Component | Concentration |
|---|---|
| Inactivated *Giardia lamblia* lysate | 400 µg/mL |
| Inactivated *Enterobius vermicularis* lysate | 400 µg/mL |
| Inactivated *Toxoplasma gondii* lysate | 400 µg/mL |

Composition 54: Association of Composition 19 with:

| Component | Concentration |
|---|---|
| Inactivated *Strongyloides stercoralis* lysate | 400 µg/mL |
| Inactivated *Entamoeba histolytica* lysate | 400 µg/mL |
| Inactivated *Giardia lamblia* lysate | 400 µg/mL |

Composition 55: Association of Composition 20 with:

| Component | Concentration |
|---|---|
| Inactivated *Giardia lamblia* lysate | 400 µg/mL |
| Inactivated *Ascaris lumbricoides* lysate | 400 µg/mL |
| Inactivated *Strongyloides stercoralis* lysate | 400 µg/mL |

Composition 56: Association of Composition 21 with:

| Component | Concentration |
|---|---|
| Inactivated *Toxoplasma gondii* lysate | 400 µg/mL |
| Inactivated *Entamoeba histolytica* lysate | 400 µg/mL |
| Inactivated *Giardia lamblia* lysate | 400 µg/mL |

Composition 57: Association of Composition 22 with:

| Component | Concentration |
|---|---|
| Inactivated *Strongyloides stercoralis* lysate | 400 µg/mL |
| Inactivated *Cryptosporidium* spp. lysate | 400 µg/mL |
| Inactivated *Entamoeba histolytica* lysate | 400 µg/mL |

Composition 58: Association of Composition 23 with:

| Component | Concentration |
|---|---|
| Inactivated *Ascaris lumbricoides* lysate | 400 µg/mL |
| Inactivated *Toxoplasma gondii* lysate | 400 µg/mL |
| Inactivated *Enterobius vermicularis* lysate | 400 µg/mL |

Composition 59: Association of Composition 24 with:

| Component | Concentration |
|---|---|
| Inactivated *Entamoeba histolytica* lysate | 400 µg/mL |
| Inactivated *Giardia lamblia* lysate | 400 µg/mL |
| Inactivated *Ascaris lumbricoides* lysate | 400 µg/mL |

Composition 60: Association of Composition 25 with:

| Component | Concentration |
|---|---|
| Inactivated *Strongyloides stercoralis* lysate | 400 µg/mL |
| Inactivated *Enterobius vermicularis* lysate | 400 µg/mL |
| Inactivated *Entamoeba histolytica* lysate | 400 µg/mL |

Composition 61: Association of Composition 26 with:

| Component | Concentration |
|---|---|
| Inactivated *Trichomonas vaginalis* lysate | 400 µg/mL |
| Inactivated *Ascaris lumbricoides* lysate | 400 µg/mL |
| Inactivated *Giardia lamblia* lysate | 400 µg/mL |

Composition 62: Association of Composition 27 with:

| Component | Concentration |
|---|---|
| Inactivated *Entamoeba histolytica* lysate | 400 µg/mL |
| Inactivated *Ascaris lumbricoides* lysate | 400 µg/mL |
| Inactivated *Enterobius vermicularis* lysate | 400 µg/mL |
| Inactivated *Cryptosporidium* spp. lysate | 400 µg/mL |

Composition 63: Association of Composition 28 with:

| Component | Concentration |
|---|---|
| Inactivated *Giardia lamblia* lysate | 400 µg/mL |
| Inactivated *Enterobius vermicularis* lysate | 400 µg/mL |
| Inactivated *Toxoplasma gondii* lysate | 400 µg/mL |
| Inactivated *Ascaris lumbricoides* lysate | 400 µg/mL |

Composition 64: Association of Composition 29 with:

| Component | Concentration |
|---|---|
| Inactivated *Strongyloides stercoralis* lysate | 400 µg/mL |
| Inactivated *Entamoeba histolytica* lysate | 400 µg/mL |
| Inactivated *Giardia lamblia* lysate | 400 µg/mL |
| Inactivated *Enterobius vermicularis* lysate | 400 µg/mL |

Composition 65: Association of Composition 30 with:

| Component | Concentration |
|---|---|
| Inactivated *Giardia lamblia* lysate | 400 µg/mL |
| Inactivated *Ascaris lumbricoides* lysate | 400 µg/mL |
| Inactivated *Strongyloides stercoralis* lysate | 400 µg/mL |
| Inactivated *Entamoeba histolytica* lysate | 400 µg/mL |

Composition 66: Association of Composition 31 with:

| Component | Concentration |
|---|---|
| Inactivated *Toxoplasma gondii* lysate | 400 µg/mL |
| Inactivated *Entamoeba histolytica* lysate | 400 µg/mL |
| Inactivated *Giardia lamblia* lysate | 400 µg/mL |
| Inactivated *Enterobius vermicularis* lysate | 400 µg/mL |

Composition 67: Association of Composition 32 with:

| Component | Concentration |
|---|---|
| Inactivated *Strongyloides stercoralis* lysate | 400 µg/mL |
| Inactivated *Cryptosporidium* spp. lysate | 400 µg/mL |
| Inactivated *Entamoeba histolytica* lysate | 400 µg/mL |
| Inactivated *Ascaris lumbricoides* lysate | 400 µg/mL |

Composition 68: Association of Composition 33 with:

| Component | Concentration |
|---|---|
| Inactivated *Ascaris lumbricoides* lysate | 400 µg/mL |
| Inactivated *Toxoplasma gondii* lysate | 400 µg/mL |
| Inactivated *Enterobius vermicularis* lysate | 400 µg/mL |
| Inactivated *Cryptosporidium* spp. lysate | 400 µg/mL |

Composition 69: Association of Composition 34 with:

| Component | Concentration |
|---|---|
| Inactivated *Entamoeba histolytica* lysate | 400 µg/mL |
| Inactivated *Giardia lamblia* lysate | 400 µg/mL |
| Inactivated *Ascaris lumbricoides* lysate | 400 µg/mL |
| Inactivated *Trichomonas vaginalis* lysate | 400 µg/mL |

Composition 70: Association of Composition 35 with:

| Component | Concentration |
|---|---|
| Inactivated *Strongyloides stercoralis* lysate | 400 µg/mL |
| Inactivated *Enterobius vermicularis* lysate | 400 µg/mL |
| Inactivated *Entamoeba histolytica* lysate | 400 µg/mL |
| Inactivated *Cryptosporidium* spp. lysate | 400 µg/mL |

Composition 71: Association of Composition 36 with:

| Component | Concentration |
|---|---|
| Inactivated *Trichomonas vaginalis* lysate | 400 µg/mL |
| Inactivated *Ascaris lumbricoides* lysate | 400 µg/mL |
| Inactivated *Giardia lamblia* lysate | 400 µg/mL |
| Inactivated *Strongyloides stercoralis* lysate | 400 µg/mL |

Example 2

Experimental Treatment Model of Melanoma on Mice Using the DECA Antigenic Composition Animals Specific Pathogen free (SPF) C57BL6 female mice were used (25-35 g, 8-12 weeks). The animals were kept within a temperature and humidity controlled environment (22±2° C. and 60-80%, respectively), with a 12-hour light/dark cycle, with free access to water and food up to the moment of the experiment.

Induction of Murine Melanoma

Melanoma cells of the B16-F10 cell line were inoculated on day zero ($1 \times 10^6$ cells in 100 uL of culture medium per animal), subcutaneously (s.c.) in the back of the C57BL/6 male mice (Lee, Y. S., et al. Suppression of tumor growth by a new glycosaminoglycan isolated from the African giant snail *Achatina fulica*. European Journal of Pharmacology, 465: 191-198, 2003). The animals (n=8 per group, table 3) were treated from the 7th day (and every 4 days afterwards) with excipient (control), DECA, or DECA-IL2, as shown on the scheme on table 1. The DECA-IL2 group received also daily injections of IL-2 (20,000 UI, twice a day, subcutaneously). The tumor volumes were evaluated with the assistance of a digital caliper and determined ($mm^3$) according to the following formula: tumor volume ($mm^3$)=width×length× 0.5 (Lee, Y. S., et al. Suppression of tumor growth by a new glycosaminoglycan isolated from the African giant snail *Achatina fulica*. European Journal of Pharmacology, 465: 191-198, 2003). The volume of the solid tumor mass was evaluated every 3 days during the 28 day period after the injection of tumoral cells. The survival rate of the animals was evaluated for a period of 30 days after the injection of the tumoral cells.

TABLE 1

Treatment scheme

Start on the $7^{th}$ day and subsequently every 4 days
Control GROUP (Excipient)

$1^{st}$ Systemic saline - 24 intradermal injections of saline solution (NaCL 0.9% sterile) in pre-determined points in the dorsal and ventral regions.
$2^{nd}$ Intratumoral saline - two injections (one 0.02 mL injection at the center of the lesion and one 0.02 mL injection at the base of the lesion)
$3^{rd}$ Perilesional saline (6 application points - with the goal of circling the tumor)
DECA GROUP $1^{st}$ Systemic DECA - 24 intradermal injections of DECA solution (sterile) in pre-determined points in the dorsal and ventral regions. $2^{nd}$ Intratumoral DECA - two injections (one 0.02 mL injection at the center of the lesion and one 0.02 mL injection at the base of the lesion). $3^{rd}$ Perilesional DECA (6 application points).
DECA + IL-2 GROUP $1^{st}$ Systemic DECA - 24 intradermal injections of saline solution (NaCL 0.9% sterile) in pre-determined points in the dorsal and ventral regions.
$2^{nd}$ Intratumoral DECA - two injections (one 0.02 mL injection at the center of the lesion and one 0.02 mL injection at the base of the lesion)
$3^{rd}$ Perilesional DECA (6 application points - with the goal of circling the tumor)
$4^{th}$ Intratumoral IL-2 20,000 UI (0.02 mL injection at the center of the tumor)
$5^{th}$ Perilesional IL-2 20,000 UI (1 application point close to the region surrounded by the DECA application
$6^{th}$ Intraperitonial IL-2 20,000 UI OBS.: Daily from the $7^{th}$ day: 20 000 IU of intraperitoneal IL-2 (2x/day)

Results

The results demonstrated that 28 days after the inoculation of the tumoral cells the tumor volume reached its peak of 6,728.65±2,027.01 $mm^3$ (mean±SEM), with a 33.3% survival rate of the animals (3 of the 9 animals part of the study remained alive 30 days after the inoculation with the B16F10 cells) (FIG. 1). Despite the lack of a significant statistic difference, the group of animals that received the DECA treatment, on the $28^{th}$ day after the start of the model presented a tumoral mass of inferior volume, when compared to the control group (3,524.87±871.01 $mm^3$) and a survival rate of 50% (5 of the 10 animals part of the study). It's important to mention that although it's not significant, there was, on the $28^{th}$ day, a 47.6% inhibition on the tumor volume (when compared with the control group) and that the lack of significance may be the result of the standard error of the mean shown by the control group. For the DECA-IL-2 group, the results showed that the association was capable of reducing the tumor volume in a significant way from the $13^{th}$ day (57% inhibition) up to the $28^{th}$ day, when an approximately 67% inhibition was observed (2,198.36±450.39 $mm^3$) with a survival rate of 80% (8 of the 10 animals that were part of the study). Furthermore, the animals showed a good tolerance to the repeated treatment with IL-2. In clinical practice IL-2 is administered in a high dosage (600,000-720,000 UI/Kg) and the toxic symptoms observed are comparable to the induction of a controlled state of septic shock (low blood pressure, low systemic vascular resistance, liver and renal toxicity, beside pulmonary edema) (Rosenberg S A, Yang Y C, Topalian S L, et al. Treatment of 283 consecutive patients with metastatic melanoma or renal cell cancer using high-dose bolus interleukin-2. JAMA, 271: 907-913, 1994). The analysis presented on FIG. 1B corroborates the data of figura 1[4], showing that the volume reduction is related to the reduction of the tumor growth rate (for the DECA-IL-2 group).

Figure 2:
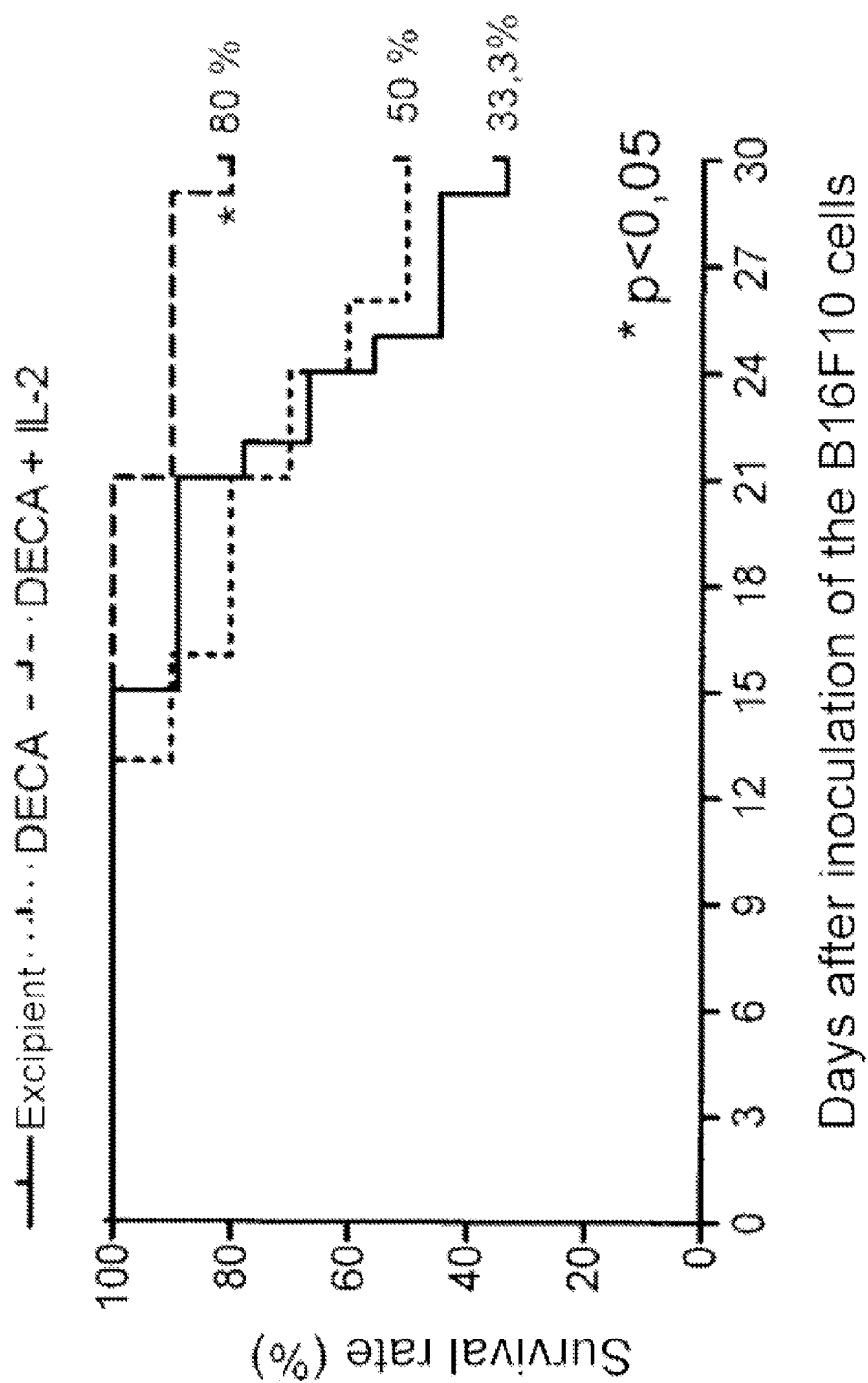
FIG. 2 shows the effect of treatment with DECA, DECA+ IL-2 on the survival of animals inoculated with murine melanoma cells. B16F10 cells were inoculated on day zero ($1\times10^6$; 100 μL/animal) subcutaneously (s.c.) on the back of C57B16 male mice. The graph represents the mortality curve and the percentage represents the animals which remained alive at 30 days after tumor cell inoculation. n=9-10 animals. * p, 0.05 (p=0.0361), Statistical Analysis: Logrank Test—Chi square.

Overall, the results demonstrated that treatment with the DECA-IL-2 combination, besides reducing the growth rate/tumor volume (FIG. 1) increased the survival rate of the animals when compared with the control group (excipient) (FIG. 2), suggesting it is beneficial for the treatment of melanoma.

Example 3

Treatment of Metastatic Malignant Melanoma in the Fourth Recurrence

Patient Data
Patient MBS, 46 years old, female.
Diagnosis
Metastatic malignant melanoma in the fourth recurrence, of Clark level III and Breslow of 1.32 mm$^2$ diagnosed on 16 May 2006.
Previous Convencional Treatment
a. First Surgical Oncologic Treatment
Surgery was carried out on 1 Jun. 2006, for the expansion of the margin at the site of the tumor with sentinel lymph node biopsy, which proved negative for malignancy. Complementary immunohistochemical pathologic examination of the lymph node showed the presence of micrometastases, the greatest of 0.17 mm, confirming, a posteriori, the diagnosis of metastatic and immunogenic malignant melanoma, by the presence of the antigen Melan A.
b. Second Surgical Oncologic Treatment
On 20 Feb. 2008 an extraction was performed of two superficial nodules suspected of recurrence in the left thigh, and the pathologic examination revealed a diagnosis of metastatic malignant melanoma. An extension of the surgical margin was then performed, with biopsy, of all the lesions operated on, on 9 Apr. 2008.
c. Third Surgical Oncologic Treatment
Eight months later (15 Oct. 2008) there was a second recurrence in the skin of the left thigh, which showed metastatic malignant melanoma, with a lesion coincident with the surgical margin. Again, an enlargement of the surgical margin was held, and in 27 Nov. 2008 a pathologic examination revealed no remnants of tumor in the surgical margin.
d. Fourth Surgical Oncologic Treatment
On 13 May 2010 a new lesion was diagnosed in the gluteal region, and surgically removed on 19 May 2010 without a freezing test. The new specimen showed metastatic melanoma with compromised surgical margins, indicating the third recurrence of the disease.
e. Results of the Fourth Surgical Oncologic Treatment, DECA Pre-Administration.
On 23 Jun. 2010 a PET/CT exam was performed which showed that it was a tumoral lesion, proving the fourth tumor recurrence. The short time in which the fourth recurrence formed from a residual lesion showed the aggressive nature of the metastatic cells.
DECA Pre-Administration Immunological Evaluation
The immunological evaluation consisted in part of in vitro blood tests (complete blood count, lymphocyte phenotyping, immunoglobulin dosage, RAST test (allergy), acute phase protein electrophoresis and of autoimmunity testing) and in vivo (delayed hypersensitivity primary and secondary test).

The delayed hypersensitivity tests were performed with a secondary battery of nine antigens (administered att 0.1 cc): 1) Koch's tuberculin 1:100,000; 2) PPD 20 UI/mL; 3) Staphylococcal toxin 1:100; 4) streptococcal toxin 1:100; 5) streptokinase/Dornase 40/10 UDS/mL; 6) Oidiomycin 1:100; 7) trichophytin 1:100; 8) *Escherichia coli* 1:100; 9) *Salmonella* spp. 1:100.

Tests for delayed primary hypersensitivity were performed using cutaneous DNCB 0.5% and 2% patches.

The result of the immunological evaluation expressed a change in the acute phase proteins, with an increase in ESR, CRP, alpha-1-acid glycoprotein, showing a systemic inflammatory effect from the tumor growth, after surgery, according to blood tests performed on 12 Jun. 2010.

The evaluation of primary hypersensitivity proved to be abolished. The secondary systemic delayed hypersensitivity showed a decrease of +/++ to +++++ for intracellular antigens and a normal ++/++++ to other antigens, at a distance from the tumor. In areas of relapses all antigens showed a much reduced response of 0/+ for intracellular antigens and of +/+++ to +++++ to other antigens. In the peritumoral region the reaction proved to be virtually abolished, with 0/0 for intracellular antigens and 0/+ to other antigens.

These results, of the delayed secondary hypersensitivity, also showed a significant immunosuppression.

Treatment with DECA
Started on 26 Jun. 2010 and ended on Apr. 8, 2010 in the waiting period for the release of the health insurance arrangements for surgery. The immunotherapy treatment was carried out with the free and informed consent of the patient. The DECA immunotherapy was carried out as follows:

Application of 1.8 cc of the antigenic composition divided into 2 applications of 0.9 ml near the 10 major lymphatic territories.

3-4 cm distance margin between applications to facilitate the reading of the evolution of the treatment at an interval of 4±1 days.

Administration of nine extra 1.8 cc perilesional sets, in two applications of 0.9 cc per set, bypassing the scars of the primary tumor's surgery, of the second and third recurrence, as well as the region of the fourth and fifth recurrence, also with an interval of 4±1 days.

Based on the evaluation of the second application, a joint intratumoral application was made with a volume equivalent to ten compositions of 1.8 ml.

Application of recombinant human interleukin-2 at low doses, at a receptor saturation level with a concentration of 1 to 2 million units per meter of body surface located at 5 cm from the lesion. For the patient, 1 million units were applied daily, subcutaneously. In the days of the antigen application, after the application, two extra doses of 1 million units were given, one in the intraperilesional region and another in the intratumoral area. On these occasions these applications totaled 3 million units, still within the limits of the recommended low dose by body surface.

Thus, up to the time of surgery, 11 sessions of systemic and perilesional immunotherapy were applied, from 24 Jun. 2010 to 2 Aug. 2010, and also 5 concurrent intratumoral applications at a 4±1 day interval, or one day after the systemic and perilesional applications.

It is interesting to mention that the Doppler ultrasound examinations (on 19 Jul. 2010 and 4 Aug. 2010) suggest the transformation of the tumor into an inflammatory area with no angiogenesis.

Evaluation of the DECA Immunotherapy Treatment

On the fifth surgery on 5 Aug. 2010, the frozen section exam showed no tumor in the treated area, which underwent only a conservative removal of the inflammatory lesion.

Result of the DECA Immunotherapy Treatment

The postoperative pathological examination on 5 Aug. 2010 showed the presence of palisading granuloma with central necrosis, skin with dense chronic inflammatory infiltrate involving the foreign body of the giant cell granuloma described above, absence of residual neoplasia and cancer-free surgical margins.

Figure 3:
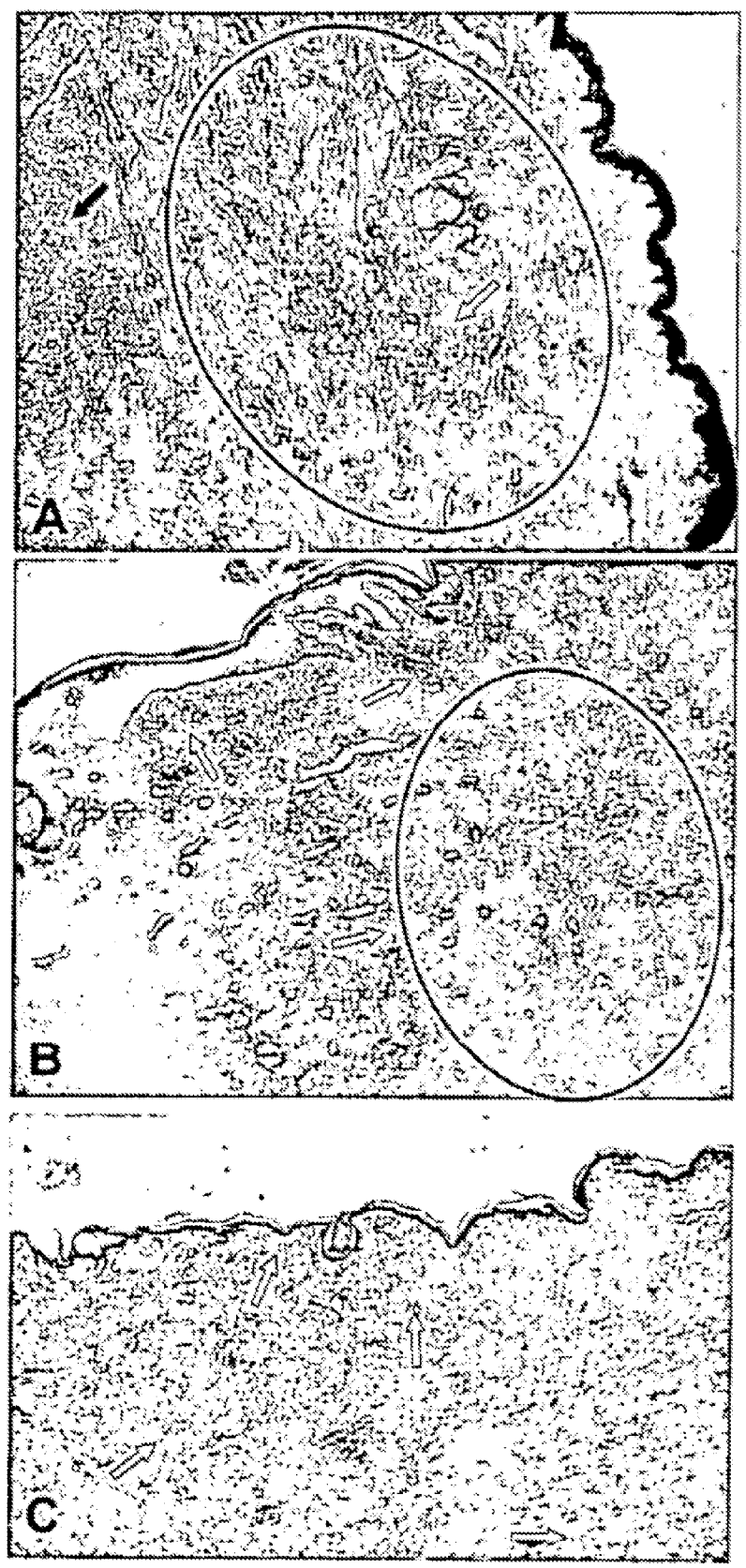
FIG. 3 shows the anatomopathological exams of volunteer "MBS". A. Pre-immunotherapy treatment examination, the black arrow indicates the tumor region and the white arrow absence of inflammatory infiltrate. The region outlined in black illustrates the inhibition of the immune system by tumor detected by the absence of inflammatory infiltrate. B. Immunological post-treatment examination, where the complete elimination of the tumor can be seen, the white arrows indicate the dense inflammatory infiltrate and the area enclosed in black exemplifies areas of fibrosis and reparative changes permeated by inflammatory infiltrates. C. Recontextualization of the immune system by the use of the present invention, attested by the positive reaction to S-100 in countless intra-epidermal dendritic cells (indicated by arrows) and amid the dermal inflammatory infiltrate extending into the deep dermis without melanocytic cells or residual melanoma.

The immunohistochemical examination revealed the complete absence of tumor cells from the surgically removed tissue previously treated with DECA according to the limits of available diagnostic techniques (FIG. 3).

After the first two applications of the protocol described above, the patient recovered from the observed immunosuppression, evidenced by the normalization and hyperactivation of all the application points of the immunotherapy, like a normal patient. These results demonstrate the recovery of the patient's T loop and of the whole TH1 profile cell immunity that was overwhelmed by the tumor. Concomitantly, the immunotherapy generated an inflammatory process involving the entire tumor, completely necrotizing it and eliminating it as shown by the ultrasound exams and proven by histological examination.

From 7 Aug. 2010 to 30 Nov. 2011 the patient was treated in the same systemic and perilesional way, twice a week and with a recombinant human interleukin-2 dose below the receiver saturation level, with 600,000 units daily. Since then, the patient receives a weekly administration of antigens and a daily administration of interleukin 2. Thus, the patient has been tumor free for 18 months.

Conclusion of the Case

The evaluated data and clinical outcome of patients, so far, strongly suggest that the immunotherapy with the immunogenic compositions of the present invention was responsible for the elimination of the tumor.

Example 4

Fighting a Malignant Melanoma

Patient Data

Patient PPC, 62 years old, male.

Diagnosis

Malignant melanoma of Clark level II and Breslow 1.2 mm$^2$ diagnosed on 2 Feb. 2011.

Previous Treatments

In this case no prior treatment was performed because the DECA immunotherapy was performed before cancer surgery of the primary tumor after the application of the term of free and informed consent.

DECA Pre-Administration Immunological Evaluation

As there was no time for a prior immunological assessment because of the need to have the surgery in the shortest time possible, this evaluation was performed by reading the antigens applied during the DECA treatment.

Pre-Oncological Surgery DECA Treatment

In the preoperative period (10 Feb. 2011 to 17 Feb. 2011) treatment of the patient was started on the following basis:

Application, along the 10 major lymphatic territories, of 1.8 cc of formulation 1 or DECA, divided into 2 applications of 0.9 cc.

3-4 cm distance margin between applications to facilitate the reading of the evolution of the treatment at an interval of 4±1 days.

Administration of 2 extra 1.8 cc sets of DECA divided into two applications 0.9 cc for each composition, bypassing the tumor melanoma on the first day of treatment.

Intratumoral application of five DECA compositions of 1.8 cc each, with a final volume of 9.0 cc.

Application of low doses, at a receptor saturation level with a concentration of 1 to 2 million units per m$^2$ of body surface located at 5 cm from the lesion. For the patient, 1 million units were applied daily, subcutaneously.

Thus, by the time of surgery, 2 sessions of systemical immunotherapy, 1 session of perilesional immunotherapy, and 1 session of intratumoral immunotherapy were applied, these latter two being applied on the first day of treatment. A daily application of recombinant human interleukin-2 was associated to this treatment, in the dosage and manner described above.

Result of the Pre-Oncological Surgery Immunotherapy Treatment with DECA

In this 8 day period of therapy, the patient responded well to the immune treatment with total regression of the malignant melanoma. The lesion in the tumor transformed part progressed with an intense local inflammatory process that necrosated and disappeared giving way to the inflammatory process described in surgical pathology. It is necessary to mention that the patient showed during this period: episodes of high and low fevers and intense inflammatory ipsilateral inguinal adenopathy.

Conventional Surgical Cancer Treatment

A complete excision of the primary tumor was proposed, with a wide surgical margin of safety, with intrasurgical sentinel lymph node survey.

Conventional Oncological Surgery of the Primary Tumor

On 18 Feb. 2011 the patient was operated on and a complete excision of the tumor was performed, with a wide margin of safety, and the survey of two satellites nodes revealed negative for malignancy. For this reason the ganglion draining was not performed.

Results of the Conventional Oncological Surgery of the Primary Tumor

Pathological examination confirmed complete tumor regression stating:

on the skin: inflammatory changes with an ulceration area covered by a fibrin-leukocyte cap, presenting an exuberant granulation tissue at the base with mixed inflammatory infiltrate. This infiltration permeates and extends throughout the epithelium at the edges of this ulcer, also with multinucleated giant cells of a foreign body type. The whitish domed region described in the microscopy corresponds to a seborrheic keratosis of the papillomatous type with acanthosis, hyperkeratosis and papillomatosis of the epidermis. All the skin was subjected to a histological examination with no residual melanocytic neoplasia being found.

in the sentinel lymph node I: extensive fibrosis of the hilar region and subcapsular and sinus histiocytosis, with no metastatic deposits being identified by morphological examination;

in the sentinel lymph node II: histological findings similar to those described in I, not having metastatic deposits in the morphology.

On this date the immunohistochemical examination of sentinel nodes I and II showed no melanoma micrometastases.

Figure 4:
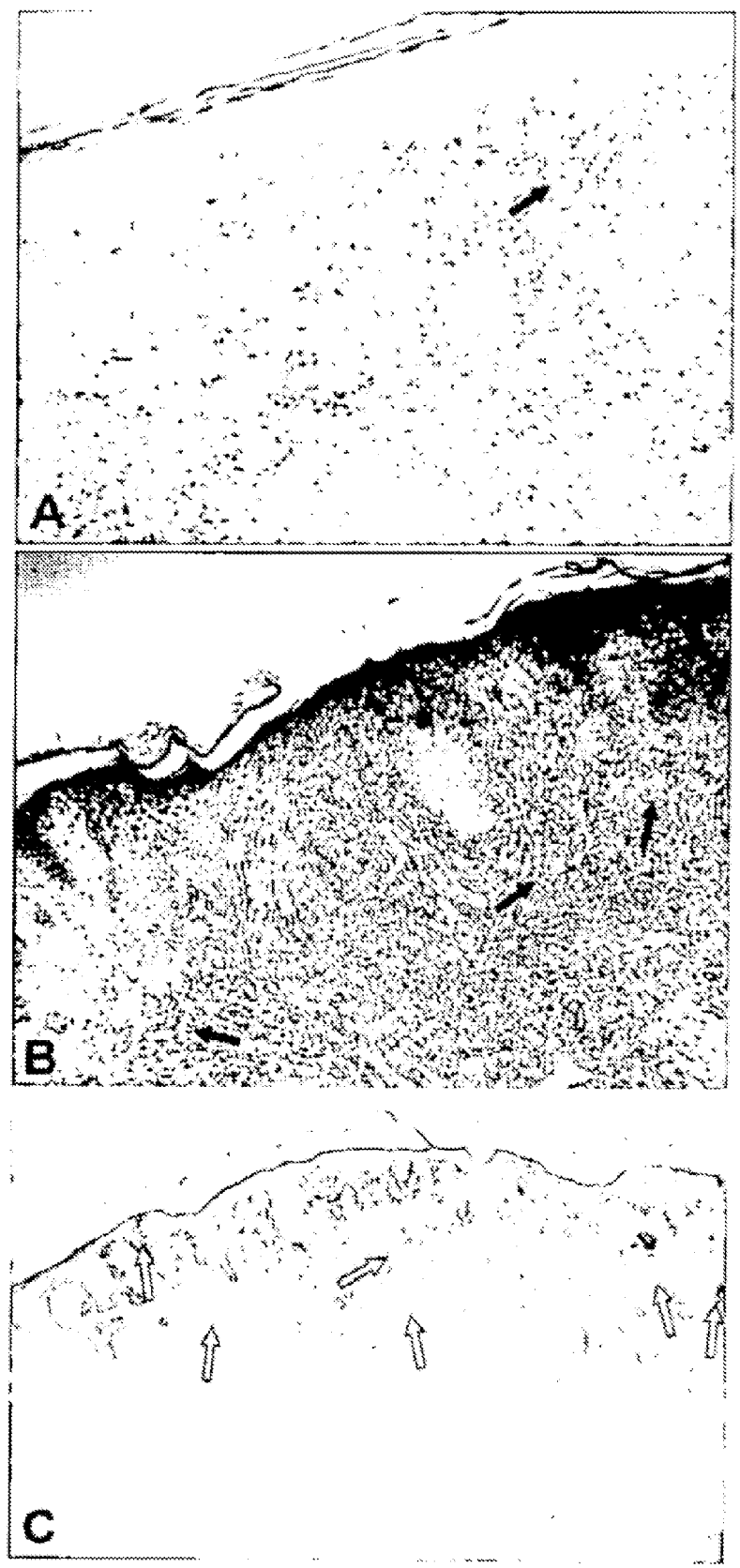
FIG. 4 shows the anatomopathological exams of volunteer "PPC". A. Pre-immunotherapy treatment examination showing area of aggressive metastatic melanoma with some pigmented cells, and scarce and mild inflammatory peripheral infiltrate indicated by the arrow, confirming the inhibition of the immune system by tumor. B. Post immune therapy examination illustrating the disappearance of the tumor and replacement by intense and dense inflammatory infiltrate. C. Recontextualization of the immune system by treatment with the present invention, attested by the positive reaction to S-100 in countless intra-epidermal dendritic cells (indicated by arrows) and amid the dermal inflammatory infiltrate extending into the deep dermis without residual melanoma.

The immunohistochemical examination of the primary tumor revealed complete absence of tumor cells on surgically removed tissue previously treated with DECA according to the limits of available diagnostic techniques (FIG. 4).

Pre-Oncologic Surgery Results of the DECA Treatment of the Primary Tumor

These data produced by surgery within the context and limitations of diagnostic techniques available, showed surprising results by not detecting the primary tumor after treatment with DECA immunotherapy.

Post-Oncologic Surgery DECA Treatment

With this complete tumor regression result the immune treatment was continued on the following bases:

Application, along the 10 major lymphatic territories, of 1.8 cc of the DECA composition divided into 2 applications of 0.9 cc.

3-4 cm distance margin between applications to facilitate the reading of the evolution of the treatment at an interval of 4±1 days.

Administration of two extra perilesional compositions of 1.8 cc each, with two applications of 0.9 cc per composition, bypassing the large surgical scar with no space between them, also with an interval of 4±1 days Daily application of human recombinant interleukin 2 in low doses, at a receptor saturation level with a concentration of 1 to 2 million units per of body surface located at 5 cm from the surgical scar. 1 million units per $m^2$ of body surface per application were used for the patient.

Post-Oncological Surgery Results of the DECA Treatment

The surgical area of the removal of the satellite nodes in the inguinal region evolved with the formation of a fluid collection, confirmed on 16 Mar. 2011 by ultrasonography that showed: simple cystic formation with 6.0×5.2×3.1 cm, with blurring of adjacent fat planes and no abnormal vascularization or tumor type vascular alterations were observed by color Doppler.

This collection described above evolved with local inflammatory process, reducing its size and increasing the inflammatory adenopathy detected by ultrasonography on 28 Mar. 2011. No abnormal vascularization in this formation was detected by color Doppler. Regarding the exam on 16 Mar. 2011 it is noted: 1) marked reduction of the formation that previously had a cystic aspect, suggesting significant reabsorption, organization and favoring an inflammatory/reactive hypothesis (post-surgical collection); it was also observed in the region of the left inguinal lymph nodes 2) increased size of the lymph nodes, preserving a vascularized hilum and a reactive aspect, situated medial and proximal to the aforementioned formation measuring 1.6×0.8 cm and 2.4×1.7 cm.

The immunological treatment was continued until 31 Jul. 2011, and the physical examination revealed complete regression of the lesions and a transformation of an intense regional lymphadenopathy reaction into a residual regional lymphadenopathy reaction.

On the 5 and 8 Jul. 2011, the repetition of the PET/CT and of the soft-tissue "doppler" color ultrasound, of the left leg and of the left inguinal region, respectively, confirmed the inflammatory nature and complete regression of the lesions, leaving only the residual reaction inflammatory adenopathy. There was also a regression of the diffuse increase in metabolic activity in the bone marrow of the axial and appendicular skeleton, showing an effect of bone marrow stimulation by DECA, in the renewal of the immune response, which demonstrates its ability to stimulate and regenerate tissues.

Discussion of the Results of the DECA Treatment, Pre- and Post-Conventional Oncological Surgery It is a case of malignant melanoma of approximately 1 cm, which underwent a single biopsy without surgical treatment. This tumor was the target of an immunotherapy treatment with a battery of 9 antigens associated with reduced doses of recombinant human interleukin-2 as described above. This treatment caused an intense inflammatory reaction involving the entire lesion, leading to necrosis and ulceration of the whole tumor area that disappeared within 8 days of the treatment.

After this period the patient underwent surgery and the pathological examination confirmed the replacement of tumor tissue with ulceration with a total absence of tumor cells, surrounded by intense inflammation with characteristics of foreign body granuloma (FIG. 4B).

Pathological examination of two sentinel lymph nodes proved the reactive lymphoid hyperplasia with an intense and subcapsular sinus histiocytosis, and extensive fibrosis of the hilar region, no metastatic deposits being identified. The immunohistochemical examination confirmed the finding confirming the absence of micrometastases in these lymph nodes.

The region from where the satellite lymph nodes were removed evolved with the formation of a fluid collection shrouded in an inflammatory process with increased reactional inflammatory locoregional lymphadenitis showing a good immune response. With continued treatment, an intense inflammatory process surrounded this fluid collection causing its regression and absorption, accompanied by a non-tumoral inflammatory reaction of the satellite lymph nodes.

The ultrasonography Doppler exams and the PET-CT demonstrate the suggested the nontumorous inflammatory aspect by proving the absence of a tumor mass. These tests show that the intense regional lymphatic reaction and increased bone marrow activity demonstrate a strong and effective anti-tumor immune response.

Conclusion of the Case

The evaluated data, and the clinical outcome to date, strongly suggest that the immunotherapy using the compositions of the present invention, as the only treatment used in pre-cancer surgery of the primary tumor, was responsible for the observed tumor elimination in 8 days.

Example 5

Fighting an Advanced Microtubular Gastric Adenocarcinoma with Peritoneal Carcinomatosis and Intra-Abdominal Lymphatic Metastatic Spread Patient Data
Patient R-M, 72 years old, male.
Diagnosis
Advanced microtubular gastric adenocarcinoma with peritoneal carcinomatosis and intra-abdominal lymphatic metastatic spread.

Performed Tests a. Conventional Upper Gastrointestinal Endoscopy and Pathological Upper gastrointestinal endoscopy on 12 Jun. 2008 showed an advanced and stenosing gastric antrum neoplasm confirmed by pathological examination on 13 Jun. 2008, and the biopsy showed:

b. Conventional Imagiology

Figure 5:
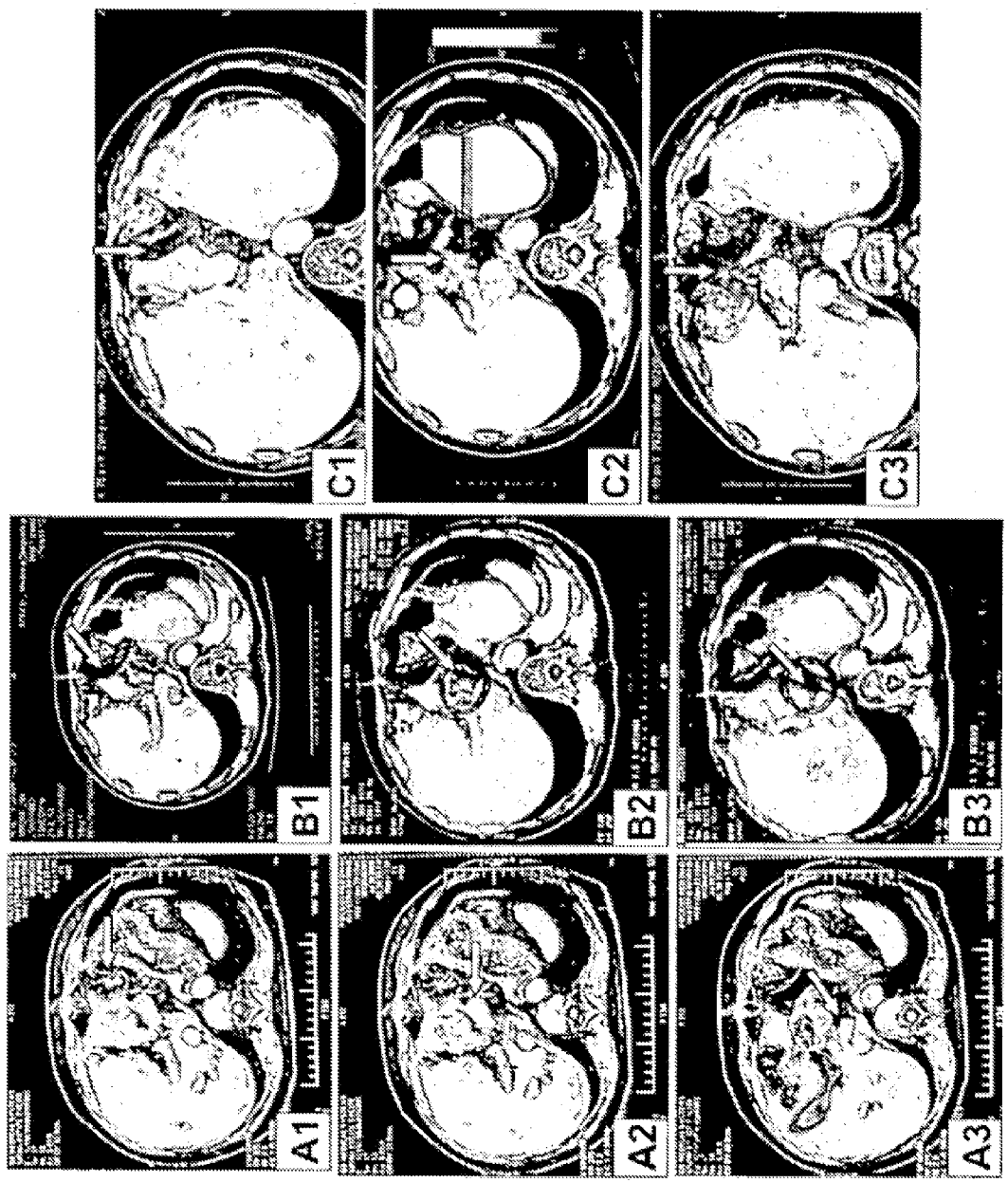
FIG. 5 shows Nuclear Magnetic Resonance Examinations (A1, A2 and A3 pre immunological treatment in 30 Jul. 2008) and CT scans (B1, B2, B3 after treatment in 13 May 2009, C1 and C3 post treatment in 30 Aug. 2011 and C2 after treatment in 13 Apr. 2010) of the patient R-M. A1 carcinomatosis showing thickening of fat (arrow). A2. Celiac trunk lymph node cluster (arrow; largest measuring 3.7 cm). A3. Hepatogastric ligament lymph node cluster measuring 4 cm (arrow). B1 Disappearance of carcinomatosis, by showing the disappearance of the thickening of fat (arrow). B2. Reduction of the biggest node (3.7 cm to 1.4 cm) in the celiac trunk lymph node cluster (arrow). B3. Disappearance of the hepatogastric ligament lymph node cluster (arrow). C1. Disappearance of the carcinomatosis (arrow). C2. Reduction of the biggest node (1.4 cm to 1.1 cm) in the celiac lymph node cluster (arrow). C3. Confirmation of the disappearance of the hepatogastric ligament lymph node cluster (arrow). These data show a complete remission of malignant peritoneal carcinomatosis and lymphatic dissemination of gastric cancer with the combination of immunotherapy with the present invention associated to palliative radio and chemotherapy.

On 20 Jun. 2008 a preoperative tomography abdomen and pelvis was done for checking the stage of the gastric cancer, with the conclusion that it was an advanced gastric carcinoma with peritoneal carcinomatosis by disseminating continuity and extensive lymphatic nodes in multiple areas measuring 4 cm the largest of them (FIG. 5, A1-A3).

c. Postoperative Immunological Evaluation

The first consultation was held on 23 Jul. 2008 after surgery, and conventional tests and immunological evaluation on 24 Jul. 2008.

Traditional tests showed a mild microcytic anemia (Hb=11.7 g/dL (NV=13-18 g/dL, HT=37.1% (NV=40-54%) and VCM=70 $U^3$ (NV=80 to 97 $U^3$) and hyperthrombocytosis (755,000 (NV=150,000 to 450,000/mm$^3$)), lymphocytosis (9.100/mm$^3$ (NV=4,000 to 11,000/mm$^3$), hyperglycemia (155 mg/dL (NV=up to 99 mg/dL), elevated ESR 110 mm/h, elevated uric acid (7.3 mg/dL (NV=up to 7.0 mg/dL), elevated CRP (0.6 mg/dL VN which is up to 0.5 mg/dL), high alpha-1-acid glycoprotein (141 mg/dL (NV=up to 140 mg/dl) and elevated amylase with 170 U/L (NV=25 to 125 U/L).

The immunological evaluation was performed after surgery with the following in vitro tests (blood tests) and in vivo (primary and secondary hypersensitivity).

In vitro tests consisted of; dependent T immunoglobulin levels that appear adjacent to the maximum normal values (Ig A 324 (NV=82-453), Ig G 1476 (NV=751-1560), IgM 200 (NV=46-304) and Ig E 61.89 (NRV=100)), RAST negative to all tests, beta-2 microglobulin 2496 (NV=up to 2030) normal immunophenotyping of $CD3^+$ T lymphocytes, with normal $CD4^+$ cells (43.3% (845/mm$^3$) NV=27-57% (560 to 2700/mm$^3$)), decreased $CD8^+$ in absolute and relative values (242/mm$^3$ NV=14-34% (330-1400/mm$^3$) and a high $CD4^+/CD8^+$ ratio (3.49 VN=0.98 to 3.24).

In vivo tests:
delayed primary hypersensitivity: tested with a cutaneous patch of 0.5% and 2% DNCB.
delayed secondary hypersensitivity.
The results showed:
primary hypersensitivity proved to be abolished.
systemic secondary delayed hypersensitivity showed decreased 0/+ in +++++ for intracellular antigens and decreased +/++ to other antigens, at a distance from the tumor. In the pericicatricial area all antigens demonstrated an abolished the reaction of 0/+ for intracellular antigens and 0/+ in +++++ to other antigens.

These in vivo and in vitro tests, showed a significant immunosuppression of the Th1 profile cellular immunity, primary and secondary, local and systemic, which is responsible for antitumor immunity and elimination of tumor cells and tumor escape mechanism by Th2, with an antibody response rather than a cellular response. The primary immunosuppression with loss of integrity of the T loop and without the possibility of drafting a new T response, coupled with the breakdown of cellular immunity profile TH1 responsible for anti-tumor immunity and prevalence of the antibody escape response instead of cell response showed a compromised immune system, overwhelmed by the tumor without chances of containing the disease by itself.

d. Diagnostic Conclusion

Stenosing advanced microtubule gastric adenocarcinoma with peritoneal carcinomatosis by contiguous spread and extensive lymphatic metastatic spread in multiple lymphatic territories with the biggest one measuring 4 cm.

Treatment e. Conventional Surgical

The treatment (on 11 Jul. 2008) was a partial gastrectomy with a B2 palliative reconstruction with parcial lymphadenectomy.

The pathology of the partial and palliative gastrectomy and lymphadenectomy of 11 Jul. 2008 showed extensive remaining advanced neoplastic disease.

f. Conventional Chemotherapy and Radiotherapy

Because it was an advanced gastric carcinoma with peritoneal carcinomatosis and intra-abdominal lymphatic spread without possibility of cure by surgery and chemotherapy, radiotherapy was proposed, combined with non curative chemotherapy with 5-fluorouracil and taxotere in cycles of 21 days for control of the tumor mass and to improve both the quality of life and the survival chances of the patient. This chemotherapy was conducted from 14 Aug. 2008 to 26 Dec. 2008. The 25 radiotherapy sessions started on Oct. 10, 2008 and ended on 13 Nov. 2008.

g. Treatment with DECA

For the above reasons it a combination of immunotherapy with the palliative chemotherapy was proposed to improve the patient's conditions and for possible beneficial results of this pharmacological association.

Immunotherapy was performed one week (two applications of DECA) before the start of the chemotherapy and continued in the second and third weeks after the first week and at each 21 day cycle of chemotherapy. Thus, chemotherapy remained uninterrupted, whereas the immunotherapy was performed for a period of 2 weeks with a 1 week interval.

DECA Protocol was Performed as Follows:
Application of 1.8 cc of the DECA composition in two applications of 0.9 cc to 10 of the major lymphatic territories.
3-4 cm distance margin between applications to facilitate the reading of the evolution of the treatment at an interval of 4±1 days.
From the avaliation of the $4^{th}$ application, at which time all responses normalized, becoming hyperergic.
Application of recombinant human interleukin-2 at low doses, at a receptor saturation level with a concentration of 1 to 2 million units per m$^2$ of the patient's body surface at 600,000 units daily, applied near the surgical scar.

h. Results of the Treatment i. Conventional

The conventional treatment alone (surgery) was performed in palliative way to solve the patient's gastric obstruction.

ii. Treatment with DECA Associated with Chemotherapy

The delayed primary hypersensitivity tests of the patient normalized in one month and the delayed secondary hypersensitivity in two weeks showing a recovery of the T loop cellular response. In two weeks, the signs and symptoms of systemic inflammation and infection disappeared.

The patient was reassessed after six months of DECA treatment and associated chemotherapy (started respectively on 6 Aug. 2008 and 14 Aug. 2008). After six months (9 Feb. 2009) of immunological treatment and associated chemotherapy there was:
a significant reduction of most of the adbdominal lymphadenomegaly;

a significant reduction in the signs of carcinomatosis.

a complete remission of immunosuppression with positivization, after 4 weeks of treatment, of the secondary delayed hypersensitivity reading showing a positive reaction for 3+/4+ in 5+ to the 9 previously tolerated antigens. The primary delayed hypersensitivity previously abolished became positive, also after 1 month of treatment.

After 9 months (13 May 2009) of the above mentioned treatment there was:

reduction of the lymphadenomegaly of the celiac trunk from 2.0-1.6 cm to 1.4 cm without further lymphadenomegaly (FIG. 5, B2-B3).

attenuation of the fibrocicatricial aspect showing disappearance of the signs of carcinomatosis (FIG. 5, B1).

unchanged left pleural effusion.

After 1 year and 2 months (3 Oct. 2009) of the above mentioned treatment there was:

Significant reduction of the left pleural effusion;

reduction of the celiac trunk from 1.4 cm to 1.3 cm without further lymphadenomegaly Mitigation of the fibrous scarring change of the surgical cavity.

After 1 year and 8 months (13 Apr. 2010) of the above mentioned treatment there was:

resolution of the left pleural effusion.

unchanged lymphadenomegaly of the celiac trunk (FIG. 5, C2).

After 1 year and 11 months (31 Jul. 2010) of the above mentioned treatment there was:

reduction of the celiac trunk from 1.3 cm to 1.1 cm without further lymphadenomegaly.

Complete disappearance of liver nodules;

After two years and four months (18 Feb. 2011) of the above mentioned treatment there was:

unchanged torax.

Maintenance of the celiac trunk lymph nodes measuring 1.1 cm.

Conclusion of the Case

Association of radio, chemo and immunotherapies conducted from August to December 2008 brought: complete remission of immunosuppression and a significant reduction of both the carcinomatosis and of the lymphadenomegaly in the upper abdomen. The liver nodules and enlarged lymph nodes of the celiac trunk remained, the largest at 1.6 cm.

From this assessment, immunotherapy was instituted exclusively until February 2012. As a result of this treatment it can be observed: complete remission of the suspicious liver nodules, disappearance of signs of carcinomatosis and significant reduction of the lymph nodes from 2.0-1.6 cm to 1.1 cm.

These data strongly suggest that immunotherapy was effective as an adjunct to radiotherapy and chemotherapy, and when applied alone was effective for the induction and maintenance of tumor remission after 3 years and 6 months of treatment (FIG. 5, C1, C3).

Example 6

Combat to a Multiple Inflammatory Pseudotumor Related to Human Herpes Virus Type VIII Patient Data
Patient A-D, 40 years old, female.
Diagnosis
Multiple inflammatory pseudotumor related to human herpes virus type VIII.

Clinical History a. Clinical Summary

In a consultation on 4 Jun. 2006, presented a history of evening fever (between 37.5 to 37.8° C.), headache, fatigue and dyspnea on mild exertion. At the clinical examination the patient was febrile, adynamic, somewhat prostrate, with sparse rhonchi in both lungs and significant hepatosplenomegaly.

b. Performed Tests

Conventional Blood Tests

Laboratory tests on 5 Oct. 2006 showed an infectious/inflammatory scenario: ESR=41 mm (NV<=10 mm), PCR=3.83 mg/dL (N=<0.50 mg/mL), alpha-1-acid glycoprotein=I, 66 mg/dL (N=50 to 120 mg/dL), hypocalcemia Ca 2+=7.4 mg/dL (N=8.6 to 10.3 mg/dL), mild thrombocytopenia with platelet count of $143.000/mm^3$ (NV=150,000 to 450,000 $mm^3$), proteinuria 0.66 g. On 5 Oct. 2006 the serological survey was negative for the following etiologic agents: Toxoplasmosis, Dengue fever, brucellosis, HIV, hepatitis by virus: A, B and C; *Paracoccus* spp, *Histoplasma* spp., The direct PCR antigen survey was negative for *Cryptococcus* spp. and *Histoplasma* spp. Serology showed previous infection for Cytomegalovirus, EBV (mononucleosis) and Rubella. While the test for the IgM herpes virus was positive. This condition is related to herpes virus type VIII and cross-reactivity between this type with I and II suggests infection with human serotype VIII.

Conventional Imagiology

Figure 6:
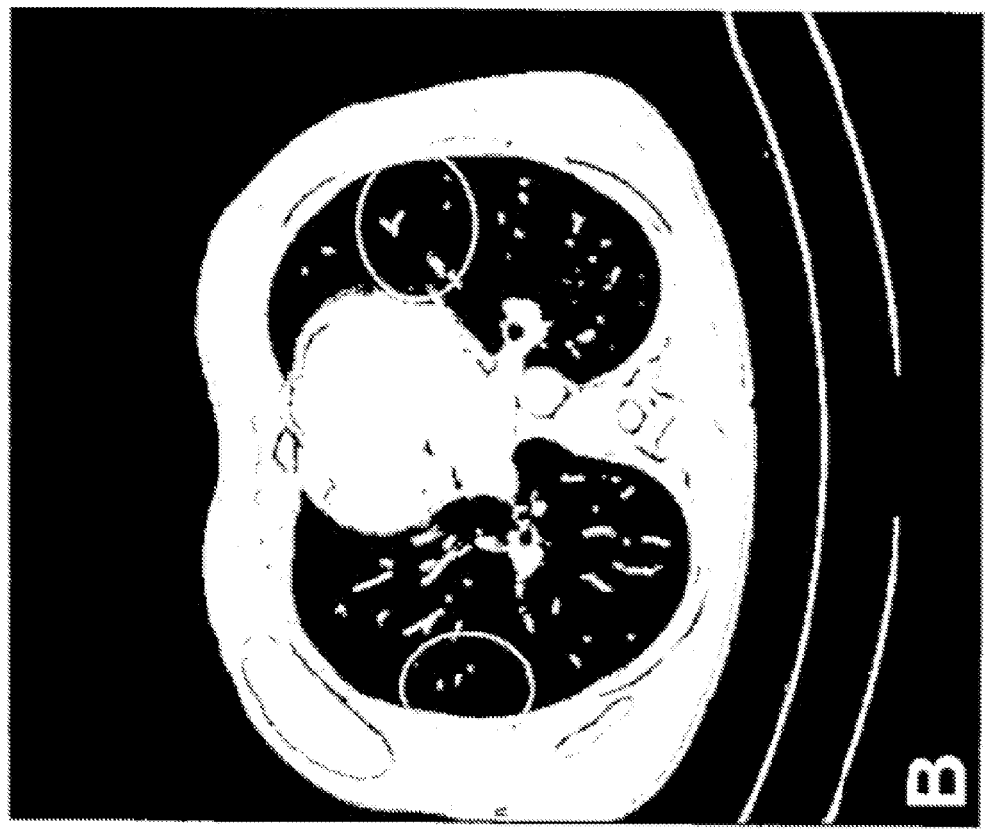
FIG. 6 shows CT scans examinations of the chest and abdomen of the volunteer A-D. A. Pre immunotherapy treatment exam held on 9 Oct. 2006 identifying tumors in the areas indicated with circles. B. Post immune therapy exam in 11 Dec. 2006 evidencing the absence of these tumors in the areas analyzed.
Figure 6:

A computerized tomography of the torax on 9 Oct. 2006 revealed: multiple bilateral pulmonary nodules of up to 3.0 cm, an irregular area of tumoral aspect of 5.0 cm in the left apex, right air bronchogram and a lump in the RML adhered to the pleura (FIG. 6A). Tomography of the abdomen confirmed an important contemporary hepatosplenomegaly with multiple nodes across the root of the mesentery, liver nodules and splenic nodules. It was also found a scenario of maxillary sinusitis and edema and hypertrophy of nasal passages.

Conventional Pathological

The pathology proved complex showing an inflammatory process with lots of histiocytes. The survey was sent to one lung specialist. The analysis of the histopathologic diagnosis of a rare disease: inflammatory pseudotumor.

Immunological Evaluation

The immunological evaluation was held on 5 Oct. 2006 with the following in vitro tests (blood tests) and in vivo tests (primary and secondary hypersensitivity).

The in vitro tests showed the following clinical situation: normal immunoglobulin dosage (Ig G, Ig A, Ig E), total complement and C3 and C4 according to normal standards, immunophenotyping of total $CD3^+$ T lymphocytes diminished in absolute numbers ($715/mm^3$–normal minimum=$1035/mm^3$) indicating T lymphopenia, with normal $CD4^+$ (54% ($551/mm^3$) NV=35-62% (535 to $2580/mm^3$)), decreased $CD8^+$ in absolute values ($163/mm^3$ NV=17-43% (255 to $1720/mm^3$) and a high $CD4^+/CD8^+$ ratio (3.4 NV=0.9 to 2.6).

These results showed humoral immunity and of the normal complement system, however, non-reactive, i.e. not involved in the immunological response to the ongoing infection. Immunophenotyping demonstrated an ongoing T lymphopenia and T response due to the high $CD4^+/CD8^+$ "(helper cells predominated over the suppressor/cytotoxic cells). The infectious agent caused a polarization for a response of the TH1cell type.

In vivo tests:
delayed primary hypersensitivity: Performed with skin patches of 0.5% and the 2% DNCB
delayed secondary hypersensitivity.

The results showed:
primary hypersensitivity proved to be abolished.
delayed systemic secondary hypersensitivity showed as decreased.

The conclusion of the immunological assessment: tests in vivo and in vitro showed that the infectious agent caused a polarization towards a T cell response of the TH1 type. This response has been shown ineffective with lymphopenia and T loop rupture by the abolition of the delayed primary hypersensitivity indicating inability to perform a new primary response and delayed secondary hypersensitivity showing a decreased cellular memory and compromised effector loop.

Diagnostic Conclusion

Multiple inflammatory pseudotumor (associated and related to human herpes virus type VIII) with associated with T immunosuppression.

Treatment

Conventional

Surgical intervention constitutes an effective form of treatment and etiology is related to the herpes virus VIII which explains the cross-reactivity with the positive IgM for herpes virus I and II. Cases of recurrence after surgical resection have been described. In this case, in which there are multiple pulmonary nodules, abdominal nodules (at the root of the mesentery) and hepatosplenomegaly with inflammatory systemic hypocalcemia, there were no similar reports in the scientific literature. Therefore, the surgery cannot be curative. It is possible to infer that the observed major T immunosuppression may have contributed to the unusual and multiple form of a rare disease.

Treatment with DECA

Due to the observed immunosuppression and the impossibility of surgical treatment (because of the multiple foci), with the free and informed consent it was decided to treat this immunosuppression with DECA, for a period of approximately two months, after which the patient was to be reevaluated. The protocol consisted of:

Application of three DECA compositions of 1.8 cc divided into two applications of 0.9 cc per composition, in the abdomen, and two 1.8 cc of DECA divided into two applications of the composition of 0.9 cc, respectively, in each upper right and left limbs, with 0.9 cc in the arm and 0.9 cc in the forearm bilaterally next to the 10 main lymphatic territories.

3-4 cm distance margin between applications to facilitate the reading of the evolution of the treatment at an interval of 7±2 days.

Application of recombinant human interleukin-2 at low doses, at a receptor saturation level with a concentration of 1 to 2 million units per $m^2$ of the patient's body surface at 600,000 units daily, applied in the abdomen.

I. Treatment Results

I. Conventional

In this case there were no therapeutic alternatives, as the surgery would not be effective against multiple manifestations of the disease.

II. Treatment with DECA

The patient normalized the delayed primary hypersensitivity test results in a month and the delayed secondary hypersensitivity in two weeks, demonstrating a recovery of the T loop cellular response. In two weeks, the signs and symptoms of systemic inflammation and infection disappeared.

After two months of treatment the patient was reevaluated. On physical examination, the patient had no signs of infection or inflammation; there was a regression of the hepatosplenomegaly. Computer tomography of the chest and abdomen held on 11 Dec. 2006 showed:

Lungs: tenuous ground glass opacities in the right apex sutures (surgical sequelae), disappearance of multiple sparse nodular opacities in both lungs (complete remission of the pulmonary inflammatory and infectious process) and complete regression of the right hilar lymph node (FIG. 6B)

In the abdomen: complete remission of hepatosplenomegaly, and a significant reduction in the mesenteric lymph nodes.

Conclusion of the Case

After the treatment period (from 15 Oct. 2006 to 11 Dec. 2006) with DECA was: complete regression of hepatosplenomegaly, of the multiple pulmonary abdominal nodules and mesenterial lymph node normalization, as well as of the clinical signs of systemic inflammation and infection in the 11 Dec. 2006 examinations. There was also complete remission with immunosuppression positivization after 2 weeks of treatment, the reading of delayed hypersensitivity showing a positive reaction of 3+/4+ in 5+. The previously abolished delayed primary hypersensitivity became positive after 1 month of treatment. These results showed a complete remission: clinical, laboratory and of imaging of the inflammatory pseudotumor, as well as of the immunosuppression scenario presented by the patient, by the use of the proposed treatment. The patient is without signs of disease or relapse for 5 years and 3 months.

Example 7

Fighting an Acinar Adenocarcinoma, Gleason Grade 7 (4+3) Adenocarcinoma Located on the Prostate, Stage T2a Patient Data Patient O-S, 69 years old, male.

Initial Diagnosis

Prostatic acinar adenocarcinoma, Gleason grade 7 (4+3), at a T2a stage.

Identification and Summary of the Clinical History

PSA increased by 20, with biopsy revealing an acinar adenocarcinoma, Gleason grade 7 (4+3) and T2a stage—It is noteworthy that the patient had a comorbid allergic rhinitis.

Conventional Proposed and Realized Treatment

Total prostatectomy as a form of curative surgery for localized disease (confined to the prostate). It was held uneventfully on 18 Feb. 2010.

Results of the Performed Conventional Treatment and the Final Diagnosis

The final diagnosis through pathology describes the disease spread with locoregional adenocarcinoma of the prostate, Gleason grade 9 (4+5) with a TNM pT3bN0 2002 stage, affecting 22% of the glandular volume (tumor volume of 11.2 cc) and located in both lobes of the gland. The neoplasm infiltrated the seminal vesicle and periprostatic fat, but the iliac lymph nodes and bladder neck were free of neoplasia.

Final conclusion: surgical treatment was ineffective since tumor mass remained in the periprostatic region compromising the chance of a proposed cure. The proposed treatment was radiotherapy in two months and oncological follow up every 6 months for 5 years.

Immunological Evaluation Prior to Treatment with DECA

The first consultation was held on 9 Mar. 2010 and the patient requested immunological evaluation and the possibility of immunotherapy to contain the disease before the radiotherapy that would be held in two months.

Figure 7:
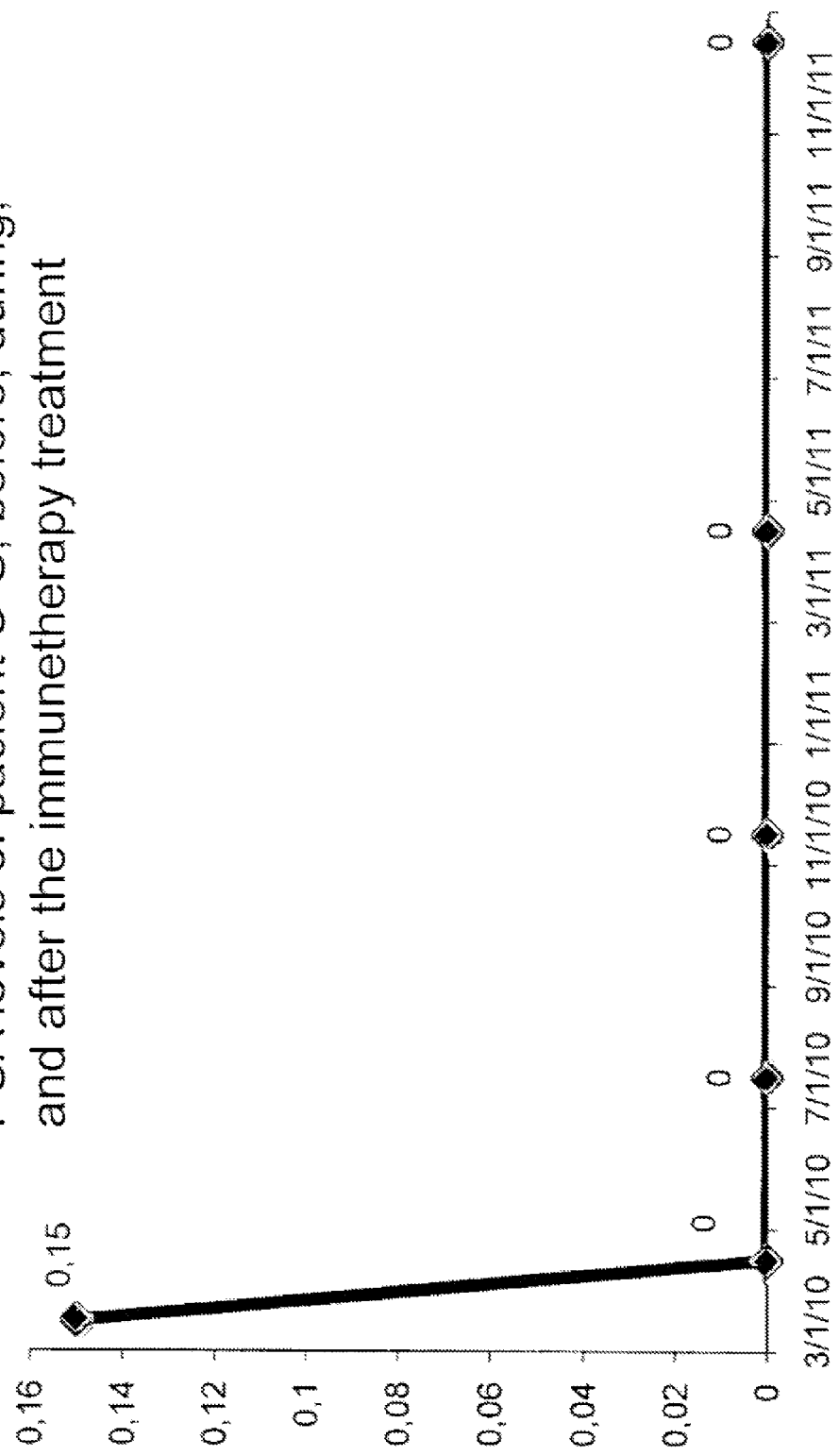
FIG. 7 shows tests of prostate specific antigen (PSA) serum levels in patient O-S. The first point refers to the residual value of the marker indicating the presence of residual neoplastic cells after non curative, which while being treated immunologically became undetectable (plotted as zero) in 4 weeks. This data strongly suggests that the immunotherapy treatment, provided it was the single drug therapy adopted pending the start of radiation therapy was effective in complete remission of the tumor and locoregional tumor eradication, since the current state of the art does not allow to differentiate complete eradication of the tumor mass in minimal residual disease.

An oncological laboratory evaluation was performed on 10 Mar. 2010 with a PSA of 0.15, compatible with a residual tumor due to ineffective prostatectomy status (FIG. 7).

The prior immunological evaluation demonstrated by blood tests on 10 Mar. 2010 showed:

Compatible TH1 cell profile with a good antitumoral response by presenting antibodies at the lower limit of normal:
Ig G 977 mg/dL (NV=600-1500);
Ig A 233 mg/dL (NV=50 to 400 mg/dL)
Ig M 112 mg/dL (NV=50 to 300 mg/dL)
albumin 3.67 g/dL (3.50 to 4, 85 g/dL)
gamma globulin 0.97 g/dL (NV=from 0.74 to 1.75 g/dL).
phenotypically normal T loop with:
$CD4^+$ 846/mm$^3$;
$CD8^+$ 504/mm$^3$;
$CD4^+/CD8^+$ ratio 1.7
Assessment of moderate allergy:
Ig E 204 mg/dL (NV=less than 100 mg/dL);
Dust specific IgE 1.5 mg/dL
(Class 2 moderate);
evaluation of positive autoimmunity for the following markers:
nuclear ANA≥1/640;
nucleolar ANA≥1/640;
In vivo tests (primary and secondary delayed hypersensitivity) were not performed due to the short remaining time for immunotherapy before radiotherapy.

Conclusion Based on the In Vitro Exams:

1. humoral immunity, complement system and T loop presented themselves phenotypically normal and without apparent immunodeficiency;
2. TH1 cell profile conducive for a good response to immunotherapy;
3. functional tests not performed because no tests were performed in vivo.

Proposed Treatment with DECA

The DECA Treatment Consisted of:

Application of 1.8 cc of the DECA composition in two applications of 0.9 cc to 10 of the major lymphatic territories.

3-4 cm distance margin between applications to facilitate the reading of the evolution of the treatment at an interval of 4±1 days.

Administration of 6 DECA compositions of 1.8 cc each divided into two perilesional applications of 0.9 cc each around the following regions: the upper and lower right and left inguinal segment totaling four compositions in these regions, as well as a suprapubic composition and other composition in the lower abdomen (infraumbilical).

Application of recombinant human interleukin-2 at low doses, at a receptor saturation level with a concentration of 1 to 2 million units per m$^2$ of the patient's body surface located in the region of the extra DECA applications. Thus, in the days of antigen application, and afterwards a daily subcutaneous application of million units in the regions listed above.

Thus, up to the time of the radiotherapy, a immunotherapy treatment was chosen with the free and informed consent of the patient, that began on 11 Mar. 2010 with the first partial reevaluation scheduled for 3 Apr. 2010.

First partial result of the proposed treatment with DECA

After 4 weeks of treatment, the PSA became undetectable (FIG. 7), indicating a complete remission induced by immunotherapy which is apparently capable of eliminating or significantly reducing the tumor mass. By the current state of the art, it is not possible to differentiate the complete eradication of the tumor mass with a minimal residual disease, showing that the proposed treatment with DECA showed a surprising effect.

On this occasion (3 Apr. 2010), it could be verified:
Ig G 1070 mg/dL (NV=600-1500);
Ig A 248 mg/dL (NV=50 to 400 mg/dL);
Ig M 129 mg/dL (NV=50 to 300 mg/dL);
The whole complement system without significant changes (280 on 10 Mar. 2010 to 281 on 3 Apr. 2010);
This maintenance of the complement system can also be found in the C3 (117 to 115) and C4 (76 to 71);
albumin 3.21 g/dL (3.50 to 4.85 g/dL);
gamma globulin 1.00 g/dL (NV=0.74 to 1.75 g/dL).
$CD4^+$ 1.075/mm$^3$;
$CD8^+$ 537 mm$^3$;
$CD4^+/CD8^+$ ratio 2.0.
Ig E 165 mg/dL (NV=less than 100 mg/dL);
nuclear ANA≥1/320;
nucleolar ANA≥1/320;
In vivo tests (secondary delayed hypersensitivity) showed:
on the first application:
the antigens administered at a the distance from the tumor area with scores of +/++ for all the antigens;
in the region of DECAs near the residual tumor area reaction was reduced by presenting a score of +/++ in +++++ attesting to tumor immunosuppression.
second application:
The antigens administered at a distance from the tumor became hyperergic with a score of +++/++++ to all the antigens;
the region of DECAs near the residual tumor area normalized, starting to show a score of ++/+++ on +++++ confirming a reversal of immunosuppression caused by the residual tumoral mass.
in the third application (beginning of the second week of treatment):
the antigens administered at a distance from the tumor became more hyperergic with scores of ++++/+++++ to all the antigens;
the region of DECAs near the residual tumor area reached the same level of activity (for ++++/+++++) attesting a complete reversal of the locoregional immunosuppression of the residual mass.

These hyperergic reactions continued until the date of the reevaluation of the fourth week (3 Apr. 2010).

Conclusion of the First Partial Result of the Proposed Treatment with DECA

The patient was initially with a preserved systemic immunity with the cell Th1 profile. This cell Th1 profile was compromised in regions close to the tumor with an unresponsive T loop attesting a locoregional tumor immunosuppression.

Immunotherapy made the secondary delayed hypersensitivity hyperergic in all territories at a distance from the tumor after the second application of DECA and reversed locoregional immunosuppression which became hyperergic like the others.

Blood tests corroborate with the functional analysis of the T loop showing an increase of CD4$^+$/helper cells in absolute and relative numbers and an increase in the CD4$^+$/CD8$^+$ ratio attesting the mobilization of CD4$^+$ cells at a systemic level that restored cellular immunity of the patient. Blood tests also showed a specific action of the DECA composition exclusively on cellular immunity because the antibodies and the complement system remained unchanged in the first phase of treatment.

In parallel we observed other allergy and autoimmune benefits:

reduction of IgE class antibodies accompanied by complete remission of the comorbid allergic rhinitis manifested in the patient suggesting an antiallergic action of the proposed DECA treatment.

Significant reduction of the ANA score that went from 1/640 to 1/320 showing a probable regression to the tendency to autoimmunity;

End Result of the Proposed Treatment with DECA Before Radiotherapy

On 27 Apr. 2010 a second partial reassessment was held the when the patient presented painful hyperergic reactions (all with +++++). Given the outcome of undetectable PSA and it remained so until February 2012.

The immunological treatment that began on 11 Mar. 2010 continued until 10 Jun. 2010 (the day before radiotherapy) totaling 90 days, emphasizing that complete remission of the tumor was achieved after 4 weeks and the reversal of immunosuppression in 2 weeks.

Results of Treatment with DECA

Due to the complete remission of a patient with prostatic adenocarcinoma with a Gleason grade of 9 (4+5) and a surgical staging of pT3bN0 with a postoperative residual tumor mass, in 4 weeks, it can be inferred that the results are surprising when compared to the state of the art pointing these cases as difficult to reverse.

It is possible to further assume that in this first month of treatment, the DECA immunotherapy demonstrated a potencial antiallergenic ability (reduction of IgE associated with complete remission of allergic rhinitis), and as a regressor of the tendency to autoimmunity (as evidenced by a reduction by half of the titration of antibodies against nuclear elements).

Conclusion of the Case

These data strongly suggest that the immunotherapy treatment with DECA, provided it was the only pharmacological treatment adopted while awaiting for the start of the radiation therapy, was effective in the complete remission of the remaining locoregional tumor (in 4 weeks) from a prostatectomy, backed by the the conversion of PSA levels until undetectable, thus representing eradication of the tumor mass, since the current state of the art does not allow to differentiate between the complete eradication of the tumor mass and minimal residual disease.

Additionally we observed complete remission of allergic rhinitis and improved levels of ANA (probably the tendency of enhancing autoimmunity).

Example 8

Fighting a Septicemia

Patient Data
Patient J-P, 58 years old, male.
Principal Diagnosis
Septicemia.
Secondary Diagnoses Polytrauma with:
Complex infected wounds with major loss of tissue of approximately 40 cm.
extensive infected tissue necrosis with indication for amputation of the left lower limb.
infected grade IIIB open fracture with osteomyelitis of the left femur with lateral exposure.
open wounds, infected cut-contusion without possibility of suture on the left arm, back of the left foot and on the right lateral malleolus region.

Identification and Summary of the Clinical History

On Jan. 12, 2011 the patient was admitted to the Intensive Care Unit of the Octavian Constantine Hospital das Clinicas of Teresopolis, victim of a landslide with a grade III b open fracture of the left femur with the exposure of the lateral cut and medial cut-contusion with an extension of 40 cm in depth that communicated with the exposure of the side. Lacerations, contusion on the left arm, back of the left foot and right lateral malleolus region. Evolved to a sepsis scenario in 24 hours, with microbiological identification of *Pseudomonas aeruginosa*.

Conventional Proposed and Realized Treatment

External fixation of the femur in the emergency room, administration of clindamycin, vancomycin and cefepime, associated to a daily surgical debridement.

Results of the Performed Conventional Treatment

Initially, it improved the septic scenario, followed by the evolution of the infection of the left lower limb with extensive areas of muscle necrosis with a high risk of amputation. 15 days after the admission the sepsis got worse, with febrile episodes of 39° C., profound anemia (receiving transfusions) and exchange of the antimicrobial medication to Tazocim. The patient was transferred with an aerial mobile ICU to Sao Paulo under medical supervision.

The completion of conventional treatment showed a relapse in sepsis and increased necrosis of the left leg with an indication for amputation.

Proposed DECA treatment associated with conventional surgical treatment

The patient was admitted to the ICU of Hospital Alemao Oswaldo Cruz for debridement and application of treatment with DECA which took the following form:

Application of 1.8 cc of the DECA composition divided into 2 applications of 0.9 cc per composition along the 10 main lymphatic territories.

3-4 cm distance margin between applications to facilitate the reading of the evolution of the treatment at an interval of 4±1 days. These applications were made together with the surgical debridement (on average 1 to 2 times per week).

Administration of 36 extra perilesional compositions of 1.8 cc of each DECA in two applications of 0.9 cc per set, skirting the following open injuries without possibility of suture: the left inguinal region, the lateral side of the left thigh, the anterior left thigh and medial aspect of the left thigh, instep region and left lateral malleolus of the right leg.

Application of recombinant human interleukin-2 at low doses, at a receptor saturation level with a concentration of 1 to 2 million units per m$^2$ of the patient's body surface located in the region of the extra DECA applications. 3 million daily units were subcutaneously injected in the left thigh or inguinal region for the pacient.

In the exposed regions 15 compositions DECA were applied, 1.8 cc each, for infiltration of exposed raw areas.

This extensive immunotherapy was always applied in the operating days of cleansing and surgical debridement under general anesthesia.

Thus, the first phase of immunotherapy began on 29 Jan. 2011 and ended on 19 Mar. 2011 totaling a total of nine DECA applications in periods ranging from one to two times per week, once the cleaning and debridement schedule was being followed, in the operating room (due to the severity of the pain and risk of infection by the broad extensive exposure of internal tissues in the raw areas).

Results of the Treatment with DECA Associated with Surgical Debridement and Antibiotic Therapy Initial assessment of the patient's injuries in the operating room on 29 Jan. 2011 showed all wounds bleeding with many clots, with extensive areas of necrosis and foul-smelling pus. After surgical cleaning, tissue continued to perform poorly with a winy general appearance without any appearance of healthy granulation tissue. As described, the DECA immunotherapy was applied to these areas. It is interesting to note that on this occasion cultures of internal secretions and tissue fragments were performed.

After 24 hours the first assessment of the surgical treatment associated with DECA immunotherapy was made and it demonstrated that: red lesions, with the appearance of healthy granulation tissue, with few necrotic areas with sparse secretion without foul odor and no active bleeding. The lesions were cleaned and the DECA immunotherapy was applied as noted above. On this occasion the antibiotic therapy was changed to Tazocim Meronem, Cubicin and Rifampicin pending culture results.

On 1 Feb. 2011 the result of the cultures from the injury area, peripheral blood and central catheter showed:

in the wound of the left thigh isolation of multidrug-resistant *Pseudomonas aeruginosa*, multiresistant *Acinetobacter baunnamii* sensitive only to polymyxin B and multiresistant *Proteus mirabiles*.

in the peripheral blood and in the central catheter the isolation of multidrug-resistant *Acinetobacter baunnamii* sensitive only to polymyxin B.

Conclusion: These results demonstrated that the poor prognosis of injuries in the left leg led to a new sepsis episode with *Acinetobacter baunnamii* and because of its multidrug resistance and sensitivity only to polymyxin B, did not respond to treatment with intravenous Tazocim. On the other hand, it strongly supports a beneficial effect of the DECA composition in joint surgical treatment in the local and systemic protection against this infection, since there was improvement in systemic infection and injuries before the application of polymyxin B could neutralize this etiologic agent.

That day, Meronem was exchanged for 20,000 IU/kg twice daily of Polymyxin B without changing the other medication.

On 3 Feb. 2011, it was found that the combination antibiotic therapy, debridement and DECA immunotherapy caused the remission of the septic scenario, which allowed the transfer of the patient from the ICU to the ward thereafter.

On 6 Feb. 2011, given the toxicity of Polymyxin B administration and other antimicrobials, the patient presented a picture of acute renal failure with oliguria. As a consequence, on the period between 6 Feb. 2011 and 15 Feb. 2011 (12 days) administration of these antibiotics was suspended, with Limezolida (Zyvox) being introduced for protection against a hospital staphylococcal contamination. On 15 Feb. 2011 the complete remission of renal failure in the patient was confirmed. In this 12-day period, with only the combination therapy of debridement, antibiotic prophylaxis and DECA immunotherapy, the patient showed excellent overall progress of the infectious and injuries being, after this period, able to withdraw the external fixator, have a surgical cleanup, and introduction of an internal rod for fixing the fracture on a surgery performed on 17 Feb. 2011. Thus, in this period, together with orthopedic surgery, there was a significant reduction in raw areas without skin with extensive tissue regeneration and no new infections.

The patient was discharged on 15 Mar. 2011 with complete cure of the infection of all complex injuries and wounds, including osteomyelitis. The patient was discharged without antibiotic therapy.

Conclusion of the Case

The existence of a severe and widespread infection and of a complex wound infected with multidrug-resistant *Acinetobacter baunnamii* sensitive only to polymyxin B which was controlled without specific antibiotic therapy with broad progression to the healing of sepsis, of all exposed lesions, and of osteomyelitis, strongly suggest a decisive role of the DECA immunotherapy, associated with debridement and antibiotics, to cure the clinical scenario, in a relatively short time.

TABLE 2

Result of the association of DECA immunotherapy, antibiotics and surgical debridement for sepsis and severe infection of complex injuries.

| Infected regions | Pre-immunotherapy cultures (29/01/2011) | Result of the association of immunotherapy, antibiotic therapy, and surgical debridement (15/03/2011) |
| --- | --- | --- |
| Injury in the left thigh | Multiresistant *Pseudomonas aeroginosa*, multiresistent *Acinetobacter baumannii* only sensitive to Aztreonam and polymyxin B | No signs of infection |
| Peripheric blood | multiresistent *Acinetobacter baumannii* only sensitive to Aztreonam and polymyxin B | No signs of infection |
| Central catheter | multiresistent *Acinetobacter baumannii* only sensitive to Aztreonam and polymyxin B | No signs of infection |

In short, the clinical cases presented here demonstrate that illnesses and diseases considered of a high complexity and with an obscure to very poor prognosis when analyzed by the knowledge of the prior art, have been addressed differently, more advantageously and more efficiently through the use of the compositions the present invention.

The invention claimed is:

1. A method to modulate an immune system response in a human or animal who has cancer, comprising administering to the human or animal an effective amount of one or more immunogenic compositions for modulating the immune system comprising a therapeutically effective amount of three or more synthetic antigenic agents or natural antigenic agents, or fractions and combinations thereof, comprising pathogen-associated molecular patterns (PAMPS) and/or danger associated molecular patterns (DAMPS) selected from at least two groups consisting of: (A)

antigenic agents with molecular patterns associated with bacteria, (B) antigenic agents with molecular patterns associated with viruses, (C) antigenic agents with molecular patterns associated with fungi and yeasts, (D) antigenic agents with molecular patterns associated with protozoa, (E) antigenic agents with molecular patterns associated with helminthes, and (F) antigenic agents with molecular patterns associated with prions; and one or more physiologically acceptable carriers, excipients, diluents or solvents.

2. The method according to claim 1, wherein the cancer is carcinoma, adenocarcinoma, melanoma, sarcoma, malignant astrocytoma, hepatoma, hypernephroma, lymphoma or melanoma.

3. The method according to claim 1, further comprising administering to the human or animal one or more cytokines and/or chemokines.

4. The method according to claim 3, further comprising administering to the human or animal GM-CSF, IL2, IL4, IL5, IL7, IL12, IL15, IL21 and/or interferon gamma.

5. The method according to claim 4, further comprising administering to the human or animal IL2.

6. The method according to claim 1, wherein the method is used before, during or after antibiotic therapy, chemotherapy, radiation therapy, therapy with antibodies and antisera, use of hormones, use of cytokines, use of chemokines, use of neurohormones, use of peptides, use of antivirals, use of phytotherapy, vitamin supplementation, supplementation with other cofactors or prosthetic agents, transplantation of cells or tissues, methods of therapeutic or prophylactic vaccination, gene therapy, surgery, or homeopathic therapy.

7. The method according to claim 1, wherein the immunogenic composition for modulating the immune system comprises from 4 to 20 antigenic agents selected from the group consisting of antigenic agents derived from: dornase, yeast extract, oidiomycin, purified protein derivative of Koch's *bacillus* (PPD), prions, streptokinases, *Streptococcus* toxoid, diphtheria toxoid, tetanus toxoid, Koch's original tuberculin, *Aspergillus* spp., *Candida* spp., *Chlamydia pneumoniae*, *Chlamydia psittaci*, *Chlamydia trachomatis*, *Cryptosporidium* spp., *Dermatophytes*, *Entamoeba hystolitica*, *Enterobius vermicularis*, *Enterococcus faecalis*, *Epidermophyton floccosum*, *Escherichia coli*, *Giardia lamblia*, *Haemophilus influenzae*, *Microsporum canis*, *Mycobacterium* spp., *Neisseria gonorrhoeae*, Human *papillomavirus*, Polio virus, *Proteus* spp., *Salmonella* spp., *Serratia* spp., *Shigella* spp., *Staphylococcus* spp., *Strongyloides stercoralis*, *Streptococcus* spp., *Toxoplasma gondii*, *Trichomonas vaginalis*, trichophytin, *Trichophyton rubrum*, *Trichophyton tonsurans*, *Trichophyton mentagrophytes*, yellow fever virus, hepatitis B virus, rubella virus, varicella zoster virus, variola virus, mumps virus, measles virus, herpes virus, or vaccinia virus, synthetic analogues presenting pathogen-associated molecular patterns (PAMPS) associated with these antigenic agents, and synthetic analogues presenting danger-associated molecular patterns (DAMPS) associated with these antigenic agents.

8. The method of claim 1, wherein the immunogenic composition for modulating the immune system comprises lysate of inactivated *Mycobacterium bovis*, purified protein derivative of *M. tuberculosis*, lysate of inactivated *Staphylococcus aureus*, lysate of inactivated *Staphylococcus epidermidis*, lysate of inactivated *Streptococcus pyogenes*, lysate of inactivated *Streptococcus pneumoniae*, lysate of inactivated *Enterococcus faecalis* Streptokinase, dornase, lysate of inactivated *Candida albicans*, lysate of inactivated *Candida glabrata*, lysate of inactivated *Epidermophyton floccosum*, lysate of inactivated *Microsporum canis*, lysate of inactivated *Trichophyton mentagrophytes* of the *interdigitale* variety, lysate of inactivated enteropathogenic *Escherichia coli*, lysate of inactivated *Salmonella bongori*, lysate of inactivated *Salmonella enterica* and lysate of inactivated *Salmonella subterranea*.

9. The method according to claim 1, wherein the immunogenic composition for modulating the immune system comprises from 0.001 to 1 ng/ml of lysate of inactivated *Mycobacterium bovis*, 0.001 to 1 ng/ml of purified protein derivative of *M tuberculosis*, 0.1 to 100 µg/ml of lysate of inactivated *Staphylococcus aureus*, 0.1 to 100 µg/ml of lysate of inactivated *Staphylococcus epidermidis;* 0.1 to 100 µg/ml of lysate of inactivated *Streptococcus pyogenes;* 0.1 to 100 µg/ml of lysate of inactivated *Streptococcus pneumoniae;* 0.1 to 100 µg/ml of lysate of inactivated *Enterococcus faecalis*, 0.01 to 10 µg/ml of streptokinase, 0.01 to 10 µg/ml of dornase; 0.1 to 100 µg/ml of lysate of inactivated *Candida albicans;* 0.1 to 100 µg/ml of lysate of inactivated *Candida glabrata*, 0.1 to 100 µg/ml of lysate of inactivated *Epidermophyton floccosum;* 0.1 to 100 µg/ml of lysate of inactivated *Microsporum canis*, 0.1 to 100 µg/ml of lysate of inactivated *Trichophyton mentagrophytes* of the *interdigitale* variety; 0.1 to 100 µg/ml of lysate of inactivated enteropathogenic *Escherichia coli;* 0.1 to 100 µg/ml lysate of inactivated *Salmonella bongori*, 0.1 to 100 µg/ml lysate of inactivated *Salmonella enterica* and 0.1 to 100 µg/ml of lysate of inactivated *Salmonella subterranea*.

10. The method according to claim 1, wherein the immunogenic composition comprises at least three natural or synthetic antigen agents from different microorganisms.

11. The method according to claim 1, wherein the immunogenic composition comprises at least four natural or synthetic antigen agents from different microorganisms.

12. The method according to claim 1, wherein administering comprises administering systemically and/or locally on the human or animal, and the method further comprises:

ensuring the contact of the one or more immunogenic compositions with dendritic cells or other antigen presenting cells (APCs) of the human or animal;

optionally administering prosthetic agents to strengthen the metabolism and therefore the immune system of the human or animal, and optionally administering other medications or specific treatments.

13. The method according to claim 7, wherein the

*Aspergillus* spp. is selected from the group consisting of *Aspergillus flavus*, *Aspergillus fumigatus*, and *Aspergillus terreus;*

*Candida* spp. is selected from the group consisting of *Candida albicans*, *Candida glabrata*, and *Candida parapsilosis;*

*Mycobacterium* spp. is selected from the group consisting of *Mycobacterium bovis*, *Mycobacterium leprae*, and *Mycobacterium tuberculosis;*

*Proteus* spp. is selected from the group consisting of *Proteus mirabilis*, *Proteus penerii*, and *Proteus vulgaris;*

*Salmonella* spp. is selected from the group consisting of *Salmonella bongori* and *Salmonella enterica;*

*Serratia* spp. is selected from the group consisting of *Serratia liquefaciens* and *Serratia marcescens;*

*Shigella* spp. is selected from the group consisting of *Shigella flexneri* and *Shigella sonnei*;
*Staphylococcus* spp. is selected from the group consisting of *Staphylococcus aureus*, and *Staphylococcus epidermidis*; and
*Streptococcus* spp. is selected from the group consisting of *Streptococcus bovis, Streptococcus viridans, Streptococcus equinus, Streptococcus pneumoniae*, and *Streptococcus pyogenes*.

\* \* \* \* \*